US011969434B1

(12) United States Patent
Ogle et al.

(10) Patent No.: US 11,969,434 B1
(45) Date of Patent: Apr. 30, 2024

(54) ORAL ALLOPREGNANOLONE COMPOSITIONS AND METHODS OF USE

(71) Applicant: Lipocine Inc., Salt Lake City, UT (US)

(72) Inventors: Jonathan Ogle, Salt Lake City, UT (US); Benjamin J. Bruno, Salt Lake City, UT (US); Kongnara Papangkorn, Salt Lake City, UT (US); Samuel Akapo, Salt Lake City, UT (US); Joel Frank, Salt Lake City, UT (US); Nachiappan Chidambaram, Salt Lake City, UT (US); Mahesh V. Patel, Salt Lake City, UT (US)

( * ) Notice: Subject to any disclaimer, the term of this patent is extended or adjusted under 35 U.S.C. 154(b) by 0 days.

(21) Appl. No.: 17/823,080

(22) Filed: Aug. 29, 2022

(51) Int. Cl.
| | |
|---|---|
| *A61K 31/57* | (2006.01) |
| *A61K 9/00* | (2006.01) |
| *A61K 9/14* | (2006.01) |
| *A61K 31/557* | (2006.01) |
| *A61P 15/06* | (2006.01) |
| *A61P 21/00* | (2006.01) |

(52) U.S. Cl.
CPC ............ *A61K 31/57* (2013.01); *A61K 9/0053* (2013.01); *A61K 9/14* (2013.01); *A61K 31/557* (2013.01); *A61P 15/06* (2018.01); *A61P 21/00* (2018.01)

(58) Field of Classification Search
CPC ..... A61K 31/57; A61K 9/0053; A61K 31/557
See application file for complete search history.

(56) References Cited

U.S. PATENT DOCUMENTS

| | | | |
|---|---|---|---|
| 5,028,600 A | 7/1991 | Jeppsson | 514/182 |
| 6,982,281 B1 | 1/2006 | Chen | 514/458 |
| 8,119,619 B2 | 2/2012 | Backstrom | 514/169 |
| 8,697,678 B2 | 4/2014 | Goodchild | 514/178 |
| 8,951,996 B2 | 2/2015 | Giliyar | A61K 9/4841 |

(Continued)

FOREIGN PATENT DOCUMENTS

| | | | | |
|---|---|---|---|---|
| CA | 3136389 A1 | * 10/2020 | ......... | A61K 31/5513 |
| WO | WO199703651 | 2/1997 | ............ | A61K 9/107 |

(Continued)

OTHER PUBLICATIONS

Jennifer J. Liang et al., Overview of the Molecular Steps in Steroidogenesis of the GABAergic Neurosteroids Allopregnanolone and Pregnanolone, Chronic Stress, Nov. 19, 2018, vol. 2, pp. 1-17.

(Continued)

*Primary Examiner* — San Ming R Hui
(74) *Attorney, Agent, or Firm* — Michael R. Schramm

(57) ABSTRACT

Disclosed is a method and an oral composition for treating CNS disorders. An embodiment of the invention comprises orally administering an allopregnanolone containing composition to a subject having a CNS disorder. Exemplary CNS disorders include sleep disorders, mood disorders, dysthymic disorders, bipolar disorders, anxiety disorders, stress disorders, compulsive disorders, schizophrenia spectrum disorders, convulsive disorders, memory disorders, cognition disorders, movement disorders, personality disorders, autism spectrum disorders, substance abuse disorders, dementia, pain, traumatic brain injury (TBI), vascular disease, withdrawal syndrome, and tinnitus. The composition and methods disclosed herein exhibit effective oral absorption/bioavailability.

33 Claims, 4 Drawing Sheets

(56) References Cited

U.S. PATENT DOCUMENTS

| | | | |
|---|---|---|---|
| 8,975,245 B2 | 3/2015 | Goodchild | A61K 47/40 |
| 9,358,298 B2 | 6/2016 | Giliyar | A61K 47/44 |
| 9,358,299 B2 | 6/2016 | Giliyar | A61K 47/44 |
| 9,364,547 B2 | 6/2016 | Giliyar | A61K 47/44 |
| 9,375,437 B2 | 6/2016 | Nachaegari | A61K 31/57 |
| 9,399,069 B2 | 7/2016 | Giliyar | A61K 47/44 |
| 9,757,391 B2 | 9/2017 | Goodchild | A61K 31/573 |
| 10,022,384 B2 | 7/2018 | Giliyar | A61K 9/145 |
| 10,251,894 B2 | 4/2019 | Rogawski | A61K 31/57 |
| 10,322,139 B2 | 6/2019 | Reddy | A61K 31/57 |
| 10,478,505 B2 | 11/2019 | Rogawski | A61K 47/46 |
| 10,639,317 B2 | 5/2020 | Cashman | A61K 31/573 |
| 10,709,716 B2 | 7/2020 | Giliyar | A61K 31/57 |
| 10,940,156 B2 | 3/2021 | Kanes | A61K 31/57 |
| 11,000,531 B2 | 5/2021 | Cashman | A61K 31/573 |
| 2005/0119340 A1 | 6/2005 | Anderson | 514/535 |
| 2007/0026062 A1 | 2/2007 | Holm | 424/451 |
| 2007/0112017 A1 | 5/2007 | Barlow | 514/282 |
| 2010/0028360 A1 | 2/2010 | Atwood | 424/158.1 |
| 2011/0312927 A1 | 12/2011 | Nachaegari | 514/177 |
| 2011/0312928 A1 | 12/2011 | Nachaegari | 514/177 |
| 2013/0029947 A1 | 1/2013 | Nachaegari | 514/170 |
| 2013/0029957 A1 | 1/2013 | Giliyar | 514/177 |
| 2014/0271882 A1 | 9/2014 | Giliyar | A61K 31/57 |
| 2014/0377317 A1 | 12/2014 | Giliyar | A61K 8/63 |
| 2015/0165049 A1 | 6/2015 | Giliyar | A61K 47/44 |
| 2015/0320768 A1 | 11/2015 | Giliyar | A61K 31/57 |
| 2016/0030583 A1 | 2/2016 | Fikstad | A61K 47/44 |
| 2016/0213686 A1 | 7/2016 | Giliyar | A61K 31/57 |
| 2017/0007623 A1 | 1/2017 | Giliyar | A61K 31/57 |
| 2017/0035781 A1 | 2/2017 | Giliyar | A61K 31/57 |
| 2017/0348273 A1 | 12/2017 | Kanes | A61K 31/573 |
| 2018/0099053 A1 | 4/2018 | Fikstad | A61K 47/44 |
| 2018/0289724 A1 | 10/2018 | Giliyar | A61K 31/57 |
| 2019/0275060 A1 | 9/2019 | Giliyar | A61K 31/57 |
| 2019/0307775 A1 | 10/2019 | Giliyar | A61K 31/57 |
| 2019/0351019 A1 | 11/2019 | Cooper | A61K 38/191 |
| 2020/0069805 A1 | 3/2020 | Fikstad | A61K 47/44 |
| 2020/0281943 A1 | 9/2020 | Hoffmann | A61K 31/58 |
| 2021/0106596 A1 | 4/2021 | Giliyar | A61K 31/57 |
| 2021/0169900 A1 | 6/2021 | Giliyar | A61K 31/57 |
| 2022/0241295 A1 | 8/2022 | Strickley | A61K 31/558 |

FOREIGN PATENT DOCUMENTS

| | | | |
|---|---|---|---|
| WO | WO2005041929 | 5/2005 | A61K 9/00 |
| WO | WO2006119498 | 11/2006 | A61K 9/22 |
| WO | WO2013016697 | 1/2013 | A61K 31/57 |
| WO | WO2013112605 | 8/2013 | A61K 31/57 |
| WO | WO2014085668 | 6/2014 | A61K 31/56 |
| WO | WO-2014085668 A1 * | 6/2014 | A61K 31/56 |
| WO | 2016040322 A1 | 3/2016 | |
| WO | WO2016210003 | 12/2016 | A61K 31/57 |

OTHER PUBLICATIONS

Sage Therapeutics, Zulresso Prescribing Information Reference ID 4405779, Mar. 19, 2019, pp. 1-21.

Arne Wessen et al., Concentration-Effect Relationships of Eltanolone Given as a Bolus Dose or Constant Rate Intravenous Infusion to Healthy Male Volunteers, Jun. 1996, vol. 84, No. 6, pp. 1317-1326.

Dorota Zolkowska et al., Intranasal Allopregnanolone Confers Rapid Seizure Protection: Evidence for Direct Nose-to-Brain Delivery, Jan. 6, 2021, pp. 544-555.

Irwin, Ronald W.; "Allopregnanolone Preclinical Acute Pharmacokinetic and Pharmacodynamic Studies to Predict Tolerability and Efficacy or Alzheimer's Disease," PLOS One; Jun. 3, 2015; 10(6); e0128313; doi: 10.1371/journal.pone.0128313.

* cited by examiner

ORAL ALLOPREGNANOLONE COMPOSITIONS AND METHODS OF USE

CROSS REFERENCE TO RELATED APPLICATIONS

U.S. Pat. No. 11,337,987 to Patel et al. issued May 24, 2022 and U.S. patent application Ser. No. 17/706,210 to Kim et al. filed Mar. 28, 2022 and Ser. No. 17/723,203 to Kim et al. filed Apr. 18, 2022 are expressly incorporated herein in their entirety by this reference.

FIELD OF THE INVENTION

The present disclosure relates to compositions, dosage forms and regimens, and methods of treating a subject in need of oral allopregnanolone. Accordingly, this disclosure involves the fields of chemistry, pharmaceutical sciences, medicine, and other health sciences.

BACKGROUND OF THE INVENTION

Allopregnanolone (also known as brexanolone), is an endogenous inhibitory pregnane neuroactive steroid (NAS). It is a positive allosteric modulator of the action of γ-aminobutyric acid (GABA) at $GABA_A$ receptor. Allopregnanolone has effects similar to those of other positive allosteric modulators of the GABA action at $GABA_A$ receptor such as the benzodiazepines, including anxiolytic, sedative, and anticonvulsant activity. Endogenously produced allopregnanolone exerts a neurophysiological role by fine-tuning of $GABA_A$ receptor and modulating the action of several positive allosteric modulators and agonists at $GABA_A$ receptor.

Although reports of intranasal, sub-cutaneous forms have been reported in the literature, allopregnanolone is only approved as a cyclodextrin (a cyclic oligosaccharides) comprising aqueous (5 mg/ml of brexanolone) intravenous infusion with a considerable quantity (250 mg/ml) of a betadex sulfo butyl ether sodium solubilizer, ZULRESSO, for the treatment of post-partum depression. ZULRESSO requires hospitalization and needs to be administered by a health care provider in a recognized health care setting. Besides privacy and social stigma issue, protocol requires a patient's admission to an inpatient unit that allows for careful monitoring. Moreover, hospitalization can be demanding to a mother when she is bonding with her newborn, or perhaps back at work and juggling many demands on her time. Furthermore, parenteral ZULRESSO also presents cost, access and logistics issues as well as a healthcare facility need significant time to become treatment ready.

Reportedly, allopregnanolone has a very low water solubility, high lipophilicity, and low oral bioavailability necessitating non-oral administration (Scott L J (May 2019)). Various approaches have been tried to enable effective oral absorption; however, there is presently no known acceptable approach utilizing an oral composition comprising allopregnanolone for effective oral administration due to its reported poor rate and extent of absorption post oral administration. Use of solution in edible oils, such as canola oil, MIGLYOL (a caprylic/capric triglyceride), or suspension in TWEEN-80 (polysorbate-80) to enhance the central nervous system (CNS) activity of orally administered allopregnanolone in mice has been attempted (U.S. Pat. No. 10,478,505 B2). However, no appreciable CNS activity was noted with allopregnanolone compositions consisting of suspension in TWEEN-80, and solution in MIGLYOL.

Oral aqueous SBE-β-CD (Sulfobutylether-β-Cyclodextrin) formulations, such as ZULRESSO, comprising allopregnanolone have a propensity to be displaced from the SBE-β-CD complex by the gastrointestinal contents, and also may exhibit sensitivity to displacement due to dilution in gastrointestinal contents that could compromise its oral absorption. Moreover, orally administered cyclodextrins at high doses may cause digestive problems, such as diarrhea, as evidenced from the oral administration of hydroxy propyl-β-CD at daily doses of 16-24 g for 14 days to human volunteers resulting in an increased incidence of soft stools and diarrhea.

Furthermore, a fully solubilized aqueous allopregnanolone composition such as an SBE-β-CD based composition, although expected to perform better relative to a non-fully solubilized composition e.g., solid formulation, when administered orally, reportedly, resulted in subpar pharmacokinetics ($C_{max}$, $AUC_{0-24}$, etc.) desired for a CNS indication with allopregnanolone blood levels demonstrating sensitivity to food effects. This may suggest that in vitro solubilization and/or in vitro disintegration/release of active from an immediate release composition may not be a good predictor of resulting pharmacokinetics (PK) nor pharmacodynamic effects of the active, allopregnanolone.

The current state of the art reports limited (poorly absorbed/bioavailable solution or semi-solid) allopregnanolone compositions for oral delivery with no specific teachings on any solid-state compositions, e.g., tablets or capsules, etc. and associated methods for effective bioavailability/absorption of allopregnanolone post oral administration. Moreover, an effective oral dose, specifically with orally useful compositions or method to treat a CNS disorder indication is unknown. Hence, there is presently no acceptable approach to allow an oral compositions or dosage form comprising allopregnanolone to provide therapeutically effective levels of allopregnanolone for treatment of CNS disorders or any disorders. Moreover, a specific CNS disorder may require an appropriate pharmacokinetic profile with respect rate of absorption resulting in desirable or needed $T_{max}$ and/or $C_{max}$ as well as adequate extent of absorption or blood level exposure from an oral composition/dosage form and associated dosing regimen or method of administration resulting desirable rate and extent of allopregnanolone blood levels post oral administration for efficacy. Therefore, there remains an unmet need for safe and adequately absorbable and/or bioavailable oral compositions and methods of allopregnanolone to treat human patients in need of allopregnanolone therapy for a CNS indication or any indication. Importantly, there remains an unmet need for e.g., solid compositions including a substantially non-solid such as solution or a suspension composition filled in a capsule and methods with appropriate pragmatic oral daily dose to enable effective absorption rate resulting in desirable $C_{max}$ or extent of absorption from a dosage form resulting in desirable $AUC_{0-24}$ for efficacy and safety.

SUMMARY OF THE INVENTION

The present disclosure encompasses compositions and oral dosage forms and dosing regimens including allopregnanolone and related methods. The compositions and oral dosage forms can be formulated to include a therapeutically effective amount of allopregnanolone and a plurality of pharmaceutically acceptable additives. In one aspect, the pharmaceutically acceptable additive of the composition or dosage form can provide allopregnanolone in a daily amount sufficient to treat a CNS disorder when orally administered to a subject. In another aspect, the composition or dosage form or method including dose and dosing regimen that may enable effective rate and extent of oral absorption as assessed $C_{max}$ and/or $AUC_{0-24}$ or render efficient oral absorption/bioavailability as assessed by dose normalized $C_{max}$ and/or $AUC_{0-24}$ or enhance, increase, or maximize absorption/bioavailability of allopregnanolone when orally administered to a subject. For example, in one aspect, the absorption of allopregnanolone, when orally administered to a subject through compositions and methods of this invention, can be enabled effectively and associated CNS activity of allopregnanolone can be attained or improved.

In one aspect the compositions and methods of this invention would enable effective blood levels as needed for CNS indications with efficient daily dose. More specifically, 30 mg to 1000 mg oral daily dose for a psychiatric disorder such as insomnia, sleeping disorder, and PTSD 50-1200 mg oral daily dose for a neurological disorder such as epilepsy, essential tremor, and 100-1200 mg oral daily dose for a neurodegenerative disorder such as Alzheimer.

In another aspect, the absorption/blood levels of allopregnanolone, when orally administered to a subject through compositions and methods of this invention, can be relatively increased and/or CNS activity of allopregnanolone can be improved as compared to a composition comprising an equivalent amount of allopregnanolone essentially consisting of allopregnanolone in a cyclodextrin aqueous solution or polysorbate 80 suspension or edible oil (e.g., medium chain triglyceride or canola oil or peanut oil) solution or suspension when orally administered the subject. In further aspect, the absorption of allopregnanolone, when orally administered to a subject through compositions and methods of this invention, can be increased and/or CNS activity of allopregnanolone can be improved as compared to a composition comprising untreated crystalline forms of allopregnanolone with a surfactant of less than 0.5% w/w of the composition or as compared to a composition without a surfactant.

In one embodiment, the composition can be formulated as an oral dosage form that has from about 10 mg to about 600 mg of allopregnanolone. allopregnanolone may be treated, to result in grinded, sieved, milled, micronized, ultra-micronized or nanosized forms before formulating in an oral composition or dosage form, or amorphous or fully solubilized forms post formulating/processing in the composition or dosage form. In one embodiment a crystalline form of treated allopregnanolone comprises a particle size distribution of one of a D90 of less than 75 µm, a D90 of less 50 µm, a D90 of less 25 µm, a D10 of less than 20 µm, and a D50 of at least one of 0.15 µm to 50 µm, 30 µm to 50 µm, 0.3 µm to 30 µm, and 2 µm to 8 µm.

In one embodiment, the dose amount of the composition comprises from about 10 mg to about 1200 mg of allopregnanolone. In one aspect, the composition can be a solid, liquid, a semi-liquid or semi solid, gel, a granule, a pellet, a powder, a syrup, an emulsion, a dispersion, a suspension, a capsule, a sprinkle, a tablet, a chew, a cream, an ointment, a paste, a paste-like composition, or a drink.

In yet another embodiment, a method of treating a CNS disorder in a subject can include orally administering a therapeutically effective amount of allopregnanolone to the subject. In one aspect, the therapeutically effective amount of allopregnanolone can provide an amount/blood levels of allopregnanolone that is sufficient to treat the CNS disorder. In another aspect, the compositions comprising allopregnanolone disclosed herein may be in a form that provides a therapeutically effective amount/blood levels of allopregnanolone for treating the CNS disorder in the subject. In yet another aspect, the allopregnanolone can be combined with a plurality of additives comprising at least one lipophilic additive that is sufficient to provide a therapeutically effective amount/blood levels of allopregnanolone for treating the CNS disorder in the subject. In another aspect, the allopregnanolone can be combined with a plurality of additives comprising at least one surfactant that is sufficient to provide a therapeutically effective amount/blood levels of allopregnanolone for treating the CNS disorder in the subject.

In another aspect, the compositions comprising allopregnanolone disclosed herein may be in a form that provides a therapeutically effective amount/blood levels of allopregnanolone for treating the CNS disorder in the subject. In yet another aspect, the allopregnanolone can be combined with a plurality of additives comprising at least one lipophilic additive that is sufficient to provide a therapeutically effective amount/blood levels of allopregnanolone for treating the CNS disorder in the subject. In another aspect, the allopregnanolone can be combined with a plurality of additives comprising at least one surfactant that is sufficient to provide a therapeutically effective amount/blood levels of allopregnanolone for treating the CNS disorder in the subject. In one aspect, the composition is a solid dosage form or a non-liquid dosage form. In another aspect, the allopregnanolone form in the composition of starting form of allopregnanolone composition is a solid form or a solid crystalline form or a non-fully solubilized form.

In one aspect, the therapeutically effective amount of allopregnanolone can provide a $C_{max}$ and/or $AUC_{0-24}$ that is adequate to treat the CNS disorder.

In another aspect, the therapeutically effective amount of allopregnanolone can provide a $C_{max}$ of allopregnanolone with minimum of about 9.50 ng/mL, about 14.50 ng/mL, about 20.00 ng/mL, and about 25.00 ng/mL.

Also, in yet another embodiment, the minimum threshold for $C_{max}$ and/or dose normalized $C_{max}$ are achieved through composition and methods of this invention wherein the composition is a solid dosage form or a non-liquid dosage form or an encapsulated liquid form or a cyclodextrin free liquid form or a non-aqueous liquid form. In another aspect the minimum threshold for $C_{max}$ and/or dose normalized $AUC_{0-24}$ are achieved through composition comprising allopregnanolone form in the composition wherein the starting form of allopregnanolone for formulation or process or post formulation/processing is substantially in a solid form or a solid crystalline form or an encapsulated fully solubilized form or substantially non aqueous solubilized form or aqueous solubilized form without a cyclodextrin. In another aspect, the minimum threshold for $C_{max}$ and/or dose normalized $C_{max}$ is achieved through orally administering composition without regard to food/meal or in fasted state.

In another embodiment, the therapeutically effective amount of allopregnanolone can provide a minimum $AUC_{0-24}$ of allopregnanolone of at least one of about 18 ng*h/mL, about 19 ng*h/mL, and about 20 ng*h/mL, Also, in yet another embodiment, the therapeutically effective amount of allopregnanolone can provide a dose normalized minimum $AUC_{0-24}$ of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L. In another aspect, the therapeutically effective amount of allopregnanolone can provide a minimum $AUC_{0-24}$ of allopregnanolone of at least one of about 18 ng*h/mL, and or a dose normalized minimum $AUC_{0-24}$ of at least one of about 0.65 h/L. In one aspect the minimum threshold for $AUC_{0-24}$ and/or dose normalized $AUC_{0-24}$ are achieved through composition and methods of this invention wherein the composition is a solid dosage form or a substantially non-liquid dosage form or an encapsulated liquid form or a cyclodextrin free liquid form or a non-aqueous liquid form or a less than 250 mg/g cyclodextrin comprising form.

In another aspect the minimum threshold for $AUC_{0-24}$ and/or dose normalized $AUC_{0-24}$ are achieved through composition comprising allopregnanolone form in the composition wherein the starting form of allopregnanolone for formulation or process or post formulation/processing is substantially in a solid form or a solid crystalline form or an encapsulated fully solubilized form or substantially non aqueous solubilized form or aqueous solubilized form without a cyclodextrin. In another aspect, the minimum threshold for $AUC_{0-24}$ and/or dose normalized $AUC_{0-24}$ are achieved through orally administering composition without regard to food/meal.

BRIEF DESCRIPTION OF THE DRAWINGS

Features and advantages of invention embodiments will be apparent from the detailed description which follows, taken in conjunction with the accompanying drawings, which together illustrate, by way of example, features of the disclosure; and, wherein.

DETAILED DESCRIPTION OF THE INVENTION

Figure 1:
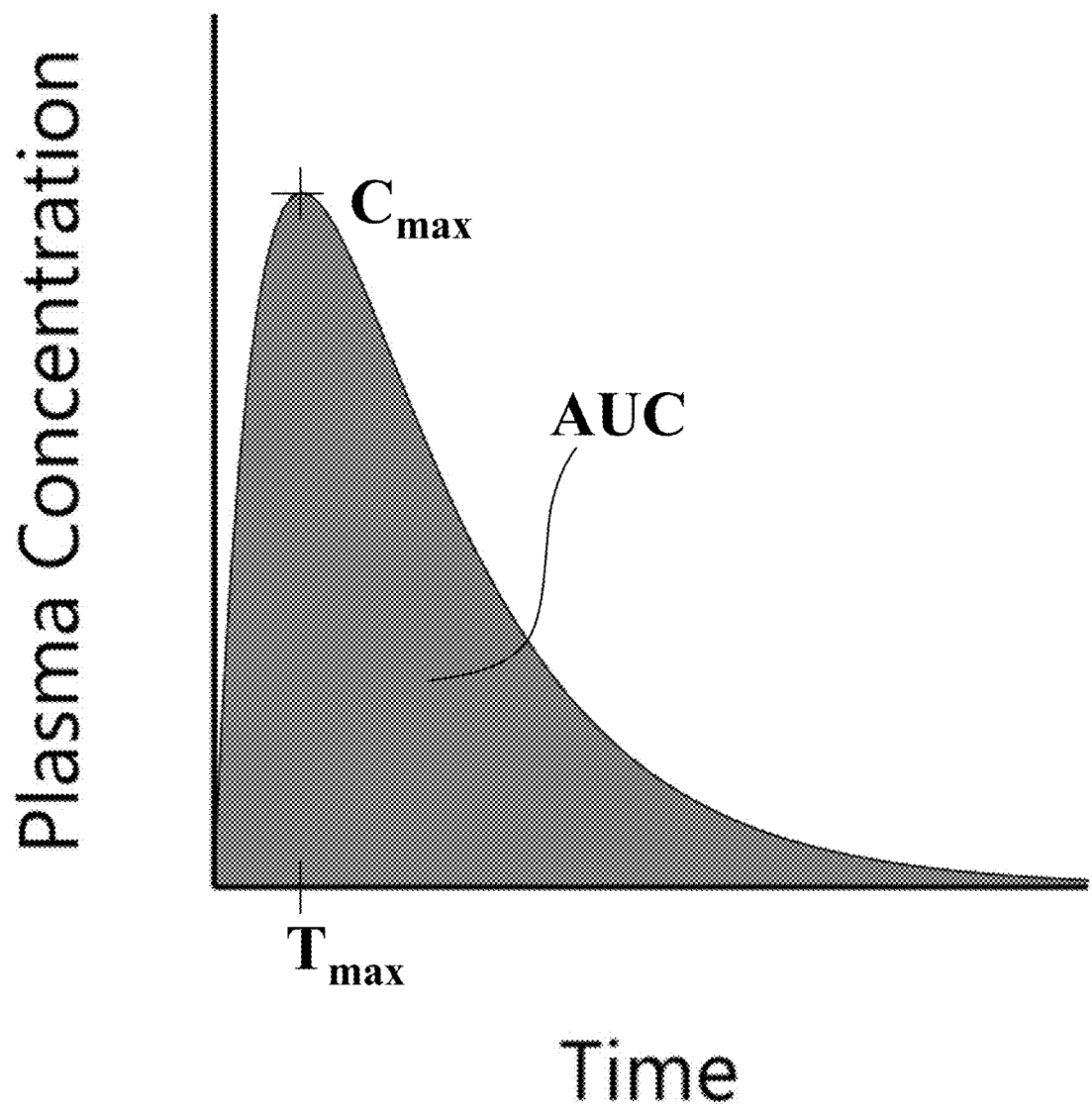
FIG. 1 is a plot of a typical pharmacokinetic profile.

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein but are merely representative thereof.

Definitions

It should be noted that, the singular forms "a," "an," and, "the" include plural referents unless the context clearly dictates otherwise. Thus, for example, reference to "an excipient" includes reference to one or more of such excipients, and reference to "the additive" includes reference to one or more of such additives.

As used herein, the terms "treat," "treatment," or "treating" and the like refers to administration of a therapeutic agent to a subject who is either asymptomatic or symptomatic. In other words, "treat," "treatment," or "treating" can refer to the act of reducing or eliminating a condition (i.e., symptoms manifested), or it can refer to prophylactic treatment (i.e., administering to a subject not manifesting symptoms in order to prevent their occurrence). Such prophylactic treatment can also be referred to as prevention of the condition, preventative action, preventative measures, and the like.

As used herein, the terms "therapeutic agent," "active agent," and the like can be used interchangeably and refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts. Further, when these terms are used, or when a particular active agent is specifically identified by name or category in this written description, it is understood that such recitation is intended to include express support for the active agent per se, as well as pharmaceutically acceptable salts, esters or compounds significantly related thereto, including without limitation, prodrugs, active metabolites, polymorphs, and the like. For example, recitation of the active agent allopregnanolone also includes express support for the active metabolites.

As used herein, the terms "formulation" and "composition" are used interchangeably and refer to a mixture of two or more compounds, elements, or molecules. In some aspects, the terms "formulation" and "composition" may be used to refer to a mixture of one or more active agents with an additive or other excipients. Furthermore, the term "dosage form" can include one or more formulation(s) or composition(s) provided in a format for administration to a subject. For example, an "oral dosage form" can be suitable for administration to a subject's mouth. A "topical dosage form" can be suitable for administration to a subject's skin by rubbing, etc.

As used herein, "pharmaceutically acceptable additive" or "additive" is used interchangeably and refer to a pharmaceutically acceptable agent or ingredient that can be combined with an active agent as part of a composition or dosage form. In some aspects, pharmaceutically acceptable additives can impact the form or behavior of an active agent. For example, in some aspects, a pharmaceutically acceptable additive can be capable of fully or partially dissolving or solubilizing an active agent (e.g., allopregnanolone) in a pharmaceutical composition or enabling a non-crystalline form of the active agent. In other aspects, a pharmaceutically acceptable additive can be formulated with an active agent (e.g., allopregnanolone) in a pharmaceutical composition comprising a crystalline form of the active agent. In one aspect, a composition, wherein the allopregnanolone comprises at least one form of substantially solubilized, partially solubilized, substantially non-solubilized, substantially crystalline, partially crystalline, substantially non-crystalline, amorphous, solid, a dispersion, and a eutectic mixture.

The term "allopregnanolone" is also known as 5α-pregnan-3α-ol-20-one; 5α-pregnane-3α-ol-20-one; 3α-hydroxy-5α-pregnan-20-one; 3α,5α-tetrahydroprogesterone; 3α,5α-THP, brexanolone, allopregnanolone. Other synonyms may also be found at the PubChem web site (such as for instance: https://pubchem.ncbi.nlm.nih.gov/compound/Allopregnanolone.

Further, in some aspects, the additives can impact or control the properties and performance of the composition or dosage form. For example, in some aspects, additives can impact or control the pharmacokinetic (PK) performance or profile (e.g., release rate and/or extent of release of the active agent) of the composition and/or the dosage form.

As used herein, a "semi-liquid" or "semi-solid" corresponds to a partially solubilized active agent and a "liquid" corresponds to a fully solubilized active agent at room temperature.

As used herein, a "subject" refers to a mammal that may benefit from the administration of a drug composition, dosage form or dosage regiment, or method disclosed herein. Examples of subjects include humans, and may also include other animals such as horses, pigs, cattle, dogs, cats, rabbits, and aquatic mammals. In one specific aspect, a subject is a human. In another aspect, the subject is a female. In another aspect, the subject is a female of childbearing age. In another aspect the female as delivered a baby within the last 1-12 months. In another aspect, the subject is male.

As used herein, "in need of treatment" and the like refers to a subject that has a disease, condition, or disorder or is suspected of having the disease, condition, or disorder according to various diagnostic criteria typically used in practice, or desires treatment or is indicated for treatment. Thus, "in need of treatment" can include the operation of identifying a subject in need of treatment.

As used herein, "identifying a subject in need of treatment" can include the operation of obtaining a biological sample from the subject and determining the level of one or more biomarkers as described herein, assessing a biological sample obtained from the subject, performing an imaging analysis on the subject, assessing one or more clinical characteristics of the subject (e.g., assessing symptoms or overt symptoms), or a combination thereof.

As used herein, the terms "illness," "disease," "condition," "symptom", and "disorder" can be used interchangeably and refer to an abnormality or incorrect functioning of any part, group, or system of a subject's physiology regardless of the causality thereof. For example, a mental illness or emotional disorder can be caused by environmental factors, genetic factors, physiologic events, past experiences, and other influences or combinations thereof.

As used herein, an "acute" condition refers to a condition that can develop rapidly and have distinct symptoms needing urgent or semi-urgent care. By contrast, a "chronic" condition refers to a condition that is typically slower to develop and lingers or otherwise progresses over time. Some examples of acute conditions can include without limitation, an asthma attack, bronchitis, a heart attack, pneumonia, and the like. Some examples of chronic conditions can include without limitation, arthritis, diabetes, hypertension, dyslipidemia, and the like.

The terms "serum levels," "serum amounts", "serum concentrations," "plasma levels," "plasma concentrations," "blood levels," and "blood concentrations" and the like can be used interchangeably herein and refer to the total amount of an identified analyte (e.g., identified metabolite or active agent), including free, bioavailable, and bound fractions in a subject's blood. For example, "serum allopregnanolone" or "serum allopregnanolone levels" or "serum allopregnanolone concentration" or "plasma allopregnanolone concentration" or "allopregnanolone concentration in the blood" refer the total allopregnanolone concentration which is the sum of the allopregnanolone fractions present including substantially free and bound allopregnanolone concentrations. It should be understood that in this written description, such terms provide express support for total analyte or agent levels, as well as for the various applicable fractions thereof, including bioavailable, bound, and substantially free fractions. Unless otherwise specified, these values are "observed" concentrations or amounts without adjusting or correcting for the base-line serum levels in the subject(s). As with any bio-analytical measure, for increased consistency, the method employed to measure initial serum levels should be consistent with the method used to monitor and re-measure serum levels during clinical testing and therapy for a subject. As used herein, the term "$C_{avg}$," refers to an average serum concentration level for time 0 to t (e.g., average daily serum concentration level, daily $C_{avg}$, is calculated as ratio of $AUC_{0-24}$/24 hours) and the term "$C_{max}$," refers to a maximum serum concentration level post single dose administration for the period.

Serum allopregnanolone and its polymorphs measurements based on an immunoassay are not as accurate as a typical radioimmunoassay method (RIA) because the RIA is typically not specific to the target analyte. To measure the target analyte, the assay should be based on chromatography-combined mass spectrometry method (e.g., LC-MS or GC-MS), which can provide reliable data to assess the true PK and pharmacodynamic (PD) potential of allopregnanolone. Consequently, data and results related to oral allopregnanolone and its NAS metabolites are only reliable with respect to levels of NAS or the adequacy of NAS levels for desirable $GABA_A$ receptor modulation when determined by analytical procedures that are amenable to the individual analyte separation step for specificity and accuracy, such as for liquid chromatography (LC), gas chromatography (GC), liquid chromatography-tandem mass spectrometry (LC-MS), or gas chromatography-mass spectrometry (GC-MS).

In one aspect, the PK values (e.g., serum concentrations, computed ratios) of an analyte of interest (e.g., allopregnanolone), derived from the compositions and methods of this invention are based on LC, LC-MS, GC, or GC-MS measurements.

As use herein with respect to physiologic levels of a given substance, the term "baseline" refers to a level or concentration of the substance, such as analyte of interest (e.g., allopregnanolone), in a subject prior to administration of an active agent. For example, the baseline level of allopregnanolone in a subject would be the subject's allopregnanolone serum level prior (e.g., just prior) to the commencement of allopregnanolone administration or therapy.

The term "oral administration" represents any method of administration in which an active agent can be administered by swallowing, chewing, sucking, or drinking of the composition or dosage form. Oral administration can be intended for enteral delivery of an active agent or transmucosal delivery of the active agent. In some embodiments, the composition and dosage forms of the current disclosure can be admixed with food or drink prior to being orally consumed or can be otherwise co-administered with food or a meal.

As used herein, the terms "release" and "release rate" are used interchangeably to refer to the discharge or liberation of a substance, including without limitation a drug, from the composition or dosage form into a surrounding environment such as an aqueous medium either in vitro or in vivo. In another aspect, the term "disintegration" is a physical process related to the mechanical breakdown of a tablet into smaller particles/granules, representing the breakage of inter-particle interactions generated during formation of a tablet by compaction of granulated particles of the active pharmaceutical ingredient (API) and excipients according to <701> Disintegration, USP 43. In another aspect, the term "disintegration" is a physical process related to the opening or rupturing of a capsule. As used herein, the term "disintegration time" refers to an amount of time required to elapse in order for disintegration to occur.

As used herein, a "dosing regimen" or "regimen" such as an "initial dosing regimen" or "starting dose" or a "maintenance dosing regimen" refers to how, when, how much, and for how long a dose of the compositions or dosage forms of the present disclosure can be administered to a subject. For example, an initial or starting dose regimen for a subject may provide for a total daily dose of from about 10 mg to about 3400 mg administered in divided doses at least 4 hours apart with meals repeated daily for 30 days.

As used herein, "daily dose" refers to the amount of allopregnanolone administered to a subject over a 24-hour period of time. The daily dose can be administered one or more administrations during the 24-hour period. In one embodiment, the daily dose provides for two or three or four or six or eight administrations in a 24-hour period. With this in mind, an "initial dose" or initial daily dose" refers to a dose administered during the initial regimen or period of a dosing regimen.

As used herein, an "effective amount" or a "therapeutically effective amount" of a drug refers to a non-toxic, but sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician or by other qualified medical personnel using evaluations known in the art, it is recognized that individual variation and response to treatments may make the achievement of therapeutic effects a somewhat subjective decision. The determination of an effective amount is well within the ordinary skill in the art of pharmaceutical sciences and medicine. See, for example, Meiner and Tonascia, "Clinical Trials: Design, Conduct, and Analysis," *Monographs in Epidemiology and Biostatistics*, Vol. 8 (1986), incorporated herein by reference.

As used herein "single unit" when used to describe dosing of a subject refers to the dosage form being a single dosage form, e.g., a single tablet, capsule, pump or squirt of gel or solution, etc. In contrast, "multiple unit" when used to describe dosing of a subject refers to the dosage including two or more dosage forms, e.g., 2 capsules, 3 tablets, 2-4 pumps or squirts, etc. It is noteworthy that multiple unit dosage forms generally will be the same type of dosage forms (i.e. tablet or capsule) but are not required to be the same dosage form type.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "consisting essentially of" or "consists essentially of" or "essentially consisting" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open-ended term, like "comprising" or "including," in this written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

Occurrences of the phrase "in one embodiment," or "in one aspect," herein do not necessarily all refer to the same embodiment or aspect.

As used herein, comparative terms such as "increased," "decreased," "better," "worse," "higher," "lower," "enhanced," "improved," "maximized," "minimized," and the like refer to a property of a device, component, composition, biologic response, biologic status, or activity that is measurably different from other devices, components, compositions, biologic responses, biologic status, or activities that are in a surrounding or adjacent area, that are similarly situated, that are in a single device or composition or in multiple comparable devices or compositions, that are in a group or class, that are in multiple groups or classes, or as compared to an original (e.g., untreated) or baseline state, or the known state of the art. For example, a composition or dosage form comprising allopregnanolone that "increases" allopregnanolone serum levels or provides an allopregnanolone in a subject that is elevated as compared to a serum level at a previous point in time, such as a baseline level (e.g., prior to treatment), or as compared to an earlier treatment with a different dose (e.g., lower dose). Alternatively, a composition or dosage form that provides an "increased" serum level of allopregnanolone may provide such increase as compared to an alternative known composition or dosage form e.g., compared to an equivalent amount of allopregnanolone utilizing a sub optimal additive or compositions comprising crystalline allopregnanolone or compositions consisting essentially of allopregnanolone suspended/dissolved in edible oil such as canola oil or peanut oil or medium chain triglyceride, or compositions consisting essentially of allopregnanolone solubilized/dissolved allopregnanolone in non-encapsulated aqueous cyclodextrin solution or compositions consisting essentially of allopregnanolone suspended in TWEEN-80 when orally administered the subject.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "fully" refers to the complete extent or degree of an action, characteristic, property, state, structure, item, or result.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "GABA" refers to gamma aminobutyric acid (see the Wikipedia entry for "GABA" such as may be found at: https:en.wikipedia.org/wiki/Gamma-Aminobutyric_acid).

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range, or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

DESCRIPTION

Reference will now be made in detail to preferred invention embodiments. While the embodiments will be described with particularity, the present disclosure is not limited to such embodiments. To the contrary, it is intended to cover alternatives, variants, modifications, and equivalents as may be included within the spirit and scope of the disclosure.

Drawings presented herein are for illustrative purposes only and are not meant to be actual views of any particular oral pharmaceutical composition. Variations in the shapes and profiles depicted in the drawings as a result, for example, of subject variability and/or multicompartmental bioavailability behavior are to be expected. Thus, embodiments described herein are not to be construed as being limited to the particular shapes or profiles as illustrated, but include deviations in shapes that result, for example, from subject variability. For example, a PK curve that is illustrated as a smooth single compartment model curve, may include at least one of subject variability in the PK profile and multiple compartment response. Thus, profiles illustrated in the figures are illustrative in nature, and their shapes are not intended to illustrate the precise shape of a region and do not limit the scope of the present claims. As no scale is presented with the drawings, the drawings are not necessarily to scale.

An initial overview of technology embodiments is provided below, and then specific technology embodiments are described in further detail later. This initial summary is intended to aid readers in understanding the technology more quickly but is not intended to identify key features or essential features of the technology nor is it intended to limit the scope of the claimed subject matter.

Some of the neuro-modulatory and protective effects of allopregnanolone can produce anti-inflammatory, anticonvulsant, antidepressant, anxiolytic, and neuroprotective effects in experimental animals as well as in tissues and cell cultures.

Some efforts have been made to improve bioavailability of allopregnanolone upon oral administration. However, there have been no compositions or methods of administration directed towards providing desirable levels of GABA A receptor modulators post oral administration for therapeutic utility, especially for higher and faster levels of serum allopregnanolone. The compositions and methods in the prior art have used components that could result in insufficient levels of serum allopregnanolone when orally administered to the subject or that have been formulated with crystalline allopregnanolone suspended/dissolved in edible oil, such as canola oil or peanut oil or medium chain triglyceride, allopregnanolone solubilized/dissolved in cyclodextrin solution, or crystalline allopregnanolone suspended in TWEEN-80 with deficient characteristics when orally administered the subject.

In some aspects, the compositions and methods of this invention is intended to treat a CNS disorder comprising at least one of sleep disorders (e.g., insomnia), mood disorders (e.g., depression such as PND, major depressive disorder, postpartum depression, essential tremors, treatment resistant depression, or perinatal depression), dysthymic disorder (e.g., mild depression), bipolar disorder (e.g., "i" and/or II), anxiety disorders (e.g., generalized anxiety disorder (GAD), social anxiety disorder), stress, post-traumatic stress disorder (PTSD), compulsive disorders (e.g., obsessive compulsive disorder (OCD)), schizophrenia spectrum disorders (e.g., schizophrenia, schizoaffective disorder), convulsive disorders (e.g., epilepsy, status epilepticus (SE)), seizures), disorders of memory and/or cognition (e.g., attention disorders, attention deficit hyperactivity disorder (ADHD)), dementia (e.g., Alzheimer's type dementia, Lewis body type dementia, vascular type dementia), movement disorders (e.g., Huntington's disease, Parkinson's disease), personality disorders (e.g., anti-social personality disorder, obsessive compulsive personality disorder), autism spectrum disorders (ASD) (e.g., autism, monogenetic causes of autism such as synaptopathy (see the Wikipedia entry for "synaptopathy" such as may be found at: https://en.wikipedia.org/wiki/Synaptopathy), a Rett syndrome, Fragile X syndrome, Angelman syndrome), pain (e.g., neuropathic pain, injury related pain syndromes, acute pain, chronic pain), traumatic brain injury (TBI), vascular diseases (e.g., stroke, ischemia, vascular malformations), substance abuse disorders and/or withdrawal syndromes (e.g., addition to opiates, cocaine, and/or alcohol), and tinnitus.

In one embodiment, allopregnanolone compositions and oral dosage forms can be formulated to provide blood levels or peak blood levels of allopregnanolone, that are therapeutically effective for treating a CNS disorder when orally administered to a subject. For example, in one aspect, the compositions and oral dosage forms can include a plurality of pharmaceutically acceptable additives that provide serum allopregnanolone in an amount/level sufficient to treat a CNS disorder when orally administered to a subject.

In one aspect, the analyte serum levels are measured using a LC, LC-MS, GC, or GC-MS bioanalytical method.

In one embodiment, an oral pharmaceutical composition comprising allopregnanolone and a plurality of additives wherein oral administration of the composition to a subject having at least one neuropsychiatric and neurodegenerative disorder results in a serum level of the allopregnanolone in the subject such that the at least one neuropsychiatric and neurodegenerative disorder is substantially eliminated, improved, or reduced.

In one embodiment, an oral pharmaceutical composition comprising allopregnanolone and a plurality of pharmaceutically acceptable additives, wherein when composition is orally administered to a subject, the composition provides in the subject at least one of a serum $C_{max}$ level of allopregnanolone and a serum $C_{avg}$ level of allopregnanolone that is greater than serum levels provided by administration of a substantially equivalent amount of allopregnanolone in composition consisting essentially of non-encapsulated SBE-β-CD aqueous solution (cyclodextrin solution administration).

In one embodiment, an oral pharmaceutical composition comprising allopregnanolone and a plurality of pharmaceutically acceptable additives, wherein when composition is orally administered in fasting state to a subject, the composition provides in the subject at least one of a serum $C_{max}$ or dose normalized $C_{max}$ level of allopregnanolone and/or a serum $C_{avg}$ or dose normalized $C_{avg}$. level of allopregnanolone that is greater than serum levels provided by administration of a substantially equivalent amount of allopregnanolone in composition consisting essentially of non-encapsulated SBE-β-CD aqueous solution (cyclodextrin solution administration).

In one embodiment, an oral pharmaceutical composition comprising allopregnanolone and a plurality of pharmaceutically acceptable additives, wherein when composition is orally administered with food to a subject, the composition provides in the subject at least one of a serum $C_{max}$ or dose normalized $C_{max}$ level of allopregnanolone and/or a serum $C_{avg}$ or dose normalized $C_{avg}$. level of allopregnanolone that is greater than serum levels provided by administration of a substantially equivalent amount of allopregnanolone in composition consisting essentially of non-encapsulated SBE-β-CD aqueous solution (cyclodextrin solution administration).

In one embodiment, an oral pharmaceutical composition comprising allopregnanolone and a plurality of pharmaceutically acceptable additives, wherein when composition is orally administered without regard to meal/food to a subject, the composition provides in the subject at least one of a serum $C_{max}$ level or dose normalized $C_{max}$ of allopregnanolone and/or a serum $C_{avg}$ or dose normalized $C_{avg}$ level of allopregnanolone that is greater than serum levels provided by administration of a substantially equivalent amount of allopregnanolone in composition consisting essentially of non-encapsulated SBE-β-CD aqueous solution (cyclodextrin solution administration).

In another embodiment, an oral pharmaceutical composition comprising allopregnanolone and a plurality of pharmaceutically acceptable additives, wherein when composition is orally administered to a subject, the composition provides in the subject at least one of a serum $C_{max}$ level of allopregnanolone and a serum $C_{avg}$ level of allopregnanolone that is greater than serum levels provided by administration of a substantially equivalent amount of allopregnanolone in composition consisting essentially of medium chain triglyceride solution (MCT administration).

In yet another embodiment, an oral pharmaceutical composition comprising allopregnanolone and a plurality of pharmaceutically acceptable additives, wherein when composition is orally administered to a subject, the composition is expected to provide in the subject at least one of a serum $C_{max}$ level of allopregnanolone, a serum $C_{avg}$ level of allopregnanolone that is greater than serum levels provided by administration of a substantially equivalent amount of allopregnanolone in composition consisting essentially of polysorbate-80 suspension (polysorbate 80 administration).

In yet another embodiment, an oral pharmaceutical composition comprising allopregnanolone and a plurality of pharmaceutically acceptable additives, wherein when composition is orally administered to a subject, the composition is expected to provide in the subject at least one of a serum $C_{max}$ level of allopregnanolone, a serum $C_{avg}$ level of allopregnanolone that is greater than serum levels provided by administration of a substantially equivalent amount of allopregnanolone one in in composition consisting essentially of canola oil or peanut oil (edible oil administration).

In one embodiment, allopregnanolone compositions or oral dosage forms or methods can be formulated to efficiently provide expected serum levels of allopregnanolone that are therapeutically effective for treating a CNS disorder when orally administered to a subject. In another aspect, allopregnanolone can be in a form that maximizes serum levels of allopregnanolone when orally administered to a subject. In another aspect, allopregnanolone can be in a form that, when orally administered to a subject, increases serum levels of allopregnanolone. In another aspect, compositions and methods of this invention, when orally administered to a subject, increase serum levels of allopregnanolone as compared to a composition comprising an equivalent amount of treated crystalline (micronized) forms consisting essentially of allopregnanolone suspended in edible oil when orally administered the subject.

In one embodiment, a composition of this invention can be formulated as an oral dosage form that has from about 10 mg to about 600 mg of allopregnanolone. In one aspect, the oral dosage form can be a liquid, a semi-liquid, a semi solid, a sprinkle, an emulsion, a dispersion, a granule, a syrup, a suspension, a capsule, a tablet, a chew, or a drink.

In yet another embodiment, dosage regiments and methods of treating a CNS disorder in a subject are provided and can include orally administering a composition comprising a therapeutically effective amount of allopregnanolone.

In one embodiment, the compositions and oral dosage forms can include a plurality of pharmaceutically acceptable additives, wherein the additives comprise at least one of alpha-tocopherol, sterol, glyceryl monocaprylate, propylene glycol monolaurate, PEG-35 hydrogenated castor oil, PEG-40 hydrogenated castor oil, poloxamer, and a combination thereof that provides adequate levels of allopregnanolone in an amount sufficient to treat a CNS disorder when orally administered to a subject.

In one aspect, the therapeutically effective amount of allopregnanolone can provide a serum level (e.g., average serum levels: $C_{avg}$ or peak serum levels: $C_{max}$) of allopregnanolone that is sufficient to treat the CNS disorder. In another aspect, the therapeutically effective amount of allopregnanolone in a composition can be in a form that provides a therapeutically effective serum level of allopregnanolone post oral administration for treating the CNS disorder in the subject. In a further aspect, the allopregnanolone in a composition disclosed herein may be in a treated form with a plurality of additives that may include at least one surfactant that provides therapeutically effective levels of allopregnanolone effective to treat a CNS disorder in a subject. In yet another aspect, the allopregnanolone can be combined with a plurality of additives that are sufficient to provide a therapeutically effective serum level of allopregnanolone post oral administration thereof for treating the CNS disorder in the subject.

In yet another embodiment, dosage regiments and methods of treating a CNS disorder in a female in this invention comprise an infant female, a female less than age of 5 years, a female in age of 5-18 years, a non-pregnant childbearing age female (e.g., in age of 15-45 years), a pregnant female, a female who has delivered within at least one of one month, six months, and twelve months, a perimenopausal female (e.g., in age of 45-50 years), or postmenopausal female.

Compositions

As previously discussed, when the prior-art compositions were orally administered to the subject by utilizing a composition or dosage form or a plurality of additives or method consisting essentially of solubilized allopregnanolone in a non-encapsulated SBE-β-CD aqueous solution, crystalline allopregnanolone suspension in polysorbate 80, solubilized allopregnanolone in edible oil (e.g., medium chain triglyceride or canola oil or peanut oil), or crystalline allopregnanolone suspension in edible oil, the reported post-administration serum levels of allopregnanolone at studied doses is not expected to result in adequate levels of allopregnanolone to effectively treat CNS disorders. In addition, the oral allopregnanolone administration with those compositions could result inconsistent PD effects. Therefore, an enhanced oral compositions and methods of treating CNS disorders would be needed.

In one embodiment, an oral pharmaceutical composition of this invention can include a therapeutically effective amount of allopregnanolone and a plurality of pharmaceutically acceptable additives that is expected to provide sufficient serum levels of allopregnanolone to treat a CNS depression disorder when orally administered to a subject. In some aspects, the additives can improve, maximize, speed, or otherwise enable or impact effective absorption or bioavailability of allopregnanolone from the composition when administered to a subject. In some aspects, the additives can impact release/absorption amount of the allopregnanolone when administered to a subject or upon in vitro testing. In some aspects, the additives can impact solubilization/absorption of allopregnanolone when administered to a subject or upon in vitro testing. In some aspects, the additives can impact release rate and/or amount of the allopregnanolone when administered to a subject or upon in vitro testing. In some aspects, the additives may improve solubilization of allopregnanolone when administered to a subject or upon in vitro testing. In some aspects, the additives, ingredients, shape and/or size of the dosage form (e.g., tablet or capsule) of the composition may decrease the disintegration time upon in vitro testing of the dosage form such as to 25 minutes or less.

In some aspects, the form of allopregnanolone in the composition can impact release amounts of the allopregnanolone when administered to a subject or upon in vitro testing. In some aspects, the form of allopregnanolone in the composition can impact solubilization of allopregnanolone when administered to a subject or upon in vitro testing. In some aspects, the physical form of allopregnanolone in the composition can impact release rate and/or amount of allopregnanolone when administered to a subject or upon in vitro testing.

When utilizing sulfobutylether-β-cyclodextrin (SBE-β-CD) oral compositions including solubilized allopregnanolone, it may be challenging to load proper amounts of allopregnanolone so as to deliver effective serum levels of allopregnanolone due to limitations with respect to allopregnanolone solubility in various cyclodextrin solutions including SBE-β-CD (e.g., ~6 mg/ml of allopregnanolone solubility in 24% w/v non-encapsulated SBE-β-CD solution). The solubilized fraction of allopregnanolone began to decline, as observed by precipitation, when allopregnanolone concentration was above 8 mg/ml. The amount of allopregnanolone in the cyclodextrin solution can only be enabled by up to about 0.6% w/w loading amount of the composition fill. Moreover, high cyclodextrin amounts required to solubilize allopregnanolone also present safety concerns. In some aspects, the compositions and dosage forms of this invention can comprise higher allopregnanolone loading amounts (>5 mg/ml or 5 mg/g) than ones formulated in non-encapsulated SBE-β-CD or any cyclodextrin solution composition.

In some aspects, the compositions and dosage forms of this invention comprise allopregnanolone loading amounts of at least greater than 0.6% w/w or 1% w/w when fully solubilized in the composition Yet in another aspect, the compositions in accordance with the present invention in immediate release composition and can release greater than about 30 mg or at least 50% of allopregnanolone after 30 minutes when measured using a USP Type II dissolution apparatus in 900 mL of deionized water with 0.5% (w/v) of sodium lauryl sulfate at 75 rpm at 37° C. In another aspect, the compositions in accordance with the present invention can release greater than about 20 mg or at least 40% of the allopregnanolone after 15 minutes when measured using a USP Type II dissolution apparatus in 900 mL of deionized water with 0.5% (w/v) of sodium lauryl sulfate at 75 rpm at 37° C. In some aspects, a daily dose or dosing regimen can impact absorption of allopregnanolone, when administered to a subject.

In another aspect, the allopregnanolone in the composition can be in a form that, when orally administered to a subject results in effective serum levels of allopregnanolone in the subject to treat a CNS disorder. In one embodiment, allopregnanolone in the composition can be in a form that increases absorption efficiency as assessed by dose normalized $AUC_{0-24}$ of allopregnanolone as compared absorption efficiency to a composition comprising allopregnanolone in non-encapsulated SBE-β-CD aqueous solution when orally administered to the subject. For example, by orally administering a composition disclosed herein, the absorption efficiency of allopregnanolone in a subject can be increased by at least about 10% to 300% when compared to orally administering a composition comprising an equivalent amount of allopregnanolone in a non-encapsulated SBE-β-CD comprising aqueous solution.

In one aspect, the allopregnanolone in the composition can be in a form that, when orally administered to a subject result in effective serum peak levels of allopregnanolone in the subject to treat a CNS disorder. In one embodiment, allopregnanolone in the composition can be in a form that blood level food sensitivity as assessed by the ratio of $C_{max}$ food: $C_{max\ fasted}$ is between 2.0:1.0 and 1.0:2.0 post single dose administration, preferably as compared food sensitivity to a composition comprising allopregnanolone in non-encapsulated SBE-β-CD comprising aqueous solution when orally administered post single dose to the subject. For example, by orally administering a composition disclosed herein, the food sensitivity of allopregnanolone blood levels in a subject can be decreased by at least about 20% post single dose administration when compared to orally administering a composition comprising an equivalent amount of allopregnanolone in non-encapsulated SBE-β-CD comprising aqueous solution.

The therapeutically effective amount of allopregnanolone can vary in a composition administered to a subject to treat CNS disorders. In one example, the therapeutically effective amount of allopregnanolone can be present in the composition or oral dosage form an amount greater than one or more of: 0.0001 wt %, 0.001 wt %, 0.01 wt %, 0.1 wt %, 0.5 wt %, 1.0 wt %, 2.0 wt %, 5.0 wt %, 10.0 wt %, 15.0 wt %, 20.0 wt %, 30.0 wt %, 40 wt %, 50 wt %, or combinations thereof, of the fill amount. In another example, the therapeutically effective amount of allopregnanolone can be present in an amount of from about 0.0001 wt % to about 10 wt % of the composition or oral dosage form. In another example, the therapeutically effective amount of allopregnanolone can be present in an amount of from about 10 wt % to about 20 wt %. In yet another example, the therapeutically effective amount of allopregnanolone can be present in an amount of from about 20 wt % to about 30 wt %. In further example, the therapeutically effective amount of allopregnanolone can be present in an amount of from about 30 wt % to about 40 wt %. In yet further example, the therapeutically effective amount of allopregnanolone can be present in an amount of from about 40 wt % to about 50 wt %. In another example, the therapeutically effective amount of allopregnanolone can be present in an amount of from 10 wt % to about 40 wt % or 3 wt % to 10 wt %. In one aspect, the compositions and methods of this invention comprise allopregnanolone in at least one form of substantially solubilized, partially solubilized, substantially non-solubilized, substantially crystalline, partially crystalline, substantially non-crystalline, amorphous, solid, a dispersion, and a eutectic mixture that results in efficient absorption.

As used herein, "additive" refers to a pharmaceutical agent that may be capable of fully or partially solubilizing allopregnanolone in the pharmaceutical composition. In one aspect, a wide variety of additives can be used to fully or partially solubilize allopregnanolone in the pharmaceutical composition in order to provide therapeutically effective levels of allopregnanolone for improving CNS disorder.

The therapeutically effective amount of allopregnanolone can be combined with a plurality of pharmaceutically acceptable additives to provide allopregnanolone in an amount sufficient to treat a CNS depression disorder when administered to a subject. In some embodiments, a wide variety of additives can be used to fully or partially solubilize or disperse allopregnanolone in the pharmaceutical composition in order to provide therapeutically effective levels of allopregnanolone for treating a CNS disorder. Examples of suitable additives can include but are not limited to: (i) tocopherol (e.g., vitamin E) or its derivatives; (ii) fatty acids or their salts; (iii) glyceryl fatty acid esters; (iv) PEG glycerides of fatty acid esters; (v) polyglycerol fatty acid esters; (vi) triglycerides; (vii) hydrogenated polyoxyl vegetable oils or glycerides; (viii) propylene glycol fatty acid esters; (ix) edible oils; (x) sterols or its derivatives (e.g. phytosterol esters), (xi) omega oils, such as omega fatty acids, fish oil, flax seed oil, algae oil, and the like, or combinations thereof.

Examples of suitable solubilizers may comprise, but not limited to, tocopherol or its derivatives, fatty acid or its salts, glyceryl fatty acid esters, PEG glycerides of fatty acid esters, polyglycerol fatty acid esters, triglycerides, hydrogenated polyoxyl vegetable oils or glycerides, propylene glycol fatty acid esters, vegetable oils, and sterols or its derivatives.

In one aspect, vitamin E or its derivatives can comprise, but are not limited to: alpha-tocopherol, beta-tocopherol, gamma-tocopherol, delta-tocopherol, tocopherol acetate, tocopherol linoleate, tocopherol succinate, tocotrienols (alpha-, beta-, gamma-, or delta-), tocofersolan or TPGS (PEG derivatives of alpha-tocopherol), the like, or combinations thereof.

In one embodiment, fatty acid or its salts comprise, but not limited to, octanoic acid, capric acid, lauric acid, myristic acid, palmitic acid, stearic acid, oleic acid, linoleic acid, linoelaidic acid, sodium caproate, sodium caprylate, sodium laurate, sodium myristate, sodium palmitate, sodium oleate, sodium stearate, sodium lauryl sulfate, sodium lauryl sarcosinate, sodium dioctyl sulfosuccinate, sodium cholate, and sodium taurocholate.

In another aspect, glyceryl fatty acid esters can comprise, but are not limited to: glyceryl monooleate, glyceryl monoleate/linoleate, glyceryl monolinoleate, glyceryl ricinoloeate, glyceryl monolaurate, glyceryl monopalmitate, glyceryl monostearate, glyceryl mono-/di-oleate, glyceryl palmitate/stearate, glyceryl acetate, glyceryl laurate, glyceryl citrate/lactate/oleate/linoleate, glyceryl caprylate, glyceryl caprylate/caprate, glyceryl dicaprylate/dicaprate, mono-/di-acetylated monoglycerides, glyceryl monostearate, glyceryl dilaurate, glyceryl dioleate, the like, or combinations thereof.

In yet another aspect, PEG glycerides of fatty acid esters can comprise, but are not limited to: PEG fatty acid monoesters, PEG glycerol fatty acid esters, PEG fatty acid diesters, PEG fatty acid mono-/di-ester mixtures, PEG triglycerides of fatty acid esters, the like, or combinations thereof. PEG glycerol fatty acid esters can comprise, but are not limited to: PEG glyceryl laurate, PEG glyceryl laurate, PEG glyceryl caprylate, PEG glyceryl caprate, PEG glyceryl oleate, PEG glyceryl mono-/di-fatty acid ester mixtures, the like, or combinations thereof. PEG fatty acid monoesters can comprise but are not limited to: esters of caprylic acid, capric acid, lauric acid, oleic acid, and stearic acid, the like, or combinations thereof. Examples of the PEG fatty acid monoesters can include PEG (1-100, 200, 300, 400) monocaprylate, PEG (1-100, 200, 300, 400) monocaprate, PEG (1-100, 200, 300, 400) monolaurate, PEG (1-100, 200, 300, 400) monooleate, PEG (1-100, 200, 300, 400) monopalmitate, PEG (1-100, 200, 300, 400) monostearate, and PEG (1-100, 200, 300, 400) monococoate, the like, or combinations thereof. PEG fatty acid diesters can comprise, but are not limited to, PEG (4-32) dicaprylate, PEG (4-32) dicaprate, PEG (4-32) dilaurate, PEG (4-32) dioleate, PEG (4-32) distearate, and PEG (4-32) dipalmitate, the like, or combinations thereof. PEG fatty acid mono-/di-ester mixtures can comprise but are not limited to: PEG caprylate/caprate, PEG mono-/di-caprylate, PEG mono-/di-caprate, PEG mono-/di-laurate, PEG mono-/di-oleate, and PEG mono-/di-stearate the like, or combinations thereof. PEG triglycerides of fatty acid esters can comprise, but are not limited to: lauroyl polyoxylglycerides, stearoyl polyoxylglycerides, oleoyl polyoxyl glycerides, linoleoyl polyoxyl glycerides, lauroyl polyoxyl glycerides, caprylocaproyl polyoxyl glycerides, and behenoyl polyoxylglycerides the like, or combinations thereof.

In a further aspect, polyglycerol fatty acid esters can comprise, but are not limited to: polyglyceryl (2, 3, 4, 6, 10) oleate, polyglyceryl (2, 3, 4, 6, 10) dioleate, polyglyceryl (2, 3, 4, 6, 10) trioleate, polyglyceryl (2, 3, 4, 6, 10) laurate, polyglyceryl (2, 3, 4, 6, 10) dilaurate, polyglyceryl (2, 3, 4, 6, 10) trilaurate, polyglyceryl (2, 3, 4, 6, 10) stearate, polyglyceryl (2, 3, 4, 6, 10) distearate, polyglyceryl (2, 3, 4, 6, 10) tristearate, polyglyceryl (2, 3, 4, 6, 10) mono-/di-oleate, polyglyceryl (3,6,10) caprate, polyglyceryl (3,6,10) dicaprate, polyglyceryl (3,6,10) tricaprate, polyglyceryl (3,6,10) caprylate, polyglyceryl (3,6,10) dicaprylate, polyglyceryl (3,6,10) tricaprylate, polyglyceryl (3,6,10) polystearate, polyglyceryl (3,6,10) polyoleate, polyglyceryl (3,6,10) mono-/di-oleate, polyglyceryl (3,6,10) caprylate, polyglyceryl (3,6,10) polycaprylate, polyglyceryl (3,6,10) caprate, polyglyceryl (3,6,10) polycaprate, and polyglyceryl (3,6,10) caprylate/caprate, the like, or combinations thereof.

In another aspect, triglycerides can comprise, but are not limited to: glyceryl tricaprylate, glyceryl tricaprate, glyceryl tricaprylate/tricaprate, glyceryl tricaprylate/tricaprate/trisuccinate, glyceryl trioleate, glyceryl tristearate, glyceryl trilaurate, medium chain natural oils, the like, or combinations thereof.

In yet another aspect, hydrogenated polyoxyl vegetable oils or glycerides can comprise, but are not limited to: castor oil or hydrogenated castor oil, or an edible vegetable oil such as corn oil, olive oil, peanut oil, palm kernel oil, apricot kernel oil, peppermint oil, coconut oil, sunflower seed oil, or almond oil, the like, or combinations thereof. The polyoxyl group can include glycerol, propylene glycol, ethylene glycol, polyethylene glycol, sorbitol, pentaerythritol, the like, or combinations thereof c Examples of hydrogenated polyoxyl vegetable oils or glycerides can comprise, but are not limited to: PEG-35 castor oil (Incrocas-35, KOLLIPHOR EL, Cremophor EL), PEG-40 hydrogenated castor oil (KOLLIPHOR RH 40, Cremophor RH40), PEG-25 trioleate (TAGATRTO), PEG-60 corn glycerides (CROVOL M70), PEG-60 almond oil (CROVOL A70), PEG-40 palm kernel oil (CROVOL PK70), PEG-50 castor oil (EMALEX C-50), PEG-50 hydrogenated castor oil (EMALEX HC-50), PEG-8 caprylic/capric glycerides (CAPRYLCAPROYL MACROGOL GLYCERIDES), PEG-6 caprylic/capric glycerides (SOFTIGEN 767), PEG-5 hydrogenated castor oil, PEG-7 hydrogenated castor oil, PEG-9 hydrogenated castor oil, PEG-6 corn oil (LABRAFIL M. 2125 CS), PEG-6 almond oil (LABRAFIL M 1966 CS), PEG-6 apricot kernel oil (LABRAFIL M 1944CS), PEG-6 olive oil (LABRAFIL M 1980 CS), PEG-6 peanut oil (LABRAFIL M 1969 CS), PEG-6 hydrogenated palm kernel oil (LABRAFIL M2130 BS), PEG-6 palm kernel oil (LABRAFIL M 2130 CS), PEG-6 triolein (LABRAFIL M 2735 CS), PEG-8 corn oil (LABRAFIL WL 2609 BS), PEG-20 corn glycerides (CROVOL M40), and PEG-20 almond glycerides (CROVOL A40), the like, or combinations thereof.

In one aspect, propylene glycol fatty acid esters can comprise, but are not limited to: propylene glycol monolaurate (Propylene glycol monolaurate FCC), propylene glycol ricinoleate (Propymuls), propylene glycol monooleate (MYVEROL P-O6), propylene glycol dicaprylate/dicaprate (CAPTEX 200), and propylene glycol dioctanoate (CAPTEX 800), propylene glycol monocaprylate (CAPRYOL 90, NIKKOL Sefsol 218), propylene glycol myristate, propylene glycol monostearate, propylene glycol ricinolate, propylene glycol isostearate, propylene glycol caprylate/caprate, propylene glycol dioleate, propylene glycol distearate, propylene glycol dilaurate, propylene glycol dicaprylate, and propylene glycol dicaprate, the like, or combinations thereof.

In another aspect, vegetable oils can comprise, but are not limited to, corn oil, olive oil, peanut oil, coconut oil, peppermint oil, sunflower seed oil, castor oil, safflower oil, borage oil, cottonseed oil, soybean oil, palm kernel oil, apricot kernel oil, almond oil, omega-3 oil, the like, or combinations thereof.

In one aspect, sterols or its derivatives can comprise, but are not limited to: cholesterol, sitosterol, lanosterol, phytosterol, its PEG derivatives, the like, or combinations thereof. In various aspects, sterols or its derivatives can be hydrophilic or lipophilic. Examples of hydrophilic sterols include but are not limited to: lanosterol PEG-24 cholesterol ether (e.g., SOLULAN C-24, AMERCHOL), PEG-30 soya sterol (e.g., NIKKOL BPS-30, from Nikko), PEG-25 phytosterol (e.g., NIKKOL BP SH-25 from Nikko), PEG-30 cholestanol (e.g., NIKKOL DHC, from Nikko). Examples of Lipophilic Sterol Surfactants are Cholesterol, sitosterol, Phytosterol (e.g., GENEROL series from Henkel), PEG-5 soya sterol (e.g., NIKKOL BPS-S, from Nikko), PEG-10 soya sterol (e.g., NIKKOL BPS-10 from Nikko), PEG-20 soya sterol (e.g., NIKKOL BPS-20 from Nikko), the like, or combinations thereof.

In one embodiment, an additive can be a substance that can be added to the pharmaceutical formulation to enhance the release, separation, or dispersion of the particles, or to enhance the dissolution and further absorption of the particles into the body. Examples of additives can include a lipophilic additive when it has an HLB value of 10 or less, or a hydrophilic additive when it has an HLB value of greater than 10.

In one aspect, the pharmaceutically acceptable additive can comprise a hydrophilic additive, a lipophilic additive, or a combination thereof.

For example, lipophilic additives can comprise, but are not limited to: mono-, di-glycerides of fatty acids, reaction mixtures of alcohols or polyalcohols with a variety of natural and/or hydrogenated oils such as PEG-5 hydrogenated castor oil, PEG-7 hydrogenated castor oil, PEG-9 hydrogenated castor oil, PEG-6 corn oil (e.g., LABRAFIL M 2125 CS), PEG-6 almond oil (e.g., LABRAFIL M 1966 CS), PEG-6 apricot kernel oil (e.g., LABRAFIL M 1944 CS), PEG-6 olive oil (e.g., LABRAFIL M 1980 CS), PEG-6 peanut oil (e.g., LABRAFIL M 1969 CS), PEG-6 hydrogenated palm kernel oil (e.g., LABRAFIL M 2130 BS), PEG-6 palm kernel oil (e.g., LABRAFIL M 2130 CS), PEG-6 triolein (e.g., LABRAFIL M 2735 CS), PEG-8 corn oil (e.g., LABRAFIL WL 2609 BS), PEG-20 corn glycerides (e.g., CROVOL M40), PEG-20 almond glycerides (e.g., CROVOL A40), lipophilic polyoxyethylene-polyoxypropylene block co-polymers (e.g., Pluronic L92, L101, L121 etc.), propylene glycol fatty acid esters, such as propylene glycol monolaurate (e.g., Propylene glycol monolaurate FCC), propylene glycol ricinoleate (e.g., Propymuls), propylene glycol monooleate (e.g., MYVEROL P-O6), propylene glycol dicaprylate/dicaprate (e.g., CAPTEX 200), and propylene glycol dioctanoate (e.g., CAPTEX 800), propylene glycol mono-caprylate (e.g., CAPRYOL 90); propylene glycol oleate (e.g., LUTROL OP2000); propylene glycol myristate; propylene glycol mono stearate; propylene glycol hydroxy stearate; propylene glycol ricinoleate; propylene glycol isostearate; propylene glycol mono-oleate; propylene glycol dicaprylate/dicaprate; propylene glycol dioctanoate; propylene glycol caprylate-caprate; propylene glycol dilaurate; propylene glycol distearate; propylene glycol dicaprylate; propylene glycol dicaprate; mixtures of propylene glycol esters and glycerol esters such as mixtures composed of the oleic acid esters of propylene glycol and glycerol (e.g., ARLACEL 186); sterol and sterol derivatives such as cholesterol, sitosterol, phytosterol, phytosterol fatty acid esters, PEG-5 soya sterol, PEG-10 soya sterol, PEG-20 soya sterol, and the like; glyceryl palmitostearate, glyceryl stearate, glyceryl distearate, glyceryl monostearate, or a combination thereof; sorbitan fatty acid esters such as sorbitan monolaurate (e.g., ARLACEL 20), sorbitan monopalmitate (e.g., Span-40), sorbitan monooleate (e.g., Span-80), sorbitan monostearate, and sorbitan tristearate, sorbitan monolaurate, sorbitan monopalmitate, sorbitan monooleate, sorbitan trioleate, sorbitan sesquioleate, sorbitan tristearate, sorbitan monoisostearate, sorbitan sesquistearate, and the like; fatty acids such as capric acid, caprylic acid, oleic acid, linoleic acid, myristic acid, menthol, menthol derivatives, lecithin, phosphatidyl choline, bile salts, and the like, and mixtures thereof. It is important to note that some lipophilic additives may also function as the solubilizer component of the compositions and oral dosage forms. In some cases, an additive for the compositions and oral dosage forms can be a lipophilic surfactant.

In one embodiment, the pharmaceutically acceptable additive may be free of polysorbate 80. In another embodiment, the pharmaceutically acceptable additive may be free of cyclodextrin. In a further embodiment, the pharmaceutically acceptable additive may be free of edible oil.

The pharmaceutically acceptable additive can also comprise a hydrophilic additive. In one aspect, the hydrophilic additive can comprise without limitation, non-ionic surfactants, ionic surfactants, zwitterionic surfactants, the like, or combinations thereof. Suitable hydrophilic surfactants can include but are not limited to: alcohol-oil transesterification products; polyoxyethylene hydrogenated vegetable oils; polyoxyethylene vegetable oils; alkyl sulphate salts, dioctyl sulfosuccinate salts; polyethylene glycol fatty acids esters; polyethylene glycol fatty acids mono- and di-ester mixtures; polysorbates, polyethylene glycol derivatives of tocopherol, the like, or combinations thereof. Two or more hydrophilic additives from the same or different classes can be referred to as the hydrophilic surfactant unless explicitly specified. In one aspect, non-limiting examples of hydrophilic surfactants can comprise PEG-8 caprylic/capric glycerides, lauroyl macrogol-32 glyceride, stearoyl macrogol glyceride, PEG-40 hydrogenated castor oil, PEG-35 castor oil, sodium lauryl sulfate, sodium dioctyl sulfosuccinate, polyethylene glycol fatty acids mono- and di-ester mixtures, polysorbate 80, polysorbate 20, polyethylene glycol 1000 tocopherol succinate, phytosterols, phytosterol fatty acid esters, poloxamers, and the like, or combinations thereof. In some cases, a hydrophilic additive for the compositions and oral dosage forms can be a hydrophilic surfactant.

In one embodiment, the pharmaceutically acceptable additives can be combined with or otherwise include additives in various amount ranges. For example, the lipophilic additive and hydrophilic additive can be present in amounts such that the ratio of amount (wt %) of lipophilic additive to amount (wt %) of hydrophilic additive is greater than about 2:1. In another aspect, the lipophilic additive and hydrophilic additive can be present in amounts such that the ratio of amount (wt %) of lipophilic additive to amount (wt %) of hydrophilic additive is greater than about 2.5:1. In another aspect, the lipophilic additive and hydrophilic additive can be present in amounts such that the ratio of amount (wt %) of lipophilic additive to amount (wt %) of hydrophilic additive is greater than about 3.5:1. In still another aspect, the lipophilic additive and hydrophilic additive can be present in amounts such that the ratio of amount (wt %) of lipophilic additive to amount (wt %) of hydrophilic additive is at least about 6.5:1.

In one embodiment, the compositions and oral dosage forms can include a plurality of pharmaceutically acceptable additives comprising at least one of alpha-tocopherol, glyceryl monocaprylate, propylene glycol monolaurate, PEG-35 hydrogenated castor oil, PEG-40 hydrogenated castor oil, poloxamer, and a combination thereof that provides adequate levels of allopregnanolone in an amount sufficient to treat a CNS disorder when orally administered to a subject.

In certain examples, the lipophilic additive can make up about 0.6% w/w to about 95% w/w, about 5% w/w to about 70% w/w, about 10% w/w to about 60% w/w, about 15% w/w to about 55% w/w, about 20% w/w to about 50% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, or about 95% w/w of any pharmaceutical composition described herein. In some examples, the hydrophilic additive can make up about 1% w/w to about 50% w/w, about 5% w/w to about 45% w/w, about 10% w/w to about 40% w/w, about 15% w/w to about 35% w/w, about 20% w/w to about 30% w/w, about 5% w/w, about 6% w/w, about 7% w/w, about 8% w/w, about 10% w/w, about 15% w/w, about 20% w/w, about 25% w/w, about 30% w/w, about 35% w/w, about 40% w/w, about 45% w/w, or about 50% w/w of any pharmaceutical composition described herein.

In certain examples, the additive can be a surfactant; The surfactant in the present invention may be any compound containing polar or charged hydrophilic moieties as well as non-polar hydrophobic (lipophilic) moieties; i.e. a surfactant compound must be amphiphilic. Within the context of the present invention, the hydrophilic surfactant can be any hydrophilic surfactant suitable for use in pharmaceutical compositions. Such surfactants can be anionic, cationic, zwitterionic or non-ionic. Mixtures of hydrophilic surfactants are also within the scope of the invention. Similarly, the hydrophobic surfactant can be any hydrophobic surfactant suitable for use in pharmaceutical compositions. Mixtures of hydrophobic surfactants are also within the scope of the invention. Generally, suitable hydrophilic surfactants will have an HLB value greater than about 10 and suitable hydrophobic surfactants will have an HLB value less than about 10. The choice of specific hydrophobic and hydrophilic surfactants should be made keeping in mind the particular hydrophobic therapeutic agent to be used in the composition, and the range of polarity appropriate for the chosen therapeutic agent. With these general principles in mind, a very broad range of surfactants is suitable for use in the present invention.

In one embodiment, the pharmaceutically acceptable additive can optionally include at least one surfactant. When present, the surfactant can comprise about 0.5 wt % to about 50 wt % of the oral solid dosage form. In one embodiment, the surfactant can comprise about 2 wt % to about 40 wt % of the oral solid dosage form. In one embodiment, the surfactant can comprise about 5 wt % to about 30 wt % of the oral solid dosage form. In one embodiment, the surfactant can be a hydrophilic surfactant. A hydrophilic surfactant has a surface active property and that has an HLB value of 10 or more. The hydrophilic surfactants can be an anionic or non-ionic surfactant. Non-limiting examples of hydrophilic surfactants that can be included in the oral solid dosage forms include at least one or a combination of sodium lauryl sulphate, polysorbates, sodium docusate, poloxamers, polyoxyl castor oils, polyoxyl hydrogenated castor oils, lecithin or its derivatives, etc., and mixtures thereof.

Poloxamer represents Polyethylene-Polyoxypropylene Block Copolymer and can be any kind of the following formula: $HO(C_2H_4O)_a(C_3H_6O)_b(C_2H_4O)_aH$, where "a" and "b" denote the number of polyoxyethylene and polyoxypropylene units, respectively. The compounds are listed by generic name, with the corresponding "a" and "b" values. Poloxamer can be represented in a form of $(C_3H_6O)_b(C_2H_4O)_aH$ (HLB)), such as (Poloxamer 105 (a=11, b=16 (8))); (Poloxamer 108 (a=46, b=16 (>10))); (Poloxamer 122 (a=5, b=21 (3))); (Poloxamer 123 (a=7, b=21 (7))); (Poloxamer 124 (a=11, b=21 (>7))); (Poloxamer 181 (a=3, b=30)); (Poloxamer 182 (a=8, b=30 (2)); (Poloxamer 183 (a=10, b=30)); (Poloxamer 184 (a=13, b=30)); (Poloxamer 185 (a=19, b=30)); (Poloxamer 188 (a=75, b=30 (29))); (Poloxamer 212 (a=8, b=35)); (Poloxamer 215 (a=24, b=35)); (Poloxamer 217 (a=52, b=35)); (Poloxamer 231 (a=16, b=39)); (Poloxamer 234 (a=22, b=39)); (Poloxamer 235 (a=27, b=39)); (Poloxamer 237 (a=62, b=39 (24))); (Poloxamer 238 (a=97, b=39)); (Poloxamer 282 (a=10, b=47)); (Poloxamer 284 (a=21, b=47)); (Poloxamer 288 (a=122, b=47 (>10)); (Poloxamer 331 (a=7, b=54 (0.5)); (Poloxamer 333 (a=20, b=54)); (Poloxamer 334 (a=31, b=54)); (Poloxamer 335 (a=38, b=54)); (Poloxamer 338 (a=128, b=54)); (Poloxamer 401 (a=6, b=67)); (Poloxamer 402 (a=13, b=67)); (Poloxamer 403 (a=21, b=67)); (Poloxamer 407 (a=98, b=67)); and combinations thereof.

In one embodiment, the oral compositions described herein may be free of any modulator that slows the release rate of allopregnanolone in an aqueous media or in vivo. In an embodiment, the composition may be non-aqueous. In another more specific embodiment, the composition may be encapsulated.

In another embodiment, the composition may include less than 250 mg/ml or mg/g of SBE-β-CD. In another more specific embodiment, the composition may be substantially free of SBE-β-CD.

In another embodiment the composition is a non-aqueous composition filled in a capsule or a tablet dosage form.

In another embodiment, the oral solid dosage form(s) described herein may be free of synchronized release characteristics for allopregnanolone with a solubilizer in an aqueous media so that the dosage form can release more than 90% of allopregnanolone within 4 hours post administration or in vitro testing. Or stated differently, the release of the active agent may not be synchronous with the release of the lipophilic additives. For instance, the release of the active agent may not be at a rate that is similar to the rate of release of the additives.

Other optional ingredients: Although not always necessary, the compositions of the present invention may also include one or more additional components, i.e., functional ingredients. Classes of ingredients that may be present in the compositions, include, but are not limited to, solvents, absorbents, acids, adjuvants, anticaking agent, glidants, antitacking agents, antifoamers, anticoagulants, antimicrobials, antioxidants, antiphlogistics, astringents, antiseptics, bases, binders, chelating agents, sequestrants, coagulants, coating agents, colorants, dyes, pigments, compatiblizers, complexing agents, softeners, crystal growth regulators, denaturants, desiccants, drying agents, dehydrating agents, diluents, dispersants, emollients, emulsifiers, encapsulants, enzymes, fillers, extenders, flavor masking agents, flavorants, fragrances, gelling agents, hardeners, stiffening agents, humectants, lubricants, moisturizers, bufferants, pH control agents, plasticizers, soothing agents, demulcents, retarding agents, spreading agents, stabilizers, suspending agents, sweeteners, disintegrants, thickening agents, consistency regulators, surfactants, opacifiers, polymers, preservatives, antigellants, rheology control agents, UV absorbers, tonicifiers and viscomodulators. One or more ingredients from any particular class, as well as one or more different classes of ingredients, may be present in the compositions. Specific examples of ingredients are well known in the art.

Other ingredients, preferably for non-solid dosage form, such as co-solvents can partially solubilize allopregnanolone when presented in an effective amount. Examples of suitable co-solvents can comprise without limitation: alcohols and polyols, such as ethanol, propanol, isopropanol, butanol, benzyl alcohol, ethylene glycol, propylene glycol, butanediols, glycerin or its derivatives thereof, glycerol, diglycerol, polyglycerol, pentaerythritol, sorbitol, mannitol, transcutol, dimethyl isosorbide, triacetin, trimethyl citrate, polyethylene glycol, polypropylene glycol, polyvinylalcohol, hydroxypropyl methylcellulose and other cellulose derivatives, cyclodextrins or its derivatives, the like, or combinations thereof.

In one embodiment, the allopregnanolone in the composition can comprise a crystalline form that is grinded, sieved, milled, nanosized, micronized, ultra-micronized, the like, or combinations thereof. In one aspect, a specified weight percentage of the allopregnanolone in the additive can be in a non-crystalline form (e.g., amorphous solid, a solution, an emulsion, a liquid, a semi-liquid, or the like). In one example, at least about 50% of the allopregnanolone in the additive can be in a non-crystalline state. In another example, at least about 65% of the allopregnanolone in the additive can be in a non-crystalline state. In yet another example, at least about 80% of the allopregnanolone in the additive can be in a non-crystalline state. In another example, at least about 95% of the allopregnanolone in the additive can be in a non-crystalline state.

In one embodiment, oral compositions disclosed herein may comprise substantially treated crystalline solid forms of allopregnanolone with a plurality of additives including at least one surfactant. In one aspect the said treated allopregnanolone form can be the starting or prior to formulating form or post formulation/processing of the composition. More specifically, crystalline solid forms of allopregnanolone may include at least one polymorph of allopregnanolone.

As used herein, the term "treated" may be applied to either crystalline forms of the active agent or to non-crystalline forms of the active agent. Further as used herein, where applied to crystalline forms of the active agent, the term "treated" means having been subjected to processing as exemplified by the active agent processed into an active agent in the form of at least one of grinded, sieved, milled, micronized, and nanosized, and where applied to non-crystalline forms of the active agent, the term "treated" is exemplified by the active agent processed into an active agent in the form of at least one of amorphous and fully solubilized. As used herein, the term "untreated" is defined as raw ("as is") or unprocessed active agent as exemplified by non-micronized or non-milled. This treatment of reducing particle sizes of the active agent helps in improving the release rate, absorption rate, and bioavailability of the active agent. In one example, the original powder of allopregnanolone to be used in the compositions of this invention is treated, such as grinded, sieved, milled, micronized, nanosized, amorphous, or fully solubilized before formulating in the compositions. Further for example, a "micronized" treatment may provide approximately the particle size distribution of allopregnanolone ranging over D50=~6 μm and D90=~20 μm. Further still for example, a "nanosized" treatment may provide approximately the particle size distribution of allopregnanolone ranging over D50=~150 nm and D90=~300 nm. D10, D50 and D90 are defined as follows: D10=10% of the population of particles in a composition have a size that lies below a designated value. D50=50% of the population of particles in a composition have a size that lies below a designated value. D90=90% of the population of particles in a composition have a size that lies below a designated value.

In one embodiment, the particle size distribution of the treated crystalline form of allopregnanolone in this invention may range from D90=about or less than 250 nm to about or less than 250 μm. In one aspect, the particle size distribution of the treated allopregnanolone crystalline forms in this invention may be D90=less than about or less than 250 μm, such as one of D90=about or less than 250 nm, D90=about or less than 300 nm, D90=about or less than 350 nm, D90=about or less than 400 nm, D90=about or less than 500 nm, D90=about or less than 750 nm, D90=about or less than 1 μm, D90=about or less than 2 μm, D90=about or less than 5 μm, D90=about or less than 10 μm, D90=about or less than 15 μm, D90=about or less than 20 μm, D90=about or less than 30 μm, D90=about or less than 40 μm, D90=about or less than 50 μm, D90=about or less than 75 μm, D90=about or less than 100 μm, D90=about or less than 150 μm, D90=about or less than 200 μm, D90=about or less than 250 μm, and any D90 size between the above values. In another embodiment, the particle size distribution of the treated crystalline form of allopregnanolone in this invention may be D90=less than about 75 μm.

In one embodiment, the particle size distribution of the treated crystalline form of allopregnanolone in this invention may range from D50=about 150 nm to about 100 μm. In one aspect, the particle size distribution of the treated allopregnanolone crystalline forms in this invention may be D50=less than about 100 μm, such as one of D50=about 100 nm, D50=about 150 nm, D50=about 200 nm, D50=about 250 nm, D50=about 300 nm, D50=about 350 nm, D50=about 400 nm, D50=about 500 nm, D50=about 750 nm, D50=about 1 μm, D50=about 2 μm, D50=about 5 μm, D50=about 10 μm, D50=about 15 μm, D50=about 20 μm, D90=about 30 μm, D50=about 40 μm, D50=about 50 μm, D50=about 75 μm, D50=about 100 μm, and any D50 size between the above values.

In another embodiment, the particle size distribution of the treated crystalline form of allopregnanolone in this invention may be D50=any size between about 150 nm and about 50 μm.

In one embodiment, the particle size distribution of the treated crystalline form of allopregnanolone in this invention may range from D10=about 50 nm to about 50 μm. In one aspect, the particle size distribution of the treated allopregnanolone crystalline forms in this invention may be D10=less than about 50 μm, such as one of D10=about 50 nm, D10=about 100 nm, D10=about 150 nm, D10=about 200 nm, D10=about 250 nm, D10=about 300 nm, D10=about 350 nm, D10=about 400 nm, D10=about 500 nm, D10=about 750 nm, D10=about 1 μm, D10=about 2 μm, D10=about 5 μm, D10=about 10 μm, D10=about 15 μm, D10=about 20 μm, D10=about 25 μm, D10=about 40 μm, D10=about 50 μm, and any D10 size between the above values. In another embodiment, the particle size distribution of the treated crystalline form of allopregnanolone in this invention may be D10=less than about 20 μm.

In another embodiment, an oral pharmaceutical composition or oral dosage form can include an amount of allopregnanolone that provides desirable $GABA_A$ receptor binding efficiency to effectively treat CNS disorders when administered to a subject. For example, in one embodiment, the composition or oral dosage form can include a plurality of pharmaceutically acceptable additives that improves or otherwise accelerates absorption of allopregnanolone when administered to a subject.

Dosage Forms and Dosing Regimens

In one embodiment, the composition can be formulated as an oral dosage form. The oral dosage form can be a member selected from the group consisting of: a liquid, a semi-liquid, a semi solid, a sprinkle, an emulsion, a dispersion, a granule, a syrup, a suspension, a capsule, a tablet, a chew, or a drink the like, or combinations thereof. In one aspect, the composition can be formulated as an oral dosage form that has from about 10 mg to about 600 mg of allopregnanolone. In another aspect, the composition can be formulated as an oral dosage form that has from about 10 mg to about 600 mg of allopregnanolone that when orally administered to a subject is expected to provide an allopregnanolone $C_{max}$ of greater than about 4 ng/ml regardless of the consumption of a meal when measured using LC-MS or GC-MS.

The oral pharmaceutical composition comprising allopregnanolone can be administered as an oral dosage form, such as solid, liquid, or partially or fully solubilized oral dosage forms, traditionally intended to substantially release and deliver allopregnanolone in the gastrointestinal tract beyond the mouth and/or buccal cavity.

In certain embodiments, the oral pharmaceutical composition comprising allopregnanolone can be administered as solid dosage forms known to the ordinary skill in the art. Examples of solid dosage forms include, but not limited to, two-piece hard gelatin capsules, soft gelatin capsules, beads, beadlets, granules, spherules, pellets, microcapsules, microspheres, nanospheres, nanocapsules, tablets, or combinations thereof.

In certain embodiments, the oral pharmaceutical composition comprising allopregnanolone can be administered as a liquid (e.g., solution, suspension, drink, etc.), or partially or fully solubilized forms in gelatin or non-gelatin capsules known to the ordinary skill in the art. The gelatin capsule can be a soft gelatin capsule or a hard gelatin capsule or any other capsule. The hard gelatin capsule can be a two-piece, standard gelatin capsule which typically includes a first capsule portion of bottom and a second capsule portion of top. The soft gelatin capsule can be a two-piece capsule wherein two portions are sealed together or a one-piece, hermetically sealed capsule.

In certain embodiments, the pharmaceutical composition can be administered to a subject in need of allopregnanolone for treating CNS disorders. In a particular embodiment, the amount of allopregnanolone administered ranges from about 10 mg to about 600 mg, about 30 mg to about 500 mg, about 30 mg to about 400 mg, about 30 mg to about 300 mg, about 30 mg to about 200 mg, about 70 mg to about 400 mg, or about 100 mg to about 560 mg. In certain specific embodiments, the active ingredients are allopregnanolone.

In other embodiments, the allopregnanolone can be administered to a subject (e.g., males and females) in need for the oral pharmaceutical compositions in this disclosure so that the subject in need thereof receives a therapeutically effective amount of allopregnanolone from the oral compositions. In an embodiment, allopregnanolone in the oral compositions ranges from about 10 mg to about 600 mg, such as about 10 mg, 15 mg, 20 mg, 25 mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 350 mg, about 400 mg, about 450 mg, about 500 mg, about 550 mg, about 600 mg, or any amount within the range of the noted values.

In particular embodiments, the amount of allopregnanolone administered per dose from the oral pharmaceutical composition disclosed herein to a subject in need thereof, can range from about 10 mg to 1200 mg, about 10 mg to about 600 mg, about 30 mg to about 500 mg, from about 30 mg to about 400 mg, from about 30 mg to about 300 mg, from about 30 mg to about 200 mg, about 70 mg to about 400 mg, or about 100 mg to about 560 mg. In certain embodiments, the amount of allopregnanolone per dose administered to a subject in need thereof using the oral pharmaceutical composition disclosed herein can be about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 350 mg, about 400 mg, about 450 mg, about 500 mg, about 550 mg, about 600 mg, about 700 mg, about 800 mg, about 900 mg, about 1000 mg, about 1100 mg, about 1200 mg, or any amount within the noted values.

To receive the desired levels of allopregnanolone per dose, the human in need thereof can, in certain embodiments, be administered the oral composition comprising about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 500 mg, about 550 mg, about 600 mg, about 700 mg, about 800 mg, about 900 mg, about 1000 mg, about 1100 mg, about 1200 mg, or any amount within the noted values.

In one embodiment, the amount of allopregnanolone in the composition can range about 0.6 weight percent to about 50 weight percent of the composition. In a further embodiment, a subject in need thereof can be administered the amount of allopregnanolone with about 0.6%, 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 22%, about 24%, about 25%, about 26%, about 28%, about 30%, about 35%, about 40%, about 45%, about 50% weight of the composition, or any percentage within the noted values.

In certain embodiments, the oral pharmaceutical compositions comprising allopregnanolone in this disclosure can be administered once daily within in any of the above noted amounts until the disease or condition is treated. In other embodiments, the oral pharmaceutical compositions in this discloser can be administered twice daily within in any of the above noted amounts until the disease or condition is treated. In yet further embodiments, the oral pharmaceutical compositions in this discloser can be administered equal to or more than three times daily within in any of the above noted amounts until the disease or condition is treated.

The composition can provide a daily dose of varying amounts. In one aspect, the therapeutically effective amount of the allopregnanolone can be orally administered from one time to twelve times per day. In one example, the daily dose of the therapeutically effective amount of the allopregnanolone can comprise from about 10 mg to about 1200 mg, about 10 mg to about 600 mg, about 30 mg to 400 mg, about 70 mg to 400 mg, or about 100 mg to 560 mg. In another example, the daily dose of allopregnanolone can be a fixed dose of from about 10 mg to about 3400 mg. In another example, the daily dose of the allopregnanolone can be a fixed dose of from about 10 mg to about 2500 mg. In another example, the daily dose of the allopregnanolone can be a fixed dose of from about 10 mg to about 1500 mg. In another example, the daily dose of the allopregnanolone can be a fixed dose of from about 10 mg to about 1200 mg. In another example, the daily dose of the allopregnanolone can be a fixed dose of from about 10 mg to about 600 mg. In another example, the daily dose of the allopregnanolone can be a fixed dose of from about 70 mg to about 400 mg. In another example, the daily dose of the allopregnanolone can be a fixed dose of from about 100 mg to about 560 mg. In yet another aspect, a single dose of the allopregnanolone can be administered in a dosage form comprising from 1 to 4 dosage form units. In yet further aspect, a daily dose of the allopregnanolone can be administered in a dosage form comprising from 1 dosage form unit to 20 dosage form units.

In an embodiment, the daily dose of therapeutically effective amount of the allopregnanolone can comprise at least one of about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg about 75, mg about 80, mg about 85, mg about 90 mg about 95 mg, about 100 mg, about 110 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 300 mg, about 400 mg, about 500 mg, about 600 mg, about 700 mg, about 800 mg, about 900 mg, about 1000 mg, about 1100 mg, about 1200 mg, about 1500 mg, about 2000 mg, about 2500 mg, about 3400 mg, or any amount within the noted values.

In other aspect, the allopregnanolone can be administered to a subject (e.g., males and females) to provide a therapeutically effective amount of allopregnanolone. In one example, the allopregnanolone in the oral compositions can have a total daily dose that ranges from about 10 mg to about 3400 mg, such as about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 300 mg, about 400 mg, about 500 mg, about 550 mg, about 600 mg, about 800 mg, about 1,000 mg, about 1,200 mg, about 1,500 mg, about 1,800 mg, about 2,000 mg, about 2,400 mg, about 2,800 mg, about 3,000 mg, about 3,400 mg, or any amount within the noted values.

In one aspect, the number of dosage form units (e.g., capsule, tablet, etc.) of allopregnanolone per dose can range from 1 to 4, from 1 to 3, from 1 to 2 or one dosage form unit per dose.

To receive a target amount of the allopregnanolone per single dose, in some aspects, the subject can be administered allopregnanolone in amounts of from 10 mg to 1200 mg, such as about 10 mg, about 15 mg, about 20 mg, about 25 mg, 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 250 mg, about 300 mg, about 400 mg, about 500 mg, about 550 mg, about 600 mg, about 700 mg, about 800 mg, about 900 mg, about 1000 mg, about 1100 mg, about 1200 mg, or any amount within the noted values.

In one aspect, the therapeutically effective amount of the allopregnanolone can be orally administered once daily in any recited amount until the CNS disease or condition is treated. In one aspect, the oral compositions can be administered in the morning, afternoon, evening, or before bedtime. In another aspect, the oral compositions can be administered at about bedtime or before bedtime by any of about 5 hours, about 4 hours, about 3 hours, about 2 hours, and about 1 hour.

In other aspects, the oral pharmaceutical composition and/or oral dosage forms can be administered twice daily in any of the above noted amounts until the disease or condition is treated. The oral compositions can be administered in the morning and evening, or 12 hours apart. In yet further aspects, the oral pharmaceutical composition or oral dosage form can be administered greater than or equal to three times daily in any of the recited amounts until the disease or condition is treated. The oral compositions or dosage forms can be administered every 8 hours, every 6 hours, every 4 hours, every 3 hours, every 2 hours, or every 1 hour.

In one aspect, the therapeutically effective amount of the allopregnanolone can be orally administered to the subject according to a dosage regimen of at least once per day for a specified duration of from about a single day to about 3 months. In another aspect, the oral pharmaceutical composition can be administered for 1 day, 2 days, 2.5 days, 3 days, 4 days, 5 days, 6 days, 7 days, 8 days, 9 days, 10 days, 12 days, 14 days, 16 days, 18 days, 20 days, 21 days, 22 days, 24 days, 26 days, or 28, or 30 days until the disease or condition is treated. In one aspect, the oral pharmaceutical compositions can be administered for 1 week, 2 weeks, 3 weeks, 4 weeks, or 5 weeks until the disease or condition is treated. In another aspect, the oral pharmaceutical can be administered for 1 month, 2 months, or 3 months until the disease or condition is treated.

In one aspect, the oral pharmaceutical composition or dosage form can be administered with or without titration. In one aspect, the oral pharmaceutical compositions can be up-titrated to 50%, 100%, 150%, 200%, 300%, or 400% more than the initial (pre titration) dose. In another aspect, the oral pharmaceutical compositions can be down-titrated to 90%, 80%, 75%, 67%, 50%, 40%, 33%, or 25% of the initial (pre-titration) dose. In an aspect, the oral pharmaceutical compositions can be administered with the fixed dose or the consistent dose as the initial dose.

In one aspect, the oral pharmaceutical composition or dosage form can be titrated to a subsequent allopregnanolone dose based on a PK or PD response to an initial dose by a subject. In one example, the composition or oral dosage form can be orally administered in an initial allopregnanolone dose of from about 10 mg to about 1200 mg and titrated to a maintenance allopregnanolone dose that is about 25% to about 400% higher than the initial dose or about 10% to about 75% lower than the initial dose. In one example, the allopregnanolone dose can be increased or decreased from about 0.25× to about 4× from an initial allopregnanolone dose to an allopregnanolone maintenance dose.

Achieving desired serum allopregnanolone levels to treat a CNS disorder post oral dosing or appropriate oral dose for efficacy for CNS indications has remained elusive and challenging for numerous reasons. For example, an oral allopregnanolone composition with non-encapsulated aqueous high (250 mg/ml) cyclodextrin comprising solution (e.g., SBE-β-CD) delivering a dose of 30 mg of allopregnanolone has resulted in inefficient oral bioavailability (dose normalized $AUC_{0-24}$ of about less than 0.6 h/L) to produce appreciable therapeutic PD effects at that dose or serum level. Moreover, the rate of absorption, as assessed by $C_{max}$ and time to $C_{max}$ ($T_{max}$) is sensitive to food effects with substantial reported change in PK profile (e.g. $C_{max}$) in fed state.

FIG. 1 is an illustrative plot of a PK profile showing plasma concentration of an orally administered single dose of a drug as a function of time. The PK profile may be used to characterize the absorption/bioavailability of allopregnanolone in a subject's blood over time. The most common PK parameters being $C_{max}$, $T_{max}$ and area under the curve ($AUG_{0-24}$). The plasma concentration observed for a single dose of a drug increases until it reaches a peak concentration, $C_{max}$ as shown in FIG. 1. The time taken to reach the $C_{max}$ is termed $T_{max}$, as shown in FIG. 1. Referring to FIG. 1, the $AUG_{0-24}$ of the drug concentration is the integrated area under the observed curve of the plasma concentration vs. time. The $AUG_{0-24}$ represents the drug exposure in the systemic circulation over a period of time. Unless otherwise stated, measured pharmacokinetic parameters are mean reported values from a group of subjects, the parameter $T_{max}$ is not mean reported, rather it is median reported from a group of subjects.

Compositions or dosage forms may be administered with or without food, such as meal, snacks, appetizers, or drinks.

In one example, administration without food can be during a fasting period of the subject. Oral pharmaceutical compositions may be analyzed for food/meal sensitivity by comparing the ratio of the PK parameter $C_{max}$ or $C_{max/dose}$ for [food]: [fasted]. A near unity ratio for $C_{max}$ post single equidose dose administration would show a lack of food sensitivity for the oral composition, while a high ratio or low ratio (e.g., greater than 2.0 or less than 0.5) would show a food sensitivity for the oral composition.

Figure 2:
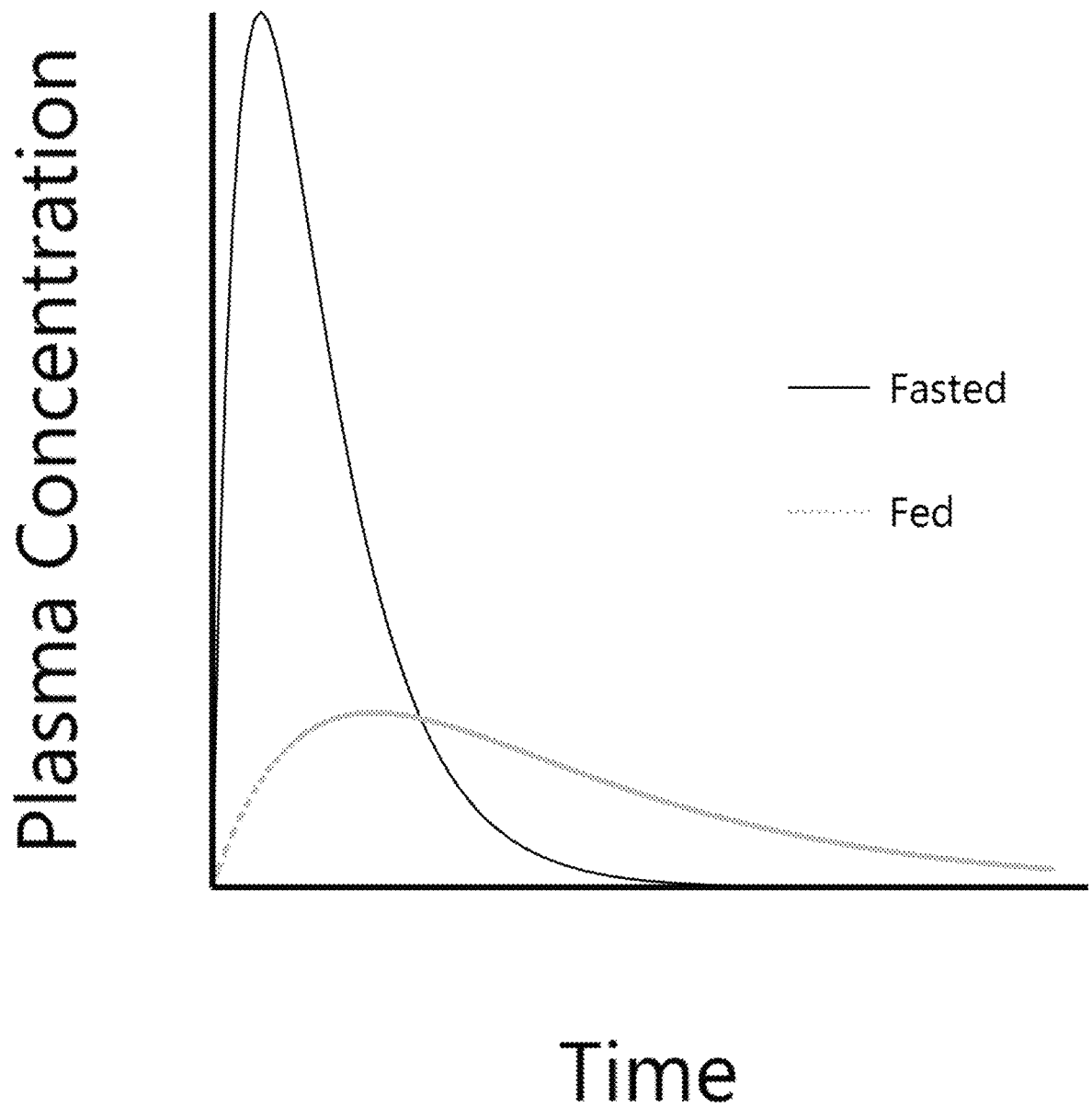
FIG. 2 is a plot of pharmacokinetic profiles of an exemplary embodiment of a drug composition that shows sensitivity to food.

FIG. 2 is an illustrative plot of two simulated single dose PK profiles of an equidose orally administered composition that is administered in a fasted state (labeled Fasted, black solid line) and in a fed state (labeled Fed, grey dotted line). Food sensitivity may be characterized by comparing PK parameters $C_{max}$. The $C_{max}$ ratio between fasted and fed in FIG. 2 is ~1:5 indicating that the first orally administered composition is sensitive to food co-administration.

Figure 3:
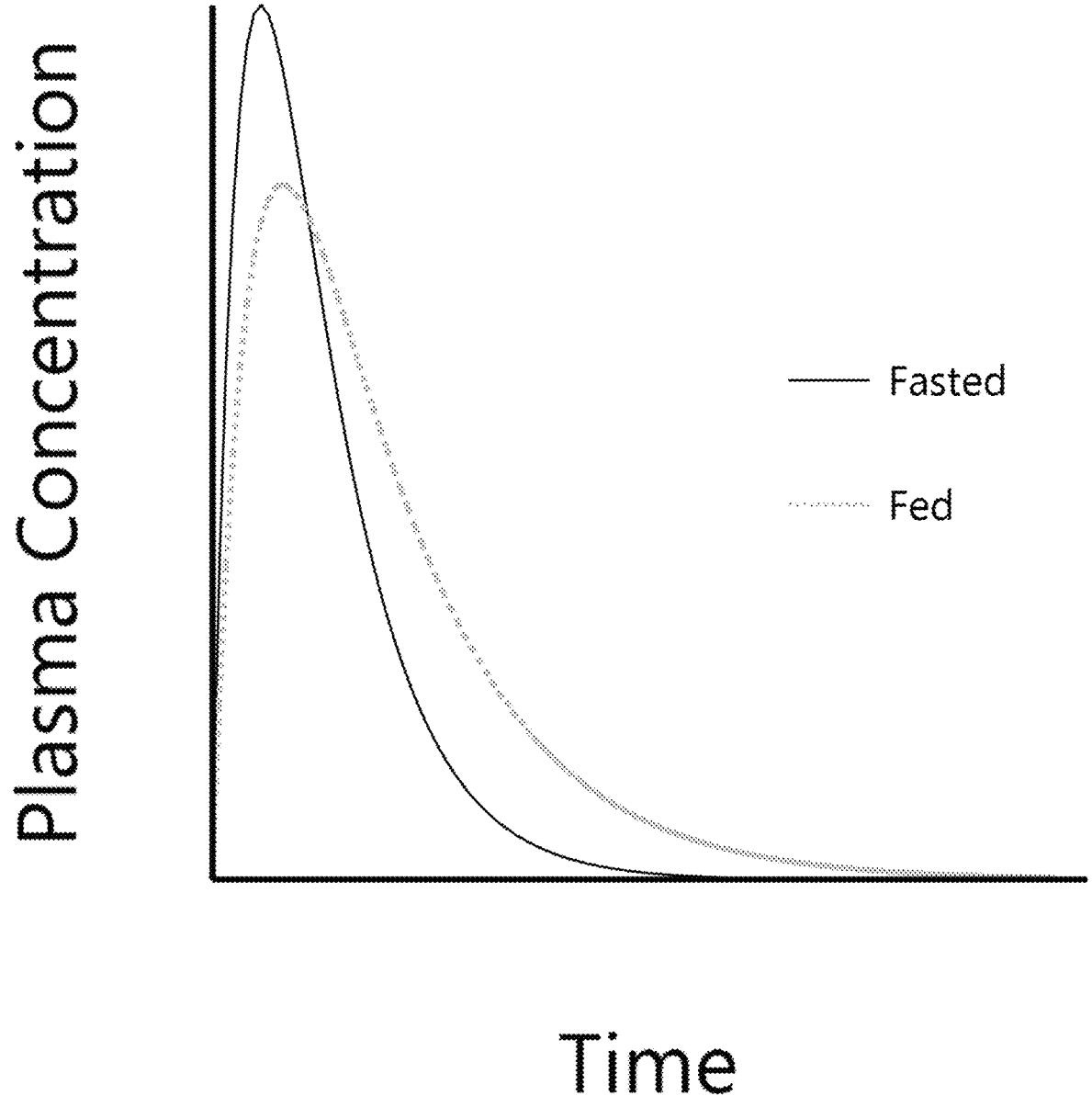
FIG. 3 is a plot of pharmacokinetic profiles of an exemplary embodiment of a drug composition that shows lack of substantial sensitivity to food.

FIG. 3 is an illustrative plot of two simulated single dose PK profiles of a second equidose orally administered composition that is administered in a fasted state (labeled Fasted, black solid line) and in a fed state (labeled Fed, grey dotted line). The $C_{max}$ ratio between fasted and fed in FIG. 3 is ~1:1.25 indicating that the second orally administered composition is not sensitive to food co-administration.

Two orally administered doses may be compared for food sensitivity. For example, the first orally administered dose may be compared for food sensitivity against the second orally administered dose by comparing the $C_{max}$ ratio of each orally administered dose. By way of example, oral pharmaceutical compositions of allopregnanolone in a solution form with cyclodextrin in an aqueous, non-encapsulated composition may be sensitive with regard to food (e.g., [with food]:[fasted]=1:2.2), while surprisingly, oral pharmaceutical compositions of this invention that include allopregnanolone in an encapsulated solubilized form without cyclodextrin (e.g., SBE-β-CD) may be less sensitive with regard to food (e.g., [with food]:[fasted]=1:1.6). Additionally, oral pharmaceutical compositions that comprise allopregnanolone in a treated solid form exhibit low to no food sensitivity and may be administered with no regard to food, (e.g., [with food]:[fasted]=1:1.1). More specifically, oral pharmaceutical compositions that include allopregnanolone in a crystalline form may be administered with no regard to food. More specifically, oral pharmaceutical compositions that include allopregnanolone in the crystalline form may include at least one polymorph. In some embodiments, oral pharmaceutical compositions may be prepared with the ratio [with food]:[fasted] of a PK parameter between 2:1 and 1:2, between 1.75:1 and 1:1.75, 1.5:1 and 1:1.5, 1.25:1 and 1:1.25, or substantially 1:1.

Figure 4:
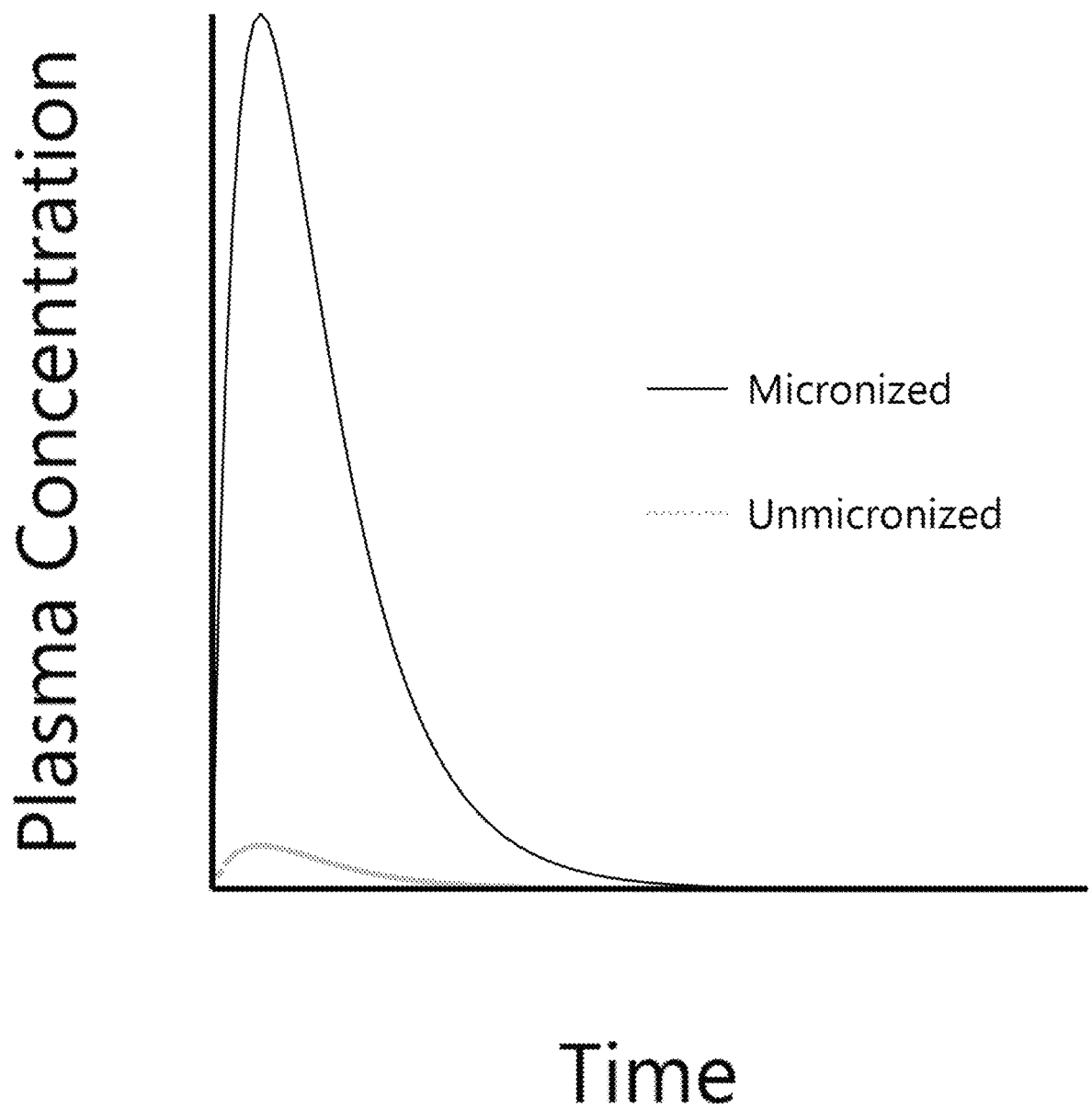
FIG. 4 is a plot of pharmacokinetic profiles of an exemplary embodiment of a drug in two different compositions.

Pharmaceutical composition, may not, on its own be used to determine subject serum drug blood levels. By way of example, referring now to FIG. 4 which is an illustrative plot of two simulated single dose PK profiles of the first orally administered composition comprising treated (e.g., micronized, labeled Micronized, black solid line) allopregnanolone and untreated (e.g., unmicronized, labeled Unmicronized, grey dotted line) allopregnanolone, the first orally administered composition comprising treated allopregnanolone provides superior blood levels (higher $C_{max}$ and $AUC_{0-24}$) than the first orally administered composition comprising untreated allopregnanolone. While FIG. 4 shows an illustrative plot of a treated and untreated embodiment for an active form, a plurality of modulations may provide a similar effect to the serum drug blood levels. By way of additional example, a similar effect may be observed when a pharmaceutical composition (e.g. a 300 mg tablet dosage form) is treated and has composition that includes at least 7.5% surfactant (e.g., Poloxamer 407; w/w %) and a second pharmaceutical composition is substantially similar with the exception of having no or less than 0.5% surfactant. The serum drug blood levels of the sample with 7.5% surfactant and without surfactant is substantially similar to the serum drug blood levels observed in FIG. 4 between the micronized and unmicronized examples. Thus, to achieve target blood levels ($C_{max}$ and $AUC_{0-24}$) and biological sensitivity for a specific orally administered compositions, all conditions for preparing said dosages must be performed.

Thus, allopregnanolone in oral pharmaceutical compositions may be preferably in treated form. More preferably in oral solid compositions (e.g., 300 mg tablet dosage form) comprising allopregnanolone, the allopregnanolone may be in a treated form. The active drug in oral pharmaceutical compositions in solid form that is at least partially crystalline may further include at least one polymorph of the active drug. In some embodiments, the active drug, allopregnanolone is substantially crystalline. In some embodiments, allopregnanolone may be treated as previously described.

By way of example only, a solid dose formulation comprising treated allopregnanolone may show a food sensitivity ratio [with food]:[fasted] that is selected to be between 2:1 and 1:2, between 1.75:1 and 1:1.75, between about 1.5:1 and 1:1.5, between about 1.25:1 and 1:1.25, between about 1.1:1 and 1:1.1, or substantially 1:1.

Thus, there remains an unmet need for compositions and methods that enable generation of higher, faster, more reliable, and adequate serum levels of allopregnanolone for treating various CNS disorders in a bio-acceptable way whereby desirable release and subsequent effective absorption of allopregnanolone is enabled for treating subjects in need of allopregnanolone for treating CNS disorders. In some aspects, we have surprisingly found that the oral compositions and methods of this invention can be effective to produce levels desirable or required for effectiveness of allopregnanolone without high sensitivity to food/meal effects.

Methods

In one embodiment, a method for ameliorating a symptom of a CNS or neuropsychiatric and neurodegenerative disorder in a subject comprises orally administering to the subject an effective amount of allopregnanolone or a pharmaceutically acceptable salt, or polymorph or combinations thereof. In another aspect, a method for ameliorating a symptom of a CNS, neuropsychiatric, and neurodegenerative disorder in a subject comprises orally administering to the subject a composition comprising an effective amount of any of oral allopregnanolone, its pharmaceutically acceptable salt, its polymorph, and a combination thereof. In one aspect, a method for ameliorating a symptom of a CNS, neuropsychiatric, and neurodegenerative disorder in a subject, when administering to the subject, comprises an amount of any of oral allopregnanolone, its pharmaceutically acceptable salt, its polymorph, and a combinations thereof that may be greater than about any of 3%, 4%, 5%, 6%, 7%, 8%, 9%, 10%, 11%, 12%, 13%, 14%, and 15% blood levels as compared to the blood levels obtained from an equivalent dose of allopregnanolone orally administered by oral aqueous non encapsulated cyclodextrin comprising composition.

In one embodiment, a method of treating a CNS disorder comprising orally administering to a subject a pharmaceutical composition comprising allopregnanolone and a plurality of additives is expected to provide in the subject at least one of an increased serum $C_{max}$ level of allopregnanolone and an increased serum $C_{avg}$ level of allopregnanolone, wherein the noted increases are greater than like increases obtained from administering to the subject a substantially equivalent amount of at least one of: a allopregnanolone in non-encapsulated SBE-β-CD aqueous solution (a cyclodextrin administration) comprising at least 250 mg/ml of SBE-β-CD, a allopregnanolone in medium chain triglyceride (MCT) solution (an MCT administration), a allopregnanolone in polysorbate-80 suspension (a polysorbate 80 administration), and a allopregnanolone in canola oil or peanut oil (an edible oil administration).

In another aspect, the allopregnanolone in the current compositions of this invention can be in a form that increases serum levels of allopregnanolone wherein the noted increases are greater than like increases obtained from administering to the subject a substantially equivalent amount of at least one of: a cyclodextrin administration, an MCT administration, a polysorbate 80 administration, and an edible oil administration. In one example, the serum levels of allopregnanolone can be increased by at least about 20% higher as compared to the serum levels obtained by administering to the subject a substantially equivalent amount of: a cyclodextrin administration, an MCT administration, a polysorbate 80 administration, and an edible oil administration.

In one embodiment, the disclosed composition is such that when the composition is administered to a subject, the administration results in a dose normalized minimum $AUC_{0-24}$ in the subject of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L.

In one embodiment, the disclosed composition is such that when the composition is administered to a subject the administration results in a minimum $AUC_{0-24}$ of at least one of about 18 ng*h/mL, about 19 ng*h/mL, and about 20 ng*h/mL.

In one embodiment, the disclosed composition is such that when the composition is administered to a subject the administration results in an $AUC_{0-24}$ having an increase in efficiency as assessed by dose normalized $AUC_{0-24}$.

In one embodiment, the disclosed composition is such that when the composition is administered to a subject the administration results in a $C_{max}$ that exceeds an $C_{max}$ resulting from an oral administration of an alternate composition comprising a comparable amount of allopregnanolone, wherein the alternate composition further comprises at least one of: a cyclodextrin composition, an untreated allopregnanolone form comprising, a surfactant-less composition, a low-surfactant composition.

In one embodiment, when the subject is in a fasting state, administration of the composition to the subject results in a dose normalized maximum $C_{max}$ in the subject of at least one of about 0.28 ng mL$^{-1}$ mg$^{-1}$, about 0.26 ng mL$^{-1}$ mg$^{-1}$, about 0.24 ng mL$^{-1}$ mg$^{-1}$, about 0.22 ng mL$^{-1}$ mg$^{-1}$, about 0.20 ng mL$^{-1}$ mg$^{-1}$, about 0.18 ng mL$^{-1}$ mg$^{-1}$, about 0.16 ng mL$^{-1}$ mg$^{-1}$, about 0.14 ng mL$^{-1}$ mg$^{-1}$, about 0.13 ng mL$^{-1}$ mg$^{-1}$, and about 0.12 ng mL$^{-1}$ mg$^{-1}$.

In one embodiment, when the subject is in a fasting state, administration of the composition to the subject results in a minimum $C_{max}$ in the subject of at least one of about 9.50 ng/mL, about 14.50 ng/mL, about 20.00 ng/mL, and about 25.00 ng/mL.

In one embodiment, when the subject is in a fed state, administration of the composition to the subject results in a dose normalized minimum $C_{max}$ in the subject of at least one of about 0.14 ng mL$^{-1}$ mg$^{-1}$, about 0.16 ng mL$^{-1}$ mg$^{-1}$, about 0.18 ng mL$^{-1}$ mg$^{-1}$, about 0.20 ng mL$^{-1}$ mg$^{-1}$, about 0.22 ng mL$^{-1}$ mg$^{-1}$, about 0.24 ng mL$^{-1}$ mg$^{-1}$, and about 0.26 ng mL$^{-1}$ mg$^{-1}$.

In one embodiment, when the subject is in a fed state, administration of the composition to the subject results in the subject a minimum $C_{max}$ in the subject of at least one of about 4.25 ng/mL, about 4.50 ng/mL, about 4.75 ng/mL, about 5.00 ng/mL, about 5.25 ng/mL, about 5.50 ng/mL, and about 6.00 ng/mL.

In one embodiment, when the subject is in a fasting state, administration of the composition to the subject results in a $T_{max}$ of allopregnanolone in the subject of at least one of less than about 1.5 hours, less than about 2 hours, less than about 3 hours, and less than about 4 hours post-administration.

In one embodiment, when the subject is in a fed state, administration of the composition to the subject results in a $T_{max}$ of allopregnanolone in the subject of at least one of less than about 1.5 hours, less than about 2 hours, less than about 3 hours, and less than about 4 hours post-administration.

In one embodiment, a dose of the administration comprises at least one of about 10 mg to about 1200 mg of allopregnanolone, about 20 mg to about 600 mg of allopregnanolone, about 30 mg to about 400 mg of allopregnanolone, about 40 mg to about 300 mg of allopregnanolone, about 50 mg to about 250 mg of allopregnanolone, and about 60 mg to about 180 mg of allopregnanolone.

In one embodiment, a dose of the administration comprises at least one of a QD dose, a BID dose, a TID dose, a QID dose, and a more than QID dose.

In one embodiment, the duration of therapy can at least one of a minimum of 1 day, 2 days, 2.5 days, 3 days, 5, days, 7 days, and 14 days.

In one aspect, the CNS disorder may be any one or more of: sleep disorders (e.g., insomnia), mood disorders (e.g., depression such as PND, major depressive disorder, postpartum depression, essential tremor, treatment resistant depression, or perinatal depression), dysthymic disorder (e.g., mild depression), bipolar disorder (e.g., "i" and/or II), anxiety disorders (e.g., generalized anxiety disorder (GAD), social anxiety disorder), stress, post-traumatic stress disorder (PTSD), compulsive disorders (e.g., obsessive compulsive disorder (OCD)), schizophrenia spectrum disorders (e.g., schizophrenia, schizoaffective disorder), convulsive disorders (e.g., epilepsy, status epilepticus (SE)), seizures), disorders of memory and/or cognition (e.g., attention disorders, attention deficit hyperactivity disorder (ADHD)), dementia (e.g., Alzheimer's type dementia, Lewis body type dementia, vascular type dementia), movement disorders (e.g., Huntington's disease, Parkinson's disease), personality disorders (e.g., anti-social personality disorder, obsessive compulsive personality disorder), autism spectrum disorders (ASD) (e.g., autism, monogenetic causes of autism such as synaptopathy, Rett syndrome, Fragile X syndrome, Angelman syndrome), pain (e.g., neuropathic pain, injury related pain syndromes, acute pain, chronic pain), traumatic brain injury (TBI), vascular diseases (e.g., stroke, ischemia, vascular malformations), substance abuse disorders and/or withdrawal syndromes (e.g., addition to opiates, cocaine, and/or alcohol), tinnitus and combinations thereof.

In another embodiment, the disclosed method of treating a CNS disorder may include orally administering to a subject an amount of allopregnanolone sufficient to enable the binding of $GABA_A$ receptors in the subject such that the CNS disorder of the subject is substantially reduced or eliminated.

In an embodiment of the invention, the disclosed method comprises orally administering to a subject a composition having orally bioavailable allopregnanolone therein, wherein the subject has at least one of: an acute CNS disorder, an episodic CNS disorder, an intermittent CNS disorder, a sub-chronic CNS disorder, a chronic CNS disorder, and combinations thereof. When the CNS disorder is sub-chronic or chronic, the dosage regimen may range from at least once per day for a specified duration of from about a single day to about 3 months, or for more than 3 months.

The subjects, in one embodiment, in need of the oral compositions comprising orally bioavailable allopregnanolone described herein can have a CNS disorder, such as depression disorders (e.g., postpartum depression, postpartum substance addiction disorder, major depressive disorder, treatment resistant depression, perinatal depression, perimenopausal or postmenopausal depression), In some embodiments, the oral compositions comprising can be used for the treatment, reduction, or enhancement of conditions, symptoms, or diseases associated with CNS disorders described hereof can be males or females. In one aspect, subjects can be adolescent males or adult males. In further aspects, subjects can be adolescent, adult, female of childbearing age, pre-menopausal, perinatal, postpartum, pregnant, peri-menopausal, or post-menopausal females. In yet another aspect, the subject may not be exhibiting symptoms of a CNS disorder yet can have a disease associated with or caused by the CNS disorder described herein.

An exemplary diagnosis and treatment of a clinical CNS disorder, such as depression, can be assessed by at least one of the following rating scales/questionnaires or similar measures that include measuring severity of depression in individuals:

a. 17-item Hamilton Rating Scale for Depression (HAM-D)

The Hamilton Rating Scale for Depression is a 17-item questionnaire used to diagnose depression, and as a guide to evaluate recovery and remission. The HAM-D is the most commonly used instrument for assessing symptoms of depression and is administered by a trained physician.

b. Montgomery-Asberg Depression Rating Scale for Depression (MADRS)

The Montgomery-Asberg Depression Scale is a clinician-rated scale used to examine the severity of depressive episodes in patients with mood disorders. It consists of a clinical interview of 10 items that moves from broad questions to more detailed ones.

c. Columbia-Suicide Severity Rating Scale (C-SSRS)

The Colombia Suicide Severity Scale is a suicidal ideation and behavior rating scale used to evaluate suicidality. The C-SSRS consists of a baseline assessment that evaluates the lifetime experiences of the subject with suicidal ideation and/or behavior, and a post-baseline evaluation that focuses on suicidal risk since the last visit.

d. Clinical Global Impression Scales for Severity (CGI-S) and Improvement (CGI-I)

The Clinical Global Impression is a validated measure used in clinical research. It allows clinicians to integrate several sources of information into a single rating of the subject's condition.

e. The Clinical Global Impression Scale of Severity (CGI-S)

CGI-S is an objective measure of the severity of patient's illness at the time of assessment, relative to the clinician's past experience with patients who have the same diagnosis.

f. The Clinical Global Impression Scale of Improvement (CGI-I)

CGI-I is a 7-item measure to assess the overall improvement of the patient's illness, relative to the subject's baseline condition.

g. Hamilton Rating Scale for Anxiety (HAM-A)

The Hamilton Rating Scale for Anxiety is a clinician-rated scale used to assess the severity of anxiety symptoms. The HAM-A consists of 14-items, each defined by a series of anxiety symptoms, both psychic and somatic.

h. Edinburgh Postnatal Depression Scale (EPDS)

The Edinburgh Postnatal Depression Scale is a self-rated questionnaire used to identify postpartum depression in outpatient, home visiting settings, or at the 6-8 week examination after delivery. The EPDS consists of 10 items that assess depressive symptoms such as feeling of guilt, low energy, anhedonia, sleep disturbance, and suicidal ideation.

i. Maternal Postnatal Attachment Scale (MPAS)

The Maternal Postnatal Depression Scale is a self-rated questionnaire used to assess the mother-to-infant attachment. The MPAS consists of 19 items that evaluate the emotional bond between the mother and the infant.

j. The Center for Epidemiologic Studies Depression Scale (CES-D)

The Center for Epidemiological Studies-Depression (CES-D) is a 20-item measure that asks caregivers to rate how often over the past week they experienced symptoms associated with depression, such as restless sleep, poor appetite, and feeling lonely. The CES-D also provides cutoff scores (e.g., 16 or greater) that aid in identifying individuals at risk for clinical depression, with good sensitivity and specificity and high internal consistency.

k. The Beck Depression Inventory (BDI)

The Beck Depression Inventory (BDI) is a 21-item, self-report rating inventory that measures characteristic attitudes and symptoms of depression.

Clinical CNS activity can be assessed thru monitoring some of the CNS vital signs, such as composite memory, verbal memory, visual memory, psychomotor speed, reaction time, complex attention, cognitive flexibility, processing speed, executive function, non-verbal reasoning, social acuity, sustained attention, working memory, simple motor speed. Or may be assessed by monitoring occurrence of sleepiness, dry mouth, loss of consciousness, dizziness, somnolence, fatigue, and hot flashes. pulse oximetry monitoring, saccadic eye velocity measurements.

The methods described herein can be used for treating neuropsychiatric (see the Wikipedia entry for "s neuropsychiatric" such as may be found at: https://en.wikipedia.org/wiki/Neuropsychiatry) or neurodegenerative diseases and disorders. The term "neurodegenerative disease" includes diseases and disorders that are associated with the progressive loss of structure or function of neurons, or death of neurons. Neurodegenerative diseases and disorders include, but are not limited to, Alzheimer's disease (including the associated symptoms of mild, moderate, or severe cognitive impairment); amyotrophic lateral sclerosis (ALS); anoxic and ischemic injuries; ataxia and convulsion (including for the treatment and prevention and prevention of seizures that are caused by schizoaffective disorder or by drugs used to treat schizophrenia); benign forgetfulness; brain edema; cerebellar ataxia including McLeod neuroacanthocytosis syndrome (MLS) (see Internet search results for neuroacanthocytosis such as may be found at: https://www.untodate.com/contents/neuroacanthocytosis#:~:text=Neuroacanthocytosis%20refers%20to%20a%20group.RBC)%20(picture%201); closed head injury; coma; contusive injuries (e.g., spinal cord injury and head injury); dementias including multi-infarct dementia and senile dementia; disturbances of consciousness; Down syndrome; drug-induced or medication-induced Parkinsonism (such as neuroleptic-induced acute akathisia, acute dystonia, Parkinsonism, or tardive dyskinesia, neuroleptic malignant syndrome, or medication-induced postural tremor); epilepsy; fragile X syndrome; Gilles de la Tourette's syndrome; head trauma; hearing impairment and loss; Huntington's disease; Lennox syndrome; levodopa-induced dyskinesia; mental retardation; movement disorders including akinesias and akinetic (rigid) syndromes (including basal ganglia calcification, corticobasal degeneration, multiple system atrophy, Parkinsonism-ALS dementia complex, Parkinson's disease, postencephalitic parkinsonism, and progressively supranuclear palsy); muscular spasms and disorders associated with muscular spasticity or weakness including chorea (such as benign hereditary chorea, drug-induced chorea, hemiballism, Huntington's disease, neuroacanthocytosis, Sydenham's chorea, and symptomatic chorea), dyskinesia (including tics such as complex tics, simple tics, and symptomatic tics), myoclonus (including generalized myoclonus and focal cyloclonus), tremor (such as rest tremor, postural tremor, and intention tremor) and dystonia (including axial dystonia, dystonic writer's cramp, hemiplegic dystonia, paroxysmal dystonia, and focal dystonia such as blepharospasm, oromandibular dystonia, and spasmodic dysphonia and torticollis); neuronal damage including ocular damage, retinopathy or macular degeneration of the eye; neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest; Parkinson's disease; seizure; status epilecticus; stroke; tinnitus; tubular sclerosis, and viral infection induced neurodegeneration (e.g., caused by acquired immunodeficiency syndrome (AIDS) and encephalopathies). Neurodegenerative diseases also include, but are not limited to, neurotoxic injury which follows cerebral stroke, thromboembolic stroke, hemorrhagic stroke, cerebral ischemia, cerebral vasospasm, hypoglycemia, amnesia, hypoxia, anoxia, perinatal asphyxia and cardiac arrest.

In one aspect, the current methods comprising allopregnanolone, its pharmaceutically acceptable salt, or its polymorph in a pharmaceutically acceptable composition thereof can also be used as a prophylactic therapy to a subject having a CNS disorder, a traumatic brain injury, status epilepticus, convulsive status epilepticus, early status epilepticus, established status epilepticus, refractory status epilepticus, super-refractory status epilepticus; non-convulsive status epilepticus, generalized status epilepticus, complex partial status epilepticus, generalized periodic epileptiform discharges, and periodic lateralized epileptiform discharges; prior to the onset of a seizure.

A seizure (see internet search results for "seizures" such as may be found at: https://www.epilepsy.com/learn/types-seizures/clonic-seizures#:~:text=Clonic%20means%20sustained%20rhythmical%20jerking.stopped%20by%20restraining%20the%20person) is the physical findings or changes in behavior that occur after an episode of abnormal electrical activity in the brain. When seizures become a consistent problem, the condition is called epilepsy. The term "seizure" is often used interchangeably with "convulsion." Convulsions are defined by a person's body shaking rapidly and uncontrollably. During convulsions, a person's muscles contract and relax repeatedly. Based on the type of behavior and brain activity, seizures are divided into two broad categories, namely: generalized and partial (also called local or focal). Classifying the type of seizure helps a doctor diagnose whether or not a patient has epilepsy. Generalized seizures are produced by electrical impulses from throughout the entire brain, whereas partial seizures are produced (at least initially) by electrical impulses in a relatively small sub portion of the brain. The part of the brain that generates seizures is sometimes called the focus. There are six types of generalized seizures. The most common and dramatic, and therefore the most well-known, is the generalized convulsion, also called the grand mal (generalized tonic-clonic) seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand mal seizures, injuries and accidents may occur, such as tongue biting and urinary incontinence. Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of losing time. Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time. Tonic seizures are characterized by stiffening of the muscles. Atonic seizures consist of a sudden and general loss of muscle tone, particularly in the arms and legs, which often results in a fall. Seizures with or without epilepsy described herein may include epileptic seizures, acute repetitive seizures, cluster seizures, continuous seizures; unremitting seizures, prolonged seizures, recurrent seizures, status epilepticus seizures, refractory convulsive status epilepticus seizures, non-convulsive status epilepticus seizures, refractory seizures, myoclonic seizures, tonic seizures, tonic-clonic seizures, simple partial seizures, complex partial seizures, secondarily generalized seizures, atypical absence seizures, absence seizures, childhood absence epilepsy (CAE), atonic seizures, benign Rolandic seizures, febrile seizures, emotional seizures, focal seizures, gelastic seizures, generalized onset seizures, infantile spasms, Jacksonian seizures, massive bilateral monooclonus seizures, multifocal seizures, neonatal onset seizures, nocturnal seizures, occipital lobe seizures, post traumatic seizures, subtle seizures, Sylvan seizures, visual reflex seizures, or withdrawal seizures. In some embodiments, the seizure is a generalized seizure associated with at least one of Dravet Syndrome, Lennox-Gastaut Syndrome, Tuberous Sclerosis Complex, CDLKS disorder, Rett Syndrome or PCDH19 Female Pediatric Epilepsy. Juvenile myoclonic epilepsy (JME) is the most common generalized epilepsy syndrome.

Typically, epileptic patients need to take seizure medicine throughout their life as monotherapy or polytherapy with multiple agents to treat, prevent, reduce, or control seizures and epilepsies.

In one embodiment, methods of treating or preventing a neurodegenerative disease by orally administering the oral compositions comprising orally bioavailable allopregnanolone also include treating or preventing loss of neuronal function characteristic of neurodegenerative disorder, such as status epilepticus (SE). Status epilepticus (SE) can include, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, focal non-convulsive status epilepticus, complex partial non-convulsive status epilepticus, simple partial non-convulsive status epilepticus, subtle non-convulsive status epilepticus; generalized non-convulsive status epilepticus, late onset absence non-convulsive status epilepticus, atypical absence non-convulsive status epilepticus, or typical absence non-convulsive status epilepticus.

In one embodiment, a pharmaceutically acceptable compositions and methods described herein can be administered as a monotherapy to a subject having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, seizure clusters, acute repetitive seizures, generalized periodic epileptiform discharges, periodic lateralized epileptiform discharges, to treat, prevent, reduce, or improve seizures or epilepsies.

In another embodiment, the pharmaceutically acceptable compositions and methods described herein may be administered as a monotherapy to a subject having at least one of four classified epilepsies, which comprise focal epilepsy such as frontal lobe epilepsy, generalized epilepsy, combined generalized and focal epilepsy, simple or complex partial onset epilepsy, and unknown epilepsy (including neonatal and infantile epilepsies) as classified by the International League Against Epilepsy (ILAE) in 2017, to treat, prevent, reduce, or improve seizures or epilepsies.

In one aspect, the compositions and methods disclosed herein may be used to treat, prevent, reduce, or improve at least one of generalized epilepsies, comprising generalized tonic-clonic seizures (symptoms: loss of consciousness followed by body stiffening, then violent jerking after falling into a deep sleep), absence (or non-motor) seizures (symptoms: brief loss of consciousness), myoclonic seizures (symptoms: sporadic and brief jerking movements, usually on both sides of body), clonic seizures (symptoms: repetitive, rhythmic jerking movements on both sides of body at the same time), tonic seizures (symptoms: muscle stiffness and rigidity), and atonic seizures (symptoms: a sudden and general loss of muscle tone in arms and legs).

In another aspect, the compositions and methods disclosed herein may be used to treat, prevent, reduce, or improve at least one of focal epilepsies, comprising focal retained awareness seizures (motor/sensory/autonomic/psychological), focal impaired awareness seizures, focal motor seizures, focal non-motor seizures, focal to bilateral tonic-clonic seizures.

In a further aspect, the compositions and methods disclosed herein can treat, prevent, reduce, or improve at least one of unknown (or idiopathic) epilepsies, comprising unknown motor seizures, unknown non-motor seizures, and unclassified seizures including neonatal and infantile seizures. Unknown seizures are defined as seizures that occur either in sleep or in a condition that cannot be described as the patient is alone or the witness cannot describe it. Among them, unclassified seizures are given when a clinician is certain that the event is a seizure but cannot describe it due to incomplete information.

In one embodiment, a pharmaceutically acceptable compositions and methods described herein can be administered as an adjunctive therapy to a subject having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, periodic lateralized epileptiform discharges, to treat, prevent, reduce, or improve seizures or epilepsies.

In another embodiment, a pharmaceutically acceptable compositions and methods described herein can be administered as an adjunctive therapy to a subject having at least one of four classified epilepsies, which comprises focal epilepsy, generalized epilepsy, combined generalized and focal epilepsy, and unknown epilepsy, to treat, prevent, reduce, or improve seizures or epilepsies.

In one aspect, a pharmaceutically acceptable compositions and methods described herein can be administered as an adjunctive therapy with at least one of anti-epileptic agents, such as bromide, phenobarbital, mephobarbital, phenytoin, acetazolamide, trimethadione, mephenytoin, paramethadione, corticosteroids, adrenocorticotropic hormone (ACTH), phenacemide, phensuximide, primidone, methsuximide, ethotoin, ethosuximide, chlordiazepoxide, sulthiame, diazepam, carbamazepine, valproate, clonazepam, clobazam, progabide, vigabatrin, zonisamide, lamotrigine, oxcarbazepine, felbamate, gabapentin, topiramate, tiagabine, levetiracetam, pregabalin, stiripentol, rufinamide, lacosamide, eslicarbazepine acetate, retigabine (ezogabine), perampanel, imepitoin, brivaracetam, everolimus, valproic acid, eslicarbazepine, cenobamate, fenfluramine, midazolam, and alprazolam, to treat, prevent, reduce, or improve seizures or epilepsies in subjects in need of therapy.

Research indicates that females have a marginally lower incidence of epilepsy and unprovoked (or reflex) seizures than males. This difference is usually attributed to male's greater exposure to risk factors for lesional epilepsy and acute symptomatic seizures. Idiopathic generalized epilepsies (IGEs), comprising about 15-20% of all epilepsies, are more common among females. Also, the behavior of some common epilepsy syndromes such as mesial temporal sclerosis may differ between genders with isolated auras more common among females and secondary seizure spread more likely in males. For example, the epilepsy trend between genders indicates that the incidence of status epilepticus, the incidence of sudden unexpected death in epilepsy (SUDEP), prognosis, and mortality are more common in men. For another example, boys with epilepsy with myoclonic-astatic seizures (Doose syndrome—see for instance the website for the Doose Syndrome Epilepsy Alliance) suffer about two times more often than girls. Also, focal seizures with hypermotor automatisms are about two times more prevalent in men than in women.

More women were diagnosed with idiopathic generalized epilepsy than men. No gender difference was found in localization-related epilepsy, but localization-related symptomatic epilepsies were more frequent in men, and cryptogenic localization-related epilepsies were more frequent in women.

There are epileptic syndromes that are more common in women such as pediatric absence epilepsy, typical early onset absence epilepsy, photosensitive forms of epilepsy, juvenile myoclonic epilepsy, and catamenial epilepsy.

Subjects who may be in need of the disclosed compositions and methods and for whom the disclosed compositions and methods may be of use include women of childbearing age (e.g., 12-49, 15-49, or 18-45 years of age). More specifically, the disclosed compositions and methods may be of particular usefulness for such women, who are capable of a nulliparous or multiparous (>1 year postpartum or previous delivery) planned or unplanned pregnancy, and more especially during the preconception phase, the pregnant phase, the labor phase, the peripartum phase, and the postpartum phase.

Women of the perimenopausal phase are defined as women in the period around menopause, ranging from about 39 to about 50 years of age (e.g., the perimenopausal age may be 40 to 50 years of age).

Before the age of 10 (including infantile and pediatric ages), pseudo-epileptic paroxysms are equally common in boys and girls. After 10 years (ages up to 18 years) pseudo-epileptic paroxysms are more common in girls. In adulthood (from ages of 18 years to about 70 years), women suffer from pseudo-epileptic paroxysms in 60-80% of epileptic cases. In the pubertal period and up to 30 years and over the age of 70 years, epilepsy is more common in women than in men. At puberty, young men are much more likely to work in their free time, and such work may lead to sleep deprivation and provoke epileptic seizures.

In one embodiment, the pharmaceutically acceptable compositions and methods described herein may be administered to childhood males or childhood females at ages of 5 to 17 years of age having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, acute repetitive seizures, and periodic lateralized epileptiform discharges, to treat, prevent including breakthrough seizures, improve, or control seizures or epilepsies such subjects.

In another embodiment, the pharmaceutically acceptable compositions and methods described herein may be administered to childhood males or childhood females at ages of 5 to 17 years of age having at least one of four classified epilepsies, which comprises focal epilepsy, generalized epilepsy, combined generalized and focal epilepsy, and unknown epilepsy as classified by the International League Against Epilepsy (ILAE) in 2017, to treat seizures or epilepsies in such subjects.

In one embodiment, the pharmaceutically acceptable compositions and methods described herein may be administered to a male having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, acute repetitive seizures, and periodic lateralized epileptiform discharges, to treat seizures or epilepsies.

In another embodiment, a pharmaceutically acceptable compositions and methods described herein may be administered to a male having at least one of four classified epilepsies, which comprise focal epilepsy, generalized epilepsy, combined generalized and focal epilepsy, and unknown epilepsy as classified by the International League Against Epilepsy (ILAE) in 2017, to treat seizures or epilepsies.

In adult men, either epilepsy or AEDs (anti-epileptic drugs) may cause dysfunction of the hypothalamic-pituitary-sexual system at all of its levels, which may result in sexual dysfunctions. Epileptic seizures are often associated with hormonal disorders, causing the release of hypothalamic and pituitary hormones. Also, some AEDs may alter the level of sex hormones, as well as induce their effects. Interictal increase of prolactin is observed in men and women with epilepsies, regardless of the anti-epileptic therapy that may be administered. An epileptic seizure may cause an increase in the level of prolactin, which reaches a maximum at short time (within ~1 hr.) after the attack. In one aspect, the pharmaceutically acceptable compositions and methods described herein may be administered to a male with epilepsy having symptoms of sexual dysfunctions, to reduce, prevent, improve, or treat the epilepsy and/or its side effects, such as sexual dysfunction, increase of prolactin, increase of sex hormone binding globulin (SHBG), and decrease of free testosterone.

In one embodiment, the pharmaceutically acceptable compositions and methods described herein may be administered to a female having at least one of traumatic brain injury epilepsy, status epilepticus, convulsive status epilepticus, early status epilepticus, established status epilepticus, refractory status epilepticus, super-refractory status epilepticus, non-convulsive status epilepticus, generalized status epilepticus, complex partial status epilepticus, generalized periodic epileptiform discharges, acute repetitive seizures, and periodic lateralized epileptiform discharges, to treat seizures or epilepsies.

In another embodiment, the pharmaceutically acceptable compositions and methods described herein may be administered to a female having at least one of four classified epilepsies, which comprises focal epilepsy such as frontal lobe epilepsy, generalized epilepsy, combined generalized and focal epilepsy, and unknown epilepsy as classified by the International League Against Epilepsy (ILAE) in 2017, to treat seizures or epilepsies.

In one embodiment, the pharmaceutically acceptable compositions and methods described herein may be administered to menopausal or perimenopausal women with epilepsy or active epilepsy (controlled or uncontrolled seizures in the previous 6-12 months prior to the start of or adjunct to other AED(s) or monotherapy) to improve, control, prevent, prevent an increase, including breakthrough seizures, or treat seizures or epilepsy, and/or mood disorder, and/or sleep disorder.

In one embodiment, the pharmaceutically acceptable compositions and methods described herein may be administered to menopausal or perimenopausal women with a history of catamenial epilepsy or active epilepsy (controlled or uncontrolled seizures in the previous 6-12 months prior to the start of or adjunct to other AED(s) or monotherapy) to improve, control, prevent, prevent an increase, or treat seizures or epilepsy, and/or mood/disorder, and/or sleep disorder.

In one embodiment, the pharmaceutically acceptable compositions and methods described herein may be administered to menopausal or perimenopausal women with epilepsy or active epilepsy (controlled or uncontrolled seizures in the previous 6-12 months prior to the start of or adjunct to other AED(s) or monotherapy) and having endogenous positive allosteric NAS deficiency, to improve, control, prevent, prevent an increase, or treat seizures or epilepsy, and/or mood disorder, and/or sleep disorder.

In one embodiment, the pharmaceutically acceptable compositions and methods described herein may be administered to menopausal or perimenopausal women or women of childbearing age on hormone replacement therapy with epilepsy or active epilepsy (controlled or uncontrolled seizures in the previous 6-12 months prior to the start of or adjunct to other AED(s) or monotherapy) and having endogenous positive allosteric modulator NAS deficiency, to improve, control, prevent, prevent an increase, or treat seizures or epilepsy, and/or mood disorder, and/or sleep disorder.

In one embodiment, a pharmaceutically acceptable compositions and methods described herein can be administered to menopausal or perimenopausal women or women of childbearing age with epilepsy or active epilepsy (controlled or uncontrolled seizures in the previous 6-12 months prior to start of adjunct to other anti-epileptic drugs (AED) or monotherapy) and at risk of compromised bone health, to improve, control, prevent, or treat seizures or epilepsy, and/or mood disorder, and/or sleep disorder.

In one embodiment, a pharmaceutically acceptable compositions and methods described herein can be administered to menopausal or perimenopausal women or women of childbearing age with epilepsy with at least 3 or more seizures per month just prior to start of adjunct to other anti-epileptic drugs (AED) or monotherapy to improve, control, prevent, or treat seizures or epilepsy, and/or mood disorder, and/or sleep disorder.

In one embodiment, a pharmaceutically acceptable compositions and methods described herein can be administered to menopausal or perimenopausal women or women of childbearing age with epilepsy with no greater than 25 seizure-free days just prior to start of adjunct to other anti-epileptic drugs (AED) or monotherapy to improve, control, prevent, or treat seizures or epilepsy, and/or mood disorder, and/or sleep disorder.

In one embodiment, the pharmaceutically acceptable compositions and methods described herein may be administered to women of childbearing age with epilepsy or active epilepsy just prior to start of or adjunct to other AED(s) or monotherapy, to improve, control, prevent, prevent an increase, or treat seizures or epilepsy, and/or mood disorder, and/or sleep disorder without regard to use of oral hormonal contraceptives.

In one embodiment, the pharmaceutically acceptable compositions and methods described herein may be administered to women of childbearing age with epilepsy or active epilepsy and have and having endogenous progesterone or positive allosteric modulator NAS deficiency, or hyper testosterone or estrogen levels, just prior to start of or adjunct to other AED(s) or monotherapy, to improve, control, prevent, prevent an increase, or treat seizures or epilepsy, and/or mood disorder, and/or sleep disorder without regard to use of oral hormonal contraceptives.

In one embodiment, the pharmaceutically acceptable compositions and methods described herein may be administered to women of childbearing age with epilepsy or active epilepsy without regard to drug-drug interaction (DDI) compromising either contraception or seizure control efficacy of co-administered drugs, to improve, control, prevent, prevent an increase, or treat seizures or epilepsy, and/or mood disorder, and/or sleep disorder.

In one embodiment, the pharmaceutically acceptable compositions and methods described herein may be administered to women of childbearing age with epilepsy or active epilepsy and menses disorder, such as premenstrual syndrome, premenstrual dysphoric disorder (PMDD), and ovulation disorder, to improve, control, prevent, prevent an increase, or treat seizures or epilepsy, and/or mood disorder, and/or sleep disorder.

In one embodiment, the pharmaceutically acceptable compositions and methods described herein may be administered to women of childbearing age with epilepsy as an adjunct to other AED(s) to prevent breakthrough seizures or maintain seizure control as the AED dose is adjusted in women planning a pregnancy.

In one embodiment, the pharmaceutically acceptable compositions and methods described herein may be administered to women of childbearing age with epilepsy as an adjunct or monotherapy to other AED(s) to substitute all or substantial dosages of such AED(s) with teratogenic risk in women planning a pregnancy.

In one embodiment, a pharmaceutically acceptable compositions and methods described herein may be administered to women of childbearing age with epilepsy as an adjunct or monotherapy to other AED(s) to reduce or eliminate dependency on polypharmacy of such AED(s) for seizure control dosage in women planning a pregnancy.

In one embodiment, the pharmaceutically acceptable compositions and methods described herein may be administered to women of childbearing age with epilepsy as an adjunct or monotherapy to other AED(s) to reduce or eliminate dependency on polypharmacy of such AED(s) for seizure control dosage in women planning a pregnancy, by providing physiological levels of endogenous NAS.

In one embodiment, the pharmaceutically acceptable compositions and methods described herein may be administered as an adjunct to other AED(s) or monotherapy to improve, control, prevent, prevent an increase, or treat at least one of seizure management, depression, anxiety, sleep impairment, and suicidal ideation, in a woman of childbearing age with epilepsy or active epilepsy, who is pregnant, planning to be pregnancy, or at risk of getting pregnant.

In one embodiment, the pharmaceutically acceptable compositions and methods described herein may be administered as an adjunct to other AED(s) without an increase in AED dosage or monotherapy to improve, control, prevent, prevent an increase, or treat at least one of seizure management, depression, anxiety, sleep impairment, and suicidal ideation, in a woman of childbearing age who is pregnant.

In one embodiment, the pharmaceutically acceptable compositions and methods described herein may be administered as an adjunct to other AED(s) or monotherapy to improve, control, prevent, prevent an increase, prevent an increase, or treat seizures management and at least one of an associated comorbid condition, such as depression, anxiety, sleep impairment, and suicidal ideation, in a woman of childbearing age with epilepsy or active epilepsy, who is pregnant, planning to be pregnancy, or at risk of getting pregnant.

In one aspect, the pharmaceutically acceptable compositions and methods described herein may be administered to a childbearing female having at least one of pediatric absence epilepsy, typical early onset absence epilepsy, photosensitive forms of epilepsy, juvenile myoclonic epilepsy, acute repetitive seizures, and catamenial epilepsy, to treat seizures, epilepsy, or related symptoms. In another aspect, the pharmaceutically acceptable compositions and methods described herein may be administered to a woman of childbearing age having catamenial epilepsy, comprising 1) epilepsy related to premenstrual withdrawal of the anticonvulsant effects of endogenous NAS mediated through their action on $GABA_A$ receptors and related to alteration in $GABA_A$ receptor subunits and subsequent changes in neuronal inhibition, 2) estrogen peak in the day before ovulation, and 3) increased frequency of anovulatory cycles due to hypothalamic-pituitary-gonadal axis dysregulation and consequent low progesterone luteal phases, to treat seizures or epilepsies. Catamenial epilepsy patterns may be classified as three types by the time period in the menstrual cycle, namely: 1) Perimenstrual pattern (C1 pattern: related to decline of progesterone, day 25 to day 3), 2) Periovulatory pattern (C2 pattern: related to sudden increase of estrogen, day 10 to day 15), and 3) Luteal pattern (C3 pattern: related to inadequate luteal phase cycles by low progesterone levels resulting in anovulatory cycles, day 10 in one cycle to day 3 in next cycle). Premenstrual (or Perimenstrual) pattern or C1 pattern epilepsy is the most frequent type of epilepsy in childbearing female subjects with catamenial epilepsy.

In one aspect, the pharmaceutically acceptable compositions and methods described herein may be administered to a childbearing age female having at least one of perimenstrual pattern catamenial epilepsy, preovulatory pattern catamenial epilepsy, and luteal pattern catamenial epilepsy, to treat seizures or epilepsies.

In one embodiment, the pharmaceutically acceptable compositions and methods described herein may be administered to a postmenopausal or perimenopausal female having epilepsy related to low estrogen and low progesterone levels (a type of focal epilepsy), epilepsy not related to hormone levels (a type of generalized epilepsy), and unknown epilepsy, to treat seizures or epilepsies.

In one embodiment, the pharmaceutically acceptable compositions and methods described herein may be administered to a pregnant female having epilepsy, comprising focal epilepsy, generalized epilepsy, combined generalized and focal epilepsy, and unknown epilepsy, to treat seizures or epilepsies. For some pregnant women, particularly women who are sleep deprived or do not take medication as prescribed, pregnancy increases the frequency of seizures. In one aspect, the pharmaceutically acceptable compositions and methods described herein may be administered to a pregnant female having epilepsy, to treat symptoms or diseases caused by epilepsy during pregnancy, such as slowing of the fetal heart rate, decrease in oxygen to the fetus, fetal injury, premature separation of the placenta from the uterus (placental abruption), miscarriage due to trauma (e.g., a fall during a seizure), preterm labor, sudden infant death syndrome, breastfeeding difficulty, birth defects, and premature birth.

In one embodiment, the pharmaceutically acceptable compositions and methods described herein may be administered to a peripartum (late pregnancy and post-delivery) female having epilepsy or seizures comprising three types of seizures, namely: 1) the exacerbation of a known pre-existing seizure disorder, mainly epilepsy, 2) the new onset of seizures due to a non-pregnancy-related problem, and 3) seizures related to pregnancy conditions, to treat seizures or epilepsies. Seizures related to pregnancy have two categories, namely: i) focus on eclampsia, and ii) pregnancy-related new onset seizures, of which conditions include at least one of posterior reversible encephalopathy syndrome, reversible cerebral vasoconstriction syndrome, cerebral venous sinus thrombosis, thrombotic thrombocytopenic purpura, amniotic fluid embolism, and air embolism.

In general, in one embodiment, the oral compositions and methods of disclosed herein may be administered to treat CNS disorders (e.g., suicide ideation, depression, anxiety, bipolar disorder, essential tremor, neuropathic pain syndromes, trigeminal neuralgia, etc.) in women with epilepsy, to manage epilepsy during menses, pregnancy, or peripartum and postpartum in epileptic women of childbearing age, and to manage epilepsy in post or peri menopausal women.

In another embodiment, the oral compositions and methods of disclosed herein may be administered to treat CNS disorders (e.g., suicide ideation, depression, anxiety, bipolar disorder, essential tremor, neuropathic pain syndromes, trigeminal neuralgia, etc.) and to treat or manage epilepsy in adult epileptic men, childhood epileptic males, and childhood epileptic females.

Acute repetitive seizures (ARS) also known as cluster seizures, serial seizures, crescendo seizures, seizure flurries, recurrent seizures, and cyclical seizures. The frequency of ARS is typically more than 2 seizures in 24 hours, or in some cases more than 2 seizures in 6 to 8 hours. ARS has been associated with an evolution into status epilepticus. In one reported study, status epilepticus occurred more frequently in persons having cluster seizures than in people not having cluster seizures (40% versus 12%). Patients having cluster seizures have been shown to have higher death rates than those not having cluster seizures.

The occurrence of frequent seizures in short periods of time is associated with an increased incidence of postictal psychosis, which may develop into chronic psychosis. People having cluster seizures are more frequently transported to emergency rooms and have more hospital admissions as compared to those who do not have cluster seizures.

There are unmet needs in developing therapy (compositions and methods) that may treat, stop, prevent, or control the evolution of ARS occurring at home, school, or work. The therapy may prevent transport to emergency rooms and hospital admission. ARS in such settings causes significant additional stress for the patient, family, and caregivers. Thus, ARS therapy will help decrease such stress and worry. ARS therapy that may be applied to patients at home, school, or work may offer a self-management tool and a greater degree of personal control. For parents of epileptic children, ARS therapies may provide increased confidence to allow their children to be unattended by health providers or caregivers, to permit activities outside the home such as school and afterschool activities, and to enable family trips away from home.

In one embodiment, the pharmaceutically acceptable compositions and methods described herein may be administered as a monotherapy to a subject having ARS to treat, prevent, reduce, or improve seizures or epilepsies.

In another embodiment, the pharmaceutically acceptable compositions and methods described herein may be administered as an adjunctive therapy to a subject having ARS to treat, prevent, reduce, or improve seizures or epilepsies.

In one aspect, the pharmaceutically acceptable compositions and methods described herein may be administered as an adjunctive therapy in combination with at least one of an anti-epileptic agents (such as bromide, phenobarbital, mephobarbital, phenytoin, acetazolamide, trimethadione, mephenytoin, paramethadione, corticosteroids, phenacemide, phensuximide, primidone, methsuximide, ethotoin, ethosuximide, chlordiazepoxide, sulthiame, diazepam, carbamazepine, valproate, clonazepam, clobazam, progabide, vigabatrin, zonisamide, lamotrigine, oxcarbazepine, felbamate, gabapentin, topiramate, tiagabine, levetiracetam, pregabalin, stiripentol, rufinamide, lacosamide, eslicarbazepine acetate, retigabine (ezogabine), perampanel, imepitoin, brivaracetam, everolimus, valproic acid, eslicarbazepine, cenobamate, fenfluramine, midazolam, and alprazolam) to treat, prevent, reduce, or improve ARS.

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

In one embodiment, the methods described herein can be used to treat tremor, for example cerebellar tremor or intention tremor, dystonic tremor, essential tremor, orthostatic tremor, parkinsonian tremor, physiological tremor, psychogenic tremor, or rubral tremor. Tremor includes hereditary, degenerative, and idiopathic disorders such as Wilson's disease, Parkinson's disease, and essential tremor, respectively; metabolic diseases (e.g., thyroid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. Tremor is an involuntary, at times rhythmic, muscle contraction and relaxation that can involve oscillations or twitching of one or more body parts (e.g., hands, arms, eyes, face, head, vocal folds, trunk, legs). Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder). Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occur irregularly and often can be relieved by complete rest. Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occur in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease. Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease but is a symptom complex rather than a progressive neurodegenerative disease. Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face. Huntington's Disease is an inherited disease that causes nerve cells in the brain to waste away. Symptoms include uncontrolled movements, clumsiness, and balance problems. Huntington's disease can hinder walk, talk, and swallowing. Ataxia refers to the loss of full control of bodily movements, and may affect the fingers, hands, arms, legs, body, speech, and eye movements. Myloclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part. Tourette Syndrome is an inherited neuropsychiatric and neurodegenerative disorder with onset in childhood, characterized by multiple motor tics and at least one vocal tic.

Restless Legs Syndrome is a neurologic sensorimotor disorder characterized by an overwhelming urge to move the legs when at rest. Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMG recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegic gait, neuropathic gait, myopathic gait, parkinsonian gait, choreiform gait, ataxic gait, and sensory gait.

Mood disorders: Also provided herein are methods for treating a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior. In some embodiments, the method described herein provides therapeutic effect to a subject suffering from depression (e.g., moderate or severe depression). In some embodiments, the mood disorder is associated with a disease or disorder described herein (e.g., neuroendocrine diseases and disorders, neurodegenerative diseases and disorders (e.g., epilepsy), movement disorders, tremor (e.g., Parkinson's Disease), women's health disorders or conditions).

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Peripartum depression refers to depression in pregnancy. Symptoms include irritability, crying, feeling restless, trouble sleeping, extreme exhaustion (emotional and/or physical), changes in appetite, difficulty focusing, increased anxiety and/or worry, disconnected feeling from baby and/or fetus, and losing interest in formerly pleasurable activities.

Postnatal depression (PND) is also referred to as postpartum depression (PPD) and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein). In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt. Psychotic major depression (PMD) or psychotic depression refers to a major depressive episode, in particular of melancholic nature, where the individual experiences psychotic symptoms such as delusions and hallucinations. Catatonic depression refers to major depression involving disturbances of motor behavior and other symptoms. An individual may become mute and stuporous, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years). Double depression refers to fairly depressed mood (dysthymia) that lasts for at least 2 years and is punctuated by periods of major depression. Depressive Personality Disorder (DPD) refers to a personality disorder with depressive features. Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks. Bipolar disorder or manic-depressive disorder causes extreme mood swings that include emotional highs (mania or hypomania) and lows (depression). During periods of mania the individual may feel or act abnormally happy, energetic, or irritable. They often make poorly thought-out decisions with little regard to the consequences. The need for sleep is usually reduced. During periods of depression there may be crying, poor eye contact with others, and a negative outlook on life. The risk of suicide among those with the disorder is high at greater than 6% over 20 years, while self-harm occurs in 30-40%. Other mental health issues such as anxiety disorder and substance use disorder are commonly associated with bipolar disorder. Depression caused by chronic medical conditions refers to depression caused by chronic medical conditions such as cancer or chronic pain, chemotherapy, chronic stress. Treatment-resistant depression refers to a condition where the individuals have been treated for depression, but the symptoms do not improve. For example, antidepressants or psychological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Post-surgical depression refers to feelings of depression that follow a surgical procedure (e.g., as a result of having to confront one's mortality). For example, individuals may feel sadness or empty mood persistently, a loss of pleasure or interest in hobbies and activities normally enjoyed, or a persistent felling of worthlessness or hopelessness. Mood disorder associated with conditions or disorders of women's health refers to mood disorders (e.g., depression) associated with (e.g., resulting from) a condition or disorder of women's health (e.g., as described herein). Suicidality, suicidal ideation, suicidal behavior refers to the tendency of an individual to commit suicide. Suicidal ideation concerns thoughts about or an unusual preoccupation with suicide. The range of suicidal ideation varies greatly from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they will not be seen again. Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case-to-case basis. Symptoms of depression, and relief of the same, may be ascertained by a physician or psychologist (e.g., by a mental state examination).

In one embodiment, provided herein are methods for treating anxiety disorders (e.g., generalized anxiety disorder, panic disorder, obsessive compulsive disorder, phobia, post-traumatic stress disorder). Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that the attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

In another embodiment, provided herein are methods for treating conditions or disorders related to women's health. Conditions or disorders related to women's health include, but are not limited to, Gynecological health and disorders (e.g., premenstrual syndrome (PMS), premenstrual dysphoric disorder (PMDD)), pregnancy issues (e.g., miscarriage, abortion), infertility and related disorders (e.g., polycystic ovary syndrome (PCOS)), other disorders and conditions, and issues related to women's overall health and wellness (e.g., menopause). Gynecological health and disorders affecting women include menstruation and menstrual irregularities; urinary tract health, including urinary incontinence and pelvic floor disorders; and such disorders as bacterial vaginosis, vaginitis, uterine fibroids, and vulvodynia.

Premenstrual syndrome (PMS) refers to physical and emotional symptoms that occur in the one to two weeks before a women's period. Symptoms vary but can include bleeding, mood swings, tender breasts, food cravings, fatigue, irritability, acne, and depression.

Premenstrual dysphoric disorder (PMDD) is a severe form of PMS. The symptoms of PMDD are similar to PMS but more severe and may interfere with work, social activity, and relationships. PMDD symptoms include mood swings, depressed mood or feelings of hopelessness, marked anger, increased interpersonal conflicts, tension and anxiety, irritability, decreased interest in usual activities, difficulty concentrating, fatigue, change in appetite, feeling out of control or overwhelmed, sleep problems, physical problems (e.g., bloating, breast tenderness, swelling, headaches, joint or muscle pain).

Pregnancy issues include preconception care and prenatal care, pregnancy loss (miscarriage and stillbirth), preterm labor and premature birth, sudden infant death syndrome (SIDS), breastfeeding, and birth defects.

Miscarriage refers to a pregnancy that ends on its own, within the first weeks of gestation. Abortion refers to the deliberate termination of a pregnancy, which can be performed during the first 28 weeks of pregnancy.

Infertility and related disorders include uterine fibroids, polycystic ovary syndrome, endometriosis, and primary ovarian insufficiency. Polycystic ovary syndrome (PCOS) refers to an endocrine system disorder among women of reproductive age. PCOS is a set of symptoms resulting from an elevated male hormone in women. Most women with PCOS grow many small cysts on their ovaries. Symptoms of PCOS include irregular or no menstrual periods, heavy periods, excess body and facial hair, acne, pelvic pain, difficulty getting pregnant, and patches of thick, darker, velvety skin. PCOS may be associated with conditions including type 2 diabetes, obesity, obstructive sleep apnea, heart disease, mood disorders, and endometrial cancer. Other disorders and conditions that affect only women include Turner syndrome, Rett syndrome, and ovarian and cervical cancers. Issues related to women's overall health and wellness include violence against women, women with disabilities and their unique challenges, osteoporosis and bone health, and menopause.

Menopause refers to the 12 months after a woman's last menstrual period and marks the end of menstrual cycles. Menopause typically occurs in a woman's 40s or 50s. Physical symptoms such as hot flashes and emotional symptoms of menopause may disrupt sleep, lower energy, or trigger anxiety or feelings of sadness or loss. Menopause includes neutral menopause and surgical menopause, which is a type of induced menopause due to an event such as surgery (e.g., hysterectomy, oophorectomy; cancer). It is induced when the ovaries are gravely damaged by, e.g., radiation, chemotherapy, or other medications.

EXAMPLES

The following examples are provided to promote a clearer understanding of certain embodiments of the present invention and are in no way meant as a limitation thereon.

Unless otherwise stated, oral pharmaceutical composition tables describing a composition by mass for a group of compounds (e.g., additives etc.) specifically describe the mass range that each compound may be present. For example, a table describing an additive (e.g., glyceryl monocaprylocaprate, glyceryl monocaprylate) for a range from 20-2000 mg, would mean each and any dispersant used, may each individually be present in the oral pharmaceutical composition with a mass at or between 20 and 2000 mg.

Example 1. Oral Pharmaceutical Compositions Comprising Allopregnanolone

The oral pharmaceutical composition examples in the following are provided to promote a clear understanding of certain embodiments of the present invention related to treatment for a subject (a female and/or a male) in need of the therapy for CNS disorders and are in no way meant as a limitation thereon.

The following tables (Table A-C) display oral compositions or dosage forms comprising allopregnanolone in a form that comprises at least one form of solubilized, partially solubilized, dissolved, partially dissolved, amorphous solid, crystalline solid, solid dispersion, solid solution, and eutectic mixture.

TABLE A

Oral compositions comprising allopregnanolone

| Ingredient | | Composition (w/w %) | | | | |
| --- | --- | --- | --- | --- | --- | --- |
| | | A1 | A2 | A3 | A4 | A5 |
| allopregnanolone | | 31-50 | 15-30 | 10-14 | 5-9 | 0.5-5 |
| Additives | Tocopherol or its derivative, glyceryl fatty acid ester, polyglycerol fatty acid ester, triglyceride, propylene glycol fatty acid ester, fatty acid, edible oil, hydrogenated polyoxyl vegetable oil or glyceride, PEG glyceride of fatty acid ester, polyglycerol-10 fatty acid ester, polysorbate, vitamin E ester, sterols or its derivative, etc. | 50-69 | 70-85 | 86-90 | 91-95 | 95-99 |
| Other ingredients* | | q.s. | q.s. | q.s. | q.s. | q.s. |

*Other ingredients can comprise, but not limited to, co-solvent, antioxidant, permeation enhancer, stabilizer, plasticizer, solidifier, preservative, and so on (hereafter it applies to all examples below in Tables B and C.)

TABLE B

Oral compositions comprising allopregnanolone with at least one lipophilic additive and one hydrophilic additive

| Ingredient | | Composition (w/w %) | | | | |
| --- | --- | --- | --- | --- | --- | --- |
| | | B1 | B2 | B3 | B4 | B5 |
| allopregnanolone | | 31-40 | 15-30 | 10-14 | 5-9 | 0.5-5 |
| Lipophilic additives | (e.g., vitamin E or its derivative, glyceryl fatty acid ester, polyglycerol fatty acid ester, triglyceride, propylene glycol fatty acid ester, fatty acid, edible oil, etc.) | 20-66 | 40-82 | 65-87 | 70-90 | 80-96 |

TABLE B-continued

Oral compositions comprising allopregnanolone with at least one lipophilic additive and one hydrophilic additive

| Ingredient | | Composition (w/w %) | | | | |
|---|---|---|---|---|---|---|
| | | B1 | B2 | B3 | B4 | B5 |
| Hydrophilic additives | (e.g., hydrogenated polyoxyl vegetable oil or glyceride, PEG glyceride of fatty acid ester, polyglycerol-10 fatty acid ester, polysorbate, vitamin E ester, sterols or its derivative, etc.) | 3-40 | 3-30 | 3-25 | 3-20 | 3-15 |
| Other ingredients | | q.s. | q.s. | q.s. | q.s. | q.s. |

TABLE C

Oral dosage forms comprising allopregnanolone

| Component | w/w % | | | | | | |
|---|---|---|---|---|---|---|---|
| | C1 | C2 | C3 | C4 | C5 | C6 | C7 |
| allopregnanolone | 4.5 | 3.1 | 4.3 | 3.8 | 4.2 | 3.4 | 3.3 |
| Glyceryl monocaprylate (e.g., CAPMUL MCM C8) | 82.5 | 58.2 | 45.0 | 66.5 | 55.0 | 81.4 | 52.8 |
| Propylene Glycol monolaurate (e.g., CAPMUL PG-8) | | | | | | | |
| Propylene Glycol Monocaprylate (e.g., LAUROGLYCOL) | | | 2.4 | | | | 24.8 |
| Alpha-tocopherol | 4.6 | 12.2 | 22.0 | 21.3 | 20.5 | 10.2 | 11.1 |
| Peppermint oil | | | | | | | |
| TPGS | | | | | 8.8 | | |
| Hydrophilic surfactant (e.g., KOLLIPHOR RH40, KOLLIPHOR EL) | 4.9 | 26.5 | 24.0 | 8.4 | 11.5 | 5.0 | 8.0 |
| Polyglyceryl-10 mono/di-oleate (e.g., CAPROL PGE-860) | | | | | | | |
| Other additives (e.g., solidifier, antioxidant, etc.) | 3.5 | q.s. | 2.3 | q.s. | q.s. | q.s. | q.s. |
| Ratio of allopregnanolone/ Alpha-tocopherol | 0.98 | 0.25 | 0.20 | 0.18 | 0.20 | 0.33 | 0.30 |
| Ratio of allopregnanolone/ medium chain monoglyceride | 0.05 | 0.05 | 0.10 | 0.06 | 0.08 | 0.04 | 0.06 |
| Ratio of Alpha-tocopherol/ hydrophilic surfactant | 0.94 | 0.46 | 0.92 | 2.54 | 1.78 | 2.04 | 1.39 |

Oral dosage forms comprising allopregnanolone

| Component | w/w % | | | | | | |
|---|---|---|---|---|---|---|---|
| | C8 | C9 | C10 | C11 | C12 | C13 | C14 |
| allopregnanolone | 3.2 | 3.8 | 3.8 | 6.1 | 8.5 | 5.5 | 9.0 |
| Glyceryl monocaprylate (e.g., CAPMUL MCM C8) | 46.0 | | | | | | |
| Propylene Glycol monolaurate (e.g., CAPMUL PG-8) | | 43.2 | 41.2 | | | | |
| Propylene Glycol Monocaprylate (e.g., LAUROGLYCOL) | | | | 57.5 | | 16.0 | |
| Alpha-tocopherol | 2.5 | 32.2 | 4.0 | 18.5 | 32.3 | 22.0 | 47.5 |
| Peppermint oil | | | | | 43.6 | 29.5 | |
| TPGS | | | 27.5 | | | 15.0 | 6.2 |

TABLE C-continued

| | | | | | | | |
|---|---|---|---|---|---|---|---|
| Hydrophilic surfactant (e.g., KOLLIPHOR RH40, KOLLIPHOR EL) | 43.7 | 20.8 | 23.5 | 13.2 | 10.5 | 9.0 | 11.3 |
| Polyglyceryl-10 mono/di-oleate (e.g., CAPROL PGE-860) | | | | | | | 21.5 |
| Other additives (e.g., solidifier, antioxidant, etc.) | 4.6 | q.s | q.s. | 4.7 | 5.1 | 3.0 | 4.5 |
| Ratio of allopregnanolone/Alpha-tocopherol | 1.28 | 0.12 | 0.95 | 0.33 | 0.26 | 0.25 | 0.19 |
| Ratio of allopregnanolone/medium chain monoglyceride | 0.07 | N/A | N/A | N/A | N/A | N/A | N/A |
| Ratio of Alpha-tocopherol/hydrophilic surfactant | 0.06 | 1.55 | 0.17 | 1.40 | 3.08 | 2.44 | 4.20 |

In one embodiment, the oral solid dosage forms of the present disclosure may be formulated to include from about 10 mg to about 600 mg of allopregnanolone which is treated, and a plurality of additives comprising at least one surfactant. In another embodiment, the oral solid dosage form may include about 30 mg to about 500 mg of allopregnanolone which is treated, and a plurality of additives comprising at least one surfactant. In yet a further embodiment, the oral solid dosage form may include about 30 mg to about 400 mg of allopregnanolone which is treated, and a plurality of additives comprising at least one surfactant. In another embodiment, the oral solid dosage form may include about 100 mg to about 400 mg of allopregnanolone which is treated, and a plurality of additives comprising at least one surfactant. In yet another embodiment, the oral solid dosage form may include about 150 mg to about 750 mg of allopregnanolone which is treated, and a plurality of additives comprising at least one surfactant. In yet another embodiment, the oral solid dosage form may include about 30 mg to about 300 mg of allopregnanolone which is treated, and a plurality of additives comprising at least one surfactant. In a further embodiment, the oral solid dosage form may include about 30 mg to about 200 mg of allopregnanolone which is treated, and a plurality of additives comprising at least one surfactant. In a further embodiment, the oral solid dosage form may include about 10 mg, about 15 mg, about 20 mg, about 25 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 350 mg, about 400 mg, about 500 mg, about 550 mg, or about 600 mg of allopregnanolone which is treated, and a plurality of additives comprising at least one surfactant.

The solid form of allopregnanolone in the composition can comprise from 5 wt % to about 60 wt % of the oral solid dosage composition described herein. In one embodiment, the allopregnanolone can comprise from about 10 wt % to about 45 wt % of the oral solid dosage composition. In the compositions and forms of the present invention, the allopregnanolone can be a treated form, such as micronized, nano-sized, and/or in amorphous forms. In another embodiment, the oral solid dosage form may include a combination of these forms. In another embodiment, allopregnanolone may be present or added to the oral solid dosage form comprising at least one surfactant as a treated form such as amorphous, micronized, ultra-micronized, nano-sized, milled, sieved forms, or combinations thereof. Allopregnanolone may be dispersed within the oral solid dosage form. The dispersed portion of allopregnanolone may be partially or completely micronized, ultra-micronized, nano-sized, milled, sieved, amorphous forms or combinations thereof.

The allopregnanolone in the oral solid dosage forms of the present invention can be partially or fully in the form of high-energy solid which increases the release rate in an aqueous medium or absorption significantly as compared to at least one of its unmilled or unmicronized (untreated) crystalline forms (low energy forms). Examples of high-energy (treated) solid forms include amorphous forms, solid dispersion forms, solid solution forms, eutectic forms, and the like. In one embodiment, the high-energy form of allopregnanolone in a composition of present invention may be physicochemically stable. In yet another embodiment the high-energy form of allopregnanolone in a dosage form can be physically and/or chemically associated with at least one additional substance, such as for example alcohol, pyrrolidone, cellulose, poloxamer, polyol, polyethylene glycol, dextrins, cyclodextrins and the like. Several methods known in the art may be used to produce the high-energy form allopregnanolone of the present invention; for example, co-precipitation, solid-solution, co-melting, co-grinding, hot melt extrusion, hot melt spraying, spray drying with co-solvent, controlled precipitation from super-saturated solutions, solidified supersaturated solutions, and combinations thereof.

The oral solid dosage forms of the present disclosure can include a plurality of pharmaceutically acceptable additives. The pharmaceutical additives can be selected from a wide range of compounds and classes of compounds. The pharmaceutically acceptable additives can comprise from 40 wt % to about 99.5 wt % of the oral solid dosage form. In one embodiment, the pharmaceutically acceptable additives can comprise about 50 wt % to 90 wt % of the oral dosage form. In one embodiment, the pharmaceutically acceptable additives can comprise about 50 wt % to 75 wt % of the oral solid dosage form. In yet another embodiment, the pharmaceutically acceptable additives can comprise about 50 wt % to 70 wt % of the oral solid dosage form.

Non-limiting examples of compounds that can be used as at least a part of the pharmaceutically acceptable additives include, without limitation, celluloses; dextrins, gums, carbomers, methacrylates, sugars, lactoses, inorganic carbonates, oxides, chlorides, sulphates; salts of calcium; salts of magnesium; salts of fatty acids; inorganic and organic acids, bases and salts; propylene glycol; glycerols; fatty acids; fatty alcohols; fatty acid esters; glycerol esters; mono-, di- or triglycerides; edible oils; omega oils; vegetable oils, hydrogenated vegetable oils; partially or fully hydrogenated vegetable oils; glycerol esters of fatty acids; waxes; alcohols; sorbitan; gelatin; polyethylene glycol; polyethylene oxide co-polymers; silicates; antioxidants, tocopherols, sugar stearates, starches, shellac, resins, proteins, acrylates; methyl copolymers; polyvinyl alcohol; starch; phthalates; and combinations thereof.

It is important to note that additives in compositions used in the present invention may serve multiple functional purposes within the oral solid dosage form. For example, an additive may also function as a filler, a binder, a diluent, a disintegrant, a lubricant, a glidant, a preservative, a sweetener, a flavor, a coating agent, a colorant, or an antioxidant.

The oral solid dosage form(s) are not limited with respect to size, shape or general configuration, and may be formulated into a variety of the dosage forms including, but not limited to, two piece hard gelatin capsules, soft gelatin capsules, beads, beadlets, granules, spherules, pellets, microcapsules, microspheres, nanospheres, nanocapsules, tablets, or combinations thereof. Other oral solid dosage forms known to those of ordinary skill in the art may also be used. In one aspect, the oral solid dosage form may be a capsule or tablet. In one embodiment, the oral solid dosage form can be a matrix tablet.

The coating may be applied by conventional techniques, such as by pan coaters, rotary granulators and fluidized bed coaters such as top-spray, tangential-spray or bottom-spray (Wurster coating), and most preferably by the latter. One preferred coating solution consists of about 40 wt % EUDRAGIT L30-D55 and 2.5 wt % triethylcitrate in about 57.5 wt % water. This enteric coating solution may be coated onto the core of the oral dosage form using a pan coater. The enteric coating materials listed above may be used to granulate an allopregnanolone containing mixture. The resultant granulate may be filled into capsules or compressed to form tablets or caplets.

Several oral dosage forms comprising solid forms of allopregnanolone are prepared using the components as set forth in Tables D and E. The examples of the oral dosage forms described herein can be prepared generally as solid dosage forms, such as a tablet. In an aspect, the oral dosage forms are prepared by mixing the processing aids and the surfactant with allopregnanolone to form a homogenous powder blend. In another aspect, the amount of surfactant in the composition may be greater than 0.5% (w/w) of the composition. The powder blend can be compressed to form tablets by direct compression or after dry or wet granulation process steps. In case of wet granulation, a solution of binder (e.g., PVP K30) can be used for granulation. The binder solution may optionally contain a portion (or all) of the amount of the surfactant when a surfactant is present in the dosage form. Following granulation, the resultant product can be dried and compressed into tablets.

Solid dosage forms of allopregnanolone can be crystalline and/or non-crystalline or amorphous solid forms. The final allopregnanolone form in the dosage form can be a result of the processing technique employed, such as size reduction coating, spraying, drying, hot melt extrusion, etc. The final form of allopregnanolone in a solid dosage form can be milled, micronized, nanosized, amorphous, a solid solution or dispersion, or a eutectic mixture. The solid dosage form can be in the form of a tablet, or a powder, or a granule, or a pellet.

In one aspect, the oral dosage forms disclosed herein may be formulated with the allopregnanolone treated from the original powder of allopregnanolone. For example, one of the treated allopregnanolone in this invention is the micronized powder of allopregnanolone, which has a particle size distribution of D90<about 20 μm and/or D50 of <15 μm. In another aspect, the oral dosage forms may be prepared for desired release to improve absorption/bioavailability, including processing aids and at least one of surfactants with treated allopregnanolone to form a homogenous powder blend. Table D shows some exemplary oral solid compositions of the present invention comprising treated solid forms of allopregnanolone for immediate release, with any surfactant.

TABLE D

| | Oral solid compositions comprising allopregnanolone | | | | | | | | | | |
|---|---|---|---|---|---|---|---|---|---|---|---|
| | w/w % | | | | | | | | | | |
| Component | D-1 | D-2 | D-3 | D-4 | D-5 | D-6 | D-7 | D-8 | D-9 | D-10 | D-11 |
| allopregnanolone, treated* | 5-45 | 15-40 | 15-30 | 25-35 | 30-40 | 18-33 | 18-33 | 20-30 | 40-50 | 20-30 | 5-15 |
| Surfactant (e.g., polysorbate 80, polyoxyl 40 hydrogenated castor oil, sodium lauryl sulfate, sodium docusate, poloxamer, etc.) | 5-25 | 10-30 | 5-25 | 5-25 | 10-25 | 0-20 | 5-20 | 10-25 | 10-40 | 5-25 | 5-20 |
| Processing aids** | q.s. | q.s. | q.s. | q.s. | q.s. | q.s. | q.s. | q.s. | q.s. | q.s. | q.s. |
| Total | 100% | 100% | 100% | 100% | 100% | 100% | 100% | 100% | 100% | 100% | 100% |

*Treated is defined as grinded, sieved, milled, micronized, ultra-micronized, nanosized, amorphous, or fully solubilized.

**Processing aids may comprise, but not limited to, fillers, binders, diluents, disintegrants, lubricants, glidants, preservatives, sweeteners, flavors, coating agents, colorants, antioxidants, lipophilic additive, water, etc.

TABLE E

Preferred oral solid formulations comprising solid forms of allopregnanolone

| Component | E-1 % | E-2 % | E-3 % | E-4 % | E-5 % | E-6 % | E-7 % | E-8 % |
|---|---|---|---|---|---|---|---|---|
| allopregnanolone, treated† | 19.6 | 9.3 | 22.5 | 11.2 | 19.2 | 37.0 | 33.3 | 40.0 |
| Binder (e.g., Crospovidone)* | | | 9.0 | 9.0 | | | 9.0 | 11.0 |
| Binder (e.g., Croscarmellose sodium)* | 10.0 | 12.8 | | | 12.6 | 6.0 | | |
| Binder (e.g., PEG 6000)* | 25.4 | | | | 15.0 | | | |
| Surfactant (e.g., Poloxamer188, 407) | 10.9 | 16.4 | 10.0 | 10.0 | | 12.0 | 10.0 | 12.0 |
| Surfactant (e.g., Sodium lauryl sulphate)** | | | | | 8.0 | | | |
| Filler (e.g., Microcrystalline cellulose) | | 60.5 | 57.5 | 68.8 | | 44.0 | 46.7 | 36.0 |
| Filler (e.g., Lactose monohydrate) | 32.9 | | | | 44.0 | | | |
| Glidant (e.g., Magnesium stearate)*** | 0.2 | | | | 1.2 | | | 1.0 |
| Lipophilic additive (e.g., Stearic acid)**** | 1.0 | 1.0 | 1.0 | 1.0 | | 1.0 | 1.0 | |
| Processing aids‡ | q.s. | q.s. | q.s. | q.s. | q.s. | q.s. | q.s. | q.s. |

†Treated is defined as grinded, sieved, micronized, ultra-micronized, or nanosized, milled, or amorphous in this table.
*Binder may additionally comprise, but is not limited to, povidone, copovidone, crospovidone, polyvinylpyrrolidone, starch, sucrose, polyethylene glycol, cellulose, lactose, crosscaramellose sodium, and gelatin.
**Surfactant may additionally comprise, but is not limited to, sodium lauryl sulphate, TPGS, cyclodextrin, polysorbate, sodium lauryl ethoxy sulphate, sodium lauryl sulfate, sodium docusate, and hydrogenated polyoxyl castor oil.
***Glidant may additionally comprise, but is not limited to, magnesium carbonate, glyceryl distearate, glyceryl palmitostearate, ascorbyl palmitate, calcium palmitate, starch, and talc.
****Lipophilic additive may additionally comprise, but is not limited to, stearic acid, stearin, glyceryl dibehenate, sodium stearyl fumarate, glyceryl distearate, glyceryl palmitostearate, PEG derivatives, boric acid, and waxes.
‡Processing aids, except the functional component shown in the table, may additionally be added with, but are not limited to, disintegrants, preservatives, sweeteners, flavors, coating agents, colorants, antioxidants, and water.

Table F displays various exemplary oral dosage formulations comprising treated allopregnanolone in order to assess the effect of formulations on solubility, dispersibility, and in vitro release, which may affect the blood levels/bioavailability (or absorption into the body) of allopregnanolone for subjects in need of allopregnanolone therapy.

TABLE F

Oral Dosage Formulations Comprising Allopregnanolone

| Component | F-1 | F-2 | F-3 | F-4 | F-5 | F-6 | F-7 | F-8 | F-9 | F-10 | F-11 | F-12 | F-13 | F-14 |
|---|---|---|---|---|---|---|---|---|---|---|---|---|---|---|
| allopregnanolone, treated* | 3.44 | 10-40 | 9.3 | 3 | 3 | 1 | 1 | 1 | 1 | 0.5 | 0.5 | 3 | 4.2 | 9.3 |
| Glyceryl Monocaprylate | 16.60 | | | | | | | 47 | 70 | | 47.5 | 58.3 | 67.3 | |
| Glyceryl Monocaprylocaprate | 64.76 | | | | | | | | | | | | | |
| Polyoxyl 40 hydrogenated castor oil | 5.00 | | | | | | | 31 | 8 | | 31 | 26.5 | 8 | |
| Alpha-Tocopherol | 10.20 | | | | | | | 21 | 21 | | 21 | 12.2 | 20.5 | |
| Crospovidone | | 9.0 | | | | | | | | | | | | |
| Poloxamer 407 | | 10.0 | | | | | | | | | | | | 0.2 |
| Microcrystalline cellulose | | 30-60 | 76.9 | | | | | | | | | | | 76.6 |
| Crosscaramellose sodium | | | 12.8 | | | | | | | | | | | 12.7 |
| Lipophilic additive (e.g., Stearic acid) | | 1.00 | 1 | | | | | | | | | | | 1 |
| Canola Oil | | | | | 97 | | 99 | | | | | | | |
| Polysorbate 80 | | | | | | 97 | | | | | | | | |
| MIGLYOL 812 | | | | | | | 99 | | | | | | | |
| SBE-β-CD | | | | | | | | | | 25 | | | | |
| Purified Water | — | q.s. | q.s. | — | — | — | — | — | — | 74.5 | — | — | — | q.s. |

*Treated is grinded, sieved, milled, micronized, ultra-micronized, nanosized, amorphous, or fully solubilized. In this example, the allopregnanolone is treated (e.g., D90 ≤ 20 μm).

All active agents (allopregnanolone) comprised in the compositions in this Example were treated (e.g., micronized: D90≤20 μm) before processing for formulation. Formulation F-1 was formulated to form a solubilized form of allopregnanolone in the composition that includes at least one additive with at least one surfactant. Formulation F-2 was formulated to form a crystalline form of allopregnanolone in the composition for immediate release that includes at least one additive with at least one surfactant that was >0.5% w/w of the composition. Formulation F-2 needs to be disintegrated for releasing in vitro or in vivo. Its disintegration time was measured less than about 25 min in vitro. Formulation F-3, F-4, F-5 and F-14 were formulated to test the release rate of allopregnanolone in comparison with the release rates of Formulation F-1 and F-2 of the current invention. Formulation F-3 was formulated to form a crystalline form of allopregnanolone in the composition that does not have any surfactant. Formulation F-4 was formulated to form a suspended crystalline form of allopregnanolone in the composition that essentially includes only edible oil without any surfactant. Formulation F-5 was formulated to form a suspended crystalline form of allopregnanolone in the composition that essentially includes only a surfactant, yet without any additive. Formulation F-14 was formulated to form a crystalline form of allopregnanolone in the composition that had a surfactant that was <0.5% w/w of the composition.

Composition 1

An allopregnanolone, micronized containing composition may be prepared by using a selection of the components set forth in Table 1. The composition is prepared by weighing all the components, except allopregnanolone into a clean stainless-steel container and mixed at about 35° C. to 45° C., using a stirrer. Allopregnanolone is added and stirred until dissolved forming a clear solution. A predetermined quantity of the mixture is disposed into a capsule (for example, hard gelatin capsule) to get the required allopregnanolone dose per dosage unit. The capsules are allowed to cool at room temperature, banded (if required) and packaged in a HDPE bottle and tightly closed with an appropriate lid.

TABLE 1

| | Component (mg/capsule) i |
|---|---|
| Allopregnanolone | 20-50 |
| Lipophilic additives (e.g., Glyceryl monocaprylocaprate, Glyceryl monocaprylate, glycerides of coconut oil, Capmul ® MCM, α-tocopherol, sterol and sterol derivatives, sorbitan fatty acid esters) | 80-510 |
| Hydrophilic additives (e.g., polysorbate 80, polyoxyl 40 hydrogenated castor oil, sodium lauryl sulfate, sodium docusate, poloxamer, polyethylene glycol 1000 tocopherol succinate, PEG 400) | 30-80 |

Allopregnanolone - loading (% wt) of capsule = 3-5%

Referring to Table 1, the oral pharmaceutical composition "i" may be formed to include at least 20 mg of allopregnanolone and at least one additive. By way of example only, "i" may have at least two or more additives, at least three or more additives, or at least four or more additives. By way of example only, each lipophilic additive of the oral pharmaceutical composition "i" may be formed to include about or between 80 mg and 510 mg. By way of additional example, each hydrophilic additive of the oral pharmaceutical composition "i" may be formed to include about or between 30 and 80 mg.

Composition 2

Allopregnanolone, treated (micronized), tablets containing composition was prepared by using the components set forth in Table 2. The tablet composition is prepared weighing a predetermined quantity of allopregnanolone and all the components into a double lined polybag and mixed thoroughly in a tumbling motion for 3 mins. The mixture was granulated with purified water in a dry stainless-steel bowl. The granules were dried at about 25° C. and screened through ASTM mesh #40. Filler additive (e.g., extra-granular microcrystalline cellulose (MCC)), binder additives (e.g., copovidone, crospovidone, sucrose) and lipophilic additives (e.g., sterol and sterol derivatives, stearic acid) were blended with the granules. The final blend was compressed into tablets at a fixed hardness of 8-10 kP to produce tablets of the same target weight (dose) and similar hardness and packaged in a HDPE bottle and tightly closed with an appropriate lid.

TABLE 2

| | Component (mg/tablet) ii |
|---|---|
| Allopregnanolone | 100-300 |
| Binder additive (e.g., povidone, copovidone, crospovidone, polyvinylpyrrolidone, starch, sucrose, polyethylene glycol, cellulose, lactose, crosscaramellose sodium) | 70-90 |
| Hydrophilic additives (e.g., polysorbate 80, polyoxyl 40 hydrogenated castor oil, sodium lauryl sulfate, sodium docusate, poloxamer, polyethylene glycol 1000 tocopherol succinate, PEG 400) | 60-95 |
| Filler additive (Microcrystalline cellulose) | 400-620 |
| Lipophilic additive (e.g., sterol and sterol derivatives, stearic acid) | 8-10 |
| Purified water | qs |

Allopregnanolone - loading (% wt) of tablet = 11-33%

Referring to Table 2, the oral pharmaceutical composition ii may be formed to include at least 25 mg of allopregnanolone and at least one additive. By way of example only, ii may have at least two or more additives, at least three or more additives, at least four or more additives, or at least five or more additives. By way of example only, each binder additive of the oral pharmaceutical composition ii may be formed to include about or between 70 mg and 90 mg. By way of additional example, each hydrophilic additive of the oral pharmaceutical composition ii may be formed to include about or between 30 and 80 mg. By way of additional example, each filler additive of the oral pharmaceutical composition ii may be formed to include about or between 400 and 620 mg. By way of additional example, each lipophilic additive ii of the oral pharmaceutical composition may be formed to include about or between 8 and 10 mg.

Composition 3

An allopregnanolone containing composition can be prepared by using the components set forth in Table 3 as follows: The required quantity of allopregnanolone is suspended in polyethylene glycol (e.g., PEG 4000 or 6000) and Poloxamer 188 at 75° C. The melted solution is sprayed on lactose in a fluid bed Strea-1 at 75° C. The granular product is sieved through sieve 0.7 mm and blended with magnesium stearate in a mixer. The mixture is compressed into 10 mm tablets.

TABLE 3

| | Components (mg/tablet) | | | | |
|---|---|---|---|---|---|
| | iii | iv | v | vi | vii |
| Allopregnanolone | 30 | 30 | 30 | 30 | 30 |
| Polyethylene glycol, PEG 4000 | — | — | 248 | 175 | 236 |
| Polyethylene glycol, PEG 6000 | 175 | 248 | — | — | — |
| Poloxamer 188 | 73 | — | — | 73 | — |
| Lactose | 220 | 220 | 220 | 220 | 220 |
| Sodium lauryl sulfate | — | — | — | — | 12 |
| Magnesium stearate | 2 | 2 | 2 | 2 | 2 |
| Total weight | 500 | 500 | 500 | 500 | 500 |

Allopregnanolone - loading (% wt) of tablet = 6.0%.

An allopregnanolone containing composition can be prepared using the components set forth in Table 3A and a method similar to that described in Composition 3 with higher temperature for melting mixture and compressing to larger tablets.

TABLE 3A

| | Component (w/w %) |
|---|---|
| | viiA |
| Allopregnanolone | 10 |
| Polyethylene glycol, PEG 400 | 8 |
| Polyethylene glycol, PEG 8000 | 18 |
| Methylcellulose | 38 |
| Lactose | 25 |
| Colloidal silicon dioxide | 0.2 |
| Magnesium stearate | 1 |
| Total weight | 100 |

Composition 4

An allopregnanolone containing composition can be prepared using the components set forth in Table 4 and a method similar to that described in Composition 3.

TABLE 4

| | Component (mg/tablet) |
|---|---|
| | viii |
| Allopregnanolone | 22 |
| Polyethylene glycol, PEG 6000 | 27 |
| Poloxamer 188 | 12 |
| Lactose | 38 |
| Magnesium stearate | 1 |
| Total weight | 100 |

Allopregnanolone - loading (% wt) of tablet = 22.0%.

Composition 5

An allopregnanolone containing composition can be prepared using the components set forth in Table 5 and a method similar to that described in Composition 3.

TABLE 5

| | Component (mg/tablet) |
|---|---|
| | ix |
| Allopregnanolone | 33 |
| AEROPERL 300 | 22 |
| Polyethylene glycol, PEG 300 | 44 |
| Magnesium stearate | 1 |
| Total weight | 100 |

Allopregnanolone - loading (% wt) of tablet = 33.0%.

Composition 6

An allopregnanolone containing composition can be prepared using the components set forth in Table 6 and a method similar to that described in Composition 3.

TABLE 6

| | Components (% w/w) | | | |
|---|---|---|---|---|
| | x | xi | xii | xiii |
| Allopregnanolone, micronized | 90-99 | — | — | 64-67 |
| Allopregnanolone (particle size >50 μm) | — | 70-80 | — | — |
| Allopregnanolone, milled | — | — | 70-80 | — |
| Lactose | 1-10 | 1-20 | 3-6 | 3-6 |
| Povidone K30 | 3-6 | 3-6 | 3-6 | 3-6 |
| Granulation solvent (e.g., alcohol) | qs | qs | qs | qs |

Composition 7

An allopregnanolone containing composition can be prepared using the components set forth in Table 7 by wet granulation method as follows: Allopregnanolone, microcrystalline cellulose and croscarmellose sodium are passed through an ASTM mesh #40 mesh sieve and mixed in a low shear granulator to form a uniform blend. A binder solution of Starch 1500 in deionized water can be used to granulate the dry powder blend to a typical granulation end-point. The wet granulate is dried using a tray dryer or fluid air dryer, sized/screened, lubricated with AEROSIL 200 and magnesium stearate, and compressed into tablets.

TABLE 7

| | Component (% w/w) |
|---|---|
| | xiv |
| Allopregnanolone | 28 |
| Microcrystalline cellulose (Avicel PH 102) | 52.5 |
| Croscarmellose sodium | 10 |
| Pregelatinized starch (Starch 1500) | 8 |
| Colloidal silicon dioxide (AEROSIL 200) | 0.5 |
| Magnesium stearate | 1 |
| Total weight | 100 |

Composition 8

Allopregnanolone coated pellets can be prepared using the ingredients set forth in Table 8. As praying solution of the coating materials can be prepared by dissolving a predetermined quantity of allopregnanolone, Pluronic F 68 and PVP K 30 in about 250 mL of dehydrated alcohol. The spray solution can be intermittently sprayed on to a rolling bed of microcrystalline cellulose spheres (for example, having a mean particle size in the range of about 250 µm to 600 µm) taken in a conventional coating pan. After all the spray solution is loaded on the spheres, it can be dried under a gentle current of air for at least 1 hour to remove the solvent. Allopregnanolone loaded pellets or beads can be disposed into a capsule. Auxiliary pharmaceutical process aids such as talc, starch etc., may be dusted during the spraying process to avoid agglomeration of the pellets.

TABLE 8

|  | Component (% w/w) xv |
| --- | --- |
| Allopregnanolone | 25 |
| Pluronic F68 | 6 |
| Polyvinylpyrrolidone | 5 |
| Dehydrated alcohol | 12 |
| Microcrystalline cellulose sphere (CELSPHERE) | 52 |
| Total weight | 100 |

Composition 9

Allopregnanolone tablets can be prepared using the ingredients set forth in Table 9 as follows: Sodium lauryl sulfate and sucrose are dissolved in purified water and the nano-sized allopregnanolone is put into suspension in the mixture obtained for 20 minutes. Following this, the docusate sodium is added while agitating until dissolved. Separately, the lactose is placed into suspension in a fluidized air bed granulator and heated to a temperature of 40° C. The allopregnanolone suspension is sprayed onto the lactose. The granulate thus obtained is mixed with crospovidone, microcrystalline cellulose, and magnesium stearate. The material obtained is sieved through sieve no. 300 and blend within a mixer, and the powder mixture is compressed into tablets.

TABLE 9

|  | Component (% w/w) xvi |
| --- | --- |
| Allopregnanolone | 46.3 |
| Sucrose | 14.0 |
| Sodium lauryl sulfate | 1.0 |
| Docusate sodium | 0.2 |
| Lactose | 12.6 |
| Microcrystalline cellulose | 13.8 |
| Crospovidone | 12.0 |
| Magnesium stearate | 0.1 |
| Total weight | 100 |

Composition 10

An allopregnanolone tablet containing composition can be prepared using the components set forth in Table 10 and a method similar to that described in Composition 9.

TABLE 10

| Composition 10 | Component (% w/w) xvii |
| --- | --- |
| Allopregnanolone | 22.3 |
| Sucrose | 22.3 |
| Hypromellose | 4.5 |
| Sodium lauryl sulfate | 1.6 |
| Docusate sodium | 0.5 |
| Lactose | 20.3 |
| Microcrystalline cellulose | 13.2 |
| Crospovidone | 11.6 |
| Magnesium stearate | 0.1 |
| Opadry ® Complete Film Coating | 3.8 |
| Total weight | 100 |

Composition 11

Allopregnanolone tablets can be prepared using the ingredients set forth in Table 11 as follows: A predetermined quantity of allopregnanolone is dissolved in a mixed solution of polyethylene glycol 6000 and Poloxamer 188 (70:30 w/w ratio) at 75° C. About 240 g of the melted solution is sprayed on 200 g lactose in a fluid bed at 75° C. The granulate thus obtained is sieved through sieve no. 300 and blend with magnesium stearate within a mixer. The powder mixture is compressed into tablets.

TABLE 11

|  | Component (% w/w) xviii |
| --- | --- |
| Allopregnanolone | 9.3 |
| Lactose | 44.8 |
| PEG 6000 | 31.8 |
| Poloxamer 188 | 13.6 |
| Magnesium stearate | 0.5 |
| Total weight | 100 |

Composition 12

An allopregnanolone containing composition can be prepared using the components set forth in Table 12 by self-emulsifying drug delivery systems (SEDDS) followed by incorporation of the liquid SEDDS into an inert solid carrier to produce a solid dosage form as follows: Allopregnanolone is dissolved in the mixture of an oil (e.g., Castor oil, LABRAFIL M 2125, Capmul MCM, PECEOL, MAISINE 35-1), a surfactant (e.g., Tween 80, LABRASOL, LABRAFAC CM 19, Cremophor), and a cosolvent (e.g., Capryol, Lauroglycol) at 60° C. in an isothermal water bath. The final mixture is mixed by creating a vortex until a clear solution is obtained. The formulation is sequilibrated at 40° C. in an incubator shaker for at least 48 hours. The liquid formulation is either disposed into a capsule (for example, soft gelatin capsule) to get the required allopregnanolone dose per dosage unit or lubricated with AEROSIL 200 and magnesium stearate with continuous mixing to prevent any lump formation. The free-flowing powder obtained at the end of the mixing process is sieved through sieve no. 300, blend within a mixer, and the powder mixture is compressed into tablets.

TABLE 12

| Component | (% w/w) xix |
|---|---|
| Allopregnanolone | 10-30 |
| Castor oil | 5-40 |
| Tween 80 | 30-60 |
| Capryol | 0-25 |
| Colloidal silicon dioxide (AEROSIL 200) | 0.5 |
| Magnesium stearate | 1 |
| Total weight | 100 |

Composition 13—Allopregnanolone Composition

Tablets of allopregnanolone containing composition can be prepared using the components set forth in Table 13 and a method similar to that described in Composition 12.

TABLE 13

| Component | (% w/w) xx |
|---|---|
| Allopregnanolone, drug load | 83* |
| Hydroxypropyl cellulose | 9 |
| Croscarmellose sodium | 6 |
| Magnesium stearate | 1 |
| Talc | 1 |
| Total weight | 100 |

*Drug loaded solid self-nanoemulsifying drug delivery system consisting of oil (glycerol triacetate, 55 mg/mL), surfactant (Tween 80, 100 mg/mL), and cosurfactant (PEG 200, 200 mg/mL).

Composition 14

An allopregnanolone capsule containing composition can be prepared using the components set forth in Table 14 and a method similar to that described in Composition 12. The liquid formulation is disposed into a capsule (for example, soft gelatin capsule) to get the required allopregnanolone dose per dosage unit. The capsules are allowed to cool at room temperature, banded (if required) and packaged in a HDPE bottle and tightly closed with an appropriate lid.

TABLE 14

| Component | (% w/w) xxi |
|---|---|
| Allopregnanolone | 30 |
| Oleic Acid | 55 |
| Polyoxyl 40 Hydrogenated Castor Oil | 4 |
| Stearic Acid | 4 |
| Glyceryl Palmitostearate | 6.5 |
| Ascorbyl Palmitate | 0.5 |
| Total weight | 100.0 |

Composition 15

An allopregnanolone capsule containing composition can be prepared using the components set forth in Table 15 and a method similar to that described in Composition 12.

TABLE 15

| Component | (% w/w) xxii |
|---|---|
| Allopregnanolone | 30 |
| Corn oil, mono-, di-, tri-glycerides | 60 |
| Polyoxyl 40 Hydrogenated Castor Oil | 5 |
| Propylene glycol | 3 |
| alpha-Tocopherol | 5 |
| Total weight | 100 |

Composition 16

An allopregnanolone capsule containing composition can be prepared using the components set forth in Table 16 and a method like that described in Composition 12.

TABLE 16

| Component (% w/w) | xxiii | xxiv | xxv | xxvi |
|---|---|---|---|---|
| Allopregnanolone | 30 | 30 | 30 | 30 |
| LABRAFIL | 23 | 23 | — | — |
| LABRAFAC | — | — | 23 | 23 |
| Cremophor RH40 | 23 | — | 23 | — |
| Cremophor EL | — | 23 | — | 23 |
| Propylene glycol | 24 | 24 | 24 | 24 |
| Total weight | 100 | 100 | 100 | 100 |

Composition 17

An allopregnanolone capsule containing composition can be prepared using the components set forth in Table 17 according to the follow procedure: The required quantities of the inactive components and allopregnanolone are quantitatively transferred into a clean stainless-steel container and mixed gently at about 60° C. using a stirrer to obtain a homogenous mixture. A predetermined weight of the resulting mixture is disposed into a hard gelatin capsule and allowed to solidify at room temperature.

TABLE 17

| Component (% w/w) | xxvii | xxviii | xxix |
|---|---|---|---|
| Allopregnanolone | 75 | 34 | 60 |
| Polyethylene glycol 8000 | 10 | 29 | 40 |
| Sodium lauryl sulfate | 10 | — | — |
| Povidone K30 | 5 | 37 | — |
| Total weight | 100 | 100 | 100 |

Composition 18

Allopregnanolone capsule containing composition can be prepared using the ingredients set forth in Table 18 as follows: Allopregnanolone is slowly added to a molten mixture of Gelucire (44/14) and Carbowax 20,000 at 85° C., and the mixture is thoroughly mixed to obtain a homogenous solution. Hydroxypropyl cellulose is added to the homogenous solution and agitated for about 20 minutes. The resulting mixture is disposed into a hard gelatin capsule using a liquid filling capsule machine with dosing pumps heated at 85° C. The capsules are allowed to cool at room temperature, banded (if required) and packaged in a HDPE bottle and tightly closed with an appropriate lid.

TABLE 18

| | Component (% w/w) | |
|---|---|---|
| | xxx | xxxa |
| Allopregnanolone | 30 | 36 |
| Lauroyl polyoxyl-32 glycerides (Gelucire ® 44/14) | 46 | 32 |
| Poloxamer 407 | — | 32 |
| Carbowax 20,000 | 9 | — |
| Hydroxypropyl cellulose | 15 | — |
| Total weight | 100 | 100 |

Composition 19

Allopregnanolone capsule containing composition can be prepared using the ingredients set forth in Table 19 as follows: The allopregnanolone is mixed with sodium lauryl sulfate and micronized in an air-jet to give a powder with a median particle size of 3-5 µm. Lactose and pregelatinized starch are added to this powder and the whole is converted to granules in the presence of 9% of distilled water, relative to the total weight of the mixture. The granulate thus obtained is dried for about 24 hours at 50° C. and subsequently graded to retain only the particles with sizes less than or equal to 1000 µm. Crosslinked polyvinylpyrrolidone (PVP) and Magnesium stearate are then added, and the resulting mixture is homogenized in a mixer. The resulting powder is disposed into a hard gelatin capsule on an automatic machine with the compression set to a maximum of 150N, banded (if required) and packaged in a HDPE bottle and tightly closed with an appropriate lid.

TABLE 19

| | Component (mg/capsule) | | | | |
|---|---|---|---|---|---|
| | xxxi | xxxii | xxxiii | xxxiv | xxxv |
| Allopregnanolone | 100 | 100 | 100 | 100 | 100 |
| Sodium lauryl sulfate | 3.5 | 8.0 | — | 1.5 | 13 |
| Lactose | 50.5 | 54 | 54 | 52.5 | 41 |
| Pregelatinized starch | 15 | 7.5 | 15 | 15 | 15 |
| Crosslinked polyvinylpyrrolidone | 3.5 | 3.0 | 3.5 | 3.5 | 3.5 |
| Magnesium stearate | 2.5 | 2.5 | 2.5 | 2.5 | 2.5 |
| Total weight | 175 | 175 | 175 | 175 | 175 |

Allopregnanolone-loading (% wt) of capsule fill = 57.1%

Composition 20

Allopregnanolone capsule containing composition can be prepared using the ingredients set forth in Table 20 as follows: The composition is prepared by weighing the listed components, except the allopregnanolone, into a clean stainless-steel container and mixed at about 50-70° C. under constant stirring with a stirrer. The allopregnanolone is added into the solution and stir until it complete dissolves. A predetermined quantity of the resulting mixture is disposed into a capsule (e.g., gelatin capsule) to obtain the required allopregnanolone dose per dosage unit. The capsules are allowed to cool at room temperature, banded (if required) and packaged in a HDPE bottle and tightly closed with an appropriate lid.

TABLE 20

| | Component (mg/capsule) |
|---|---|
| | xxxvi |
| Allopregnanolone | 100 |
| Glycerides of coconut oil; Capmul MCM | 360 |
| Propylene glycol monolaurate (Lauroglycol ™) | 150 |
| Cremophor ® RH40 | 25 |
| Total weight | 635 |

Allopregnanolone-loading (% wt) of capsule fill = 15.7%

Example 2. Oral Dosage Formulations Comprising Untreated allopregnanolone

Oral compositions comprising crystalline forms of untreated allopregnanolone is expected to have a slower rate and extent of allopregnanolone absorption one possibly due to particle size distribution of allopregnanolone in the compositions pre or post formulation processing. Table G displays various exemplary oral dosage formulations comprising untreated allopregnanolone.

TABLE G

| | w/w % | | |
|---|---|---|---|
| Component | G #1 % | G #2 % | G #3 % |
| allopregnanolone, untreated* | 34.0 | 34.0 | 34.0 |
| Surfactant (e.g., Poloxamer 407)† | 10.0 | 0.3 | — |
| Binder (e.g., Crospovidone) | 9.0 | 9.0 | 9.0 |
| Filler (e.g., Microcrystalline cellulose) | 46.0 | 55.7 | 56.0 |
| Lipophilic additive (e.g., Stearic acid) | 1.0 | 1.0 | 1.0 |
| Processing aids | q.s. | q.s. | q.s. |

*Untreated has D10 > 20 µm and D50 > 55 µm.

Example 3. PK Values of Oral Compositions of Allopregnanolone

Exemplary oral compositions 3A and 3B were made, and a single dose of different dose concentrations was administered to subjects with serum drug blood levels monitored over a 24 hour period. Composition 3A may be prepared as 54 mg and 81 mg doses, in a manner substantially similar to the method described for Composition 1 in relation to Table 1. Composition 3A may be prepared to have 3.44% allopregnanolone (% w/w). Composition 3A may be administered as a 54 and 81 mg dose in the fed state and an 81 mg dose may be administered in the fasted state as well. Composition 3B may be prepared as 100 mg and 300 mg doses, in a manner substantially similar to the method described for Composition 2 in relation to Table 2. Composition 3B may have 11.24% allopregnanolone (% w/w) for the 100 mg tablet and 33.33% for the 300 mg tablet. Composition 3B may be administered as a 100 mg tablet and 300 mg tablet in the fasted state and a 300 mg tablet may be administered in the fed state as well. A comparison of example single dose oral pharmaceutical compositions is shown below in Table 21. This table identifies the formulation, amount of allopregnanolone (dose) administered, the food state the subjects were in (food state), PK parameters $C_{max}$, dose normalized $C_{max/dose}$, the $C_{max}$ is observed ($T_{max}$), $AUC_{0-24}$, and dose normalized $AUC_{0-24/dose}$.

TABLE 21

Observed PK parameters for exemplary compositions formulations upon oral administration

| Composition | Dose mg | Prandial status | $C_{max}$ ng mL$^{-1}$ | $C_{max/dose}$ ng mL$^{-1}$ mg$^{-1}$ | $T_{max}$ h | $AUC_{0-24}$ ng h mL$^{-1}$ | $AUC_{0-24/dose}$ ng h mL$^{-1}$ mg$^{-1}$ |
|---|---|---|---|---|---|---|---|
| 3A | 54 | fed | 10.3 | 0.19 | 5 | 43.2 | 0.80 |
| 3A | 81 | fed | 12.5 | 0.15 | 6 | 76.6 | 0.95 |
| 3A | 81 | fasted | 21.1 | 0.26 | 1 | 74.6 | 0.92 |
| 3B | 100 | fasted | 13.4 | 0.13 | 2.5 | 71.9 | 0.72 |
| 3B* | 300 | fasted | 54.9 | 0.18 | 2 | 381.3 | 1.27 |
| 3B | 300 | fed | 47.9 | 0.16 | 5 | 312.6 | 1.04 |

*data was from one subject

Referring to Table 21, PK parameters for formulations 3A and 3B are calculated to contrast PK parameters $AUC_{0-24}$, (area under the curve measured from time 0 hour to 24 hour) $AUC_{0-24/dose}$, $C_{max}$, $C_{max/dose}$, and $T_{max}$. Composition 3A is a non-aqueous, cyclodextrin free, encapsulated form of allopregnanolone and composition 3B are solid dosage forms (also non-aqueous and cyclodextrin free) comprising treated allopregnanolone.

A previous attempt in the prior art (See ZULRESSO Multi-discipline Review at https://www.accessdata.fda.gov/) to provide an oral administration that included allopregnanolone, herein referred to as PA1, as an aqueous solution form at a dose of 30 mg (5 mg/ml concentration) that included 250 mg/ml SBE-β-CD. The PK of PA1 was reported both in fed and fasted states. The $C_{max}$ and $C_{max/dose}$ for the fasted state were 9.1 ng mL$^{-1}$ and 0.30 ng mL$^{-1}$ mg$^{-1}$ respectively, and the $AUC_{0-24}$ and $AUC_{0-24/dose}$ for the fasted state were 17.4 ng h mL$^{-1}$ and 0.58 ng h mL$^{-1}$ mg$^{-1}$ respectively. The $C_{max}$ and $C_{max/dose}$ for the fed state were 3.9 ng mL$^{-1}$ and 0.13 ng mL$^{-1}$ mg$^{-1}$ respectively, and the $AUC_{0-24}$ and $AUC_{0-24/dose}$ for the fed state were 14.3 ng h mL$^{-1}$ and 0.48 ng h mL$^{-1}$ mg$^{-1}$ respectively. The food sensitivity ratio of $C_{max}$ for fasted:fed (fasted to fed) of PA1 is 2.3:1.

Referring to Table 21, the food sensitivity ratio of $C_{max}$ for fasted:fed (fasted to fed) for 3A is 1.7:1, showing a lower food sensitivity for use of the 3A when compared to the PA1 composition.

Through the oral pharmaceutical compositions or dosage forms exemplified in the present invention, modulation to the composition or form of comprised allopregnanolone to provide effective $AUC_{0-24}$ or higher $AUC_{0-24S}$ while relatively robust with respect to food sensitivity.

Composition 3A shows a benefit over PA1 compositions in lacking food sensitivity with both the $C_{max}$ for fasted:fed as 1.7:1. Furthermore, $AUC_{0-24}$ of 3A in the fed state may be equal to or greater than about 15 ng h mL$^{-1}$; greater than about 17 ng h mL$^{-1}$; greater than about 18 ng h mL$^{-1}$; greater than about 19 ng h mL$^{-1}$; greater than about 20 ng h mL$^{-1}$; greater than about 30 ng h mL$^{-1}$; greater than about 40 ng h mL$^{-1}$; greater than about 50 ng h mL$^{-1}$; greater than about 75 ng h mL$^{-1}$; greater than about 100 ng h mL$^{-1}$; greater than about 125 ng h mL$^{-1}$; greater than about 150 ng h mL$^{-1}$; greater than about 200 ng h mL$^{-1}$; greater than about 250 ng h mL$^{-1}$; greater than about 300 ng h mL$^{-1}$. Enhancement to $AUC_{0-24/dose}$ may also be realized through composition 3A for fasted and fed states over cyclodextrin compositions (PA1). For example, in the fed state 3A compositions may achieve $AUC_{0-24/dose}$ values greater than about 0.48 h/L. Similarly, in the fasted state, 3A compositions may achieve $AUC_{0-24/dose}$ values greater than about 0.58 h/L. Composition 3A may achieve $AUC_{0-24/dose}$ values greater than about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L.

Furthermore, consistent with the described sensitivity to food for PA1 (and lack of sensitivity for 3A), enhancement to $C_{max}$ for 3A compositions may be at least one of about 4.25 ng/mL, about 4.50 ng/mL, about 4.75 ng/mL, about 5.00 ng/mL, about 5.25 ng/mL, about 5.50 ng/mL, and about 6.00 ng/mL through composition 3A for fed state, and $C_{max}$ may be at least one of about 9.50 ng/mL, about 14.50 ng/mL, about 20.00 ng/mL, and about 25.00 ng/mL for 3A compositions in a fasted state. Similarly, $C_{max/dose}$ of 3A compositions may be greater than 0.13 ng mL$^{-1}$ mg$^{-1}$, about 0.14 ng mL$^{-1}$ mg$^{-1}$, about 0.16 ng mL$^{-1}$ mg$^{-1}$, about 0.18 ng mL$^{-1}$ mg$^{-1}$, about 0.20 ng mL$^{-1}$ mg$^{-1}$, about 0.22 ng mL$^{-1}$ mg$^{-1}$, about 0.24 ng mL$^{-1}$ mg$^{-1}$, and about 0.26 ng mL$^{-1}$ mg$^{-1}$ through 3A compositions for fed state, and $C_{max/dose}$ may be less than about 0.30 ng mL$^{-1}$ mg$^{-1}$, about 0.28 ng mL$^{-1}$ mg$^{-1}$, about 0.26 ng mL$^{-1}$ mg$^{-1}$, about 0.24 ng mL$^{-1}$ mg$^{-1}$, about 0.22 ng mL$^{-1}$ mg$^{-1}$, about 0.20 ng mL$^{-1}$ mg$^{-1}$, about 0.18 ng mL$^{-1}$ mg$^{-1}$, about 0.16 ng mL$^{-1}$ mg$^{-1}$, about 0.14 ng mL$^{-1}$ mg$^{-1}$, about 0.13 ng mL$^{-1}$ mg$^{-1}$, and about 0.12 ng mL$^{-1}$ mg$^{-1}$ for fasted state.

Composition 3B comprising allopregnanolone in a form in a solid dosage composition, shows a benefit over PA1 and additionally over composition 3A in lacking food sensitivity with the $C_{max}$ for fasted:fed as 1.1:1. This is a surprising and unexpected result as food sensitivity with increased blood level drug exposure ($C_{max}$ for fasted:fed as <1:1) is typically expected for a poorly water soluble solid form drug (e.g., allopregnanolone) composition. Furthermore, exemplary innovative composition 3B, comprising allopregnanolone in a form in a solid dosage composition, may allow for higher drug serum level ($AUC_{0-24}$ and $C_{max}$) without limitation(s) of the PA1. $AUC_{0-24}$ of 3B in the fed state may be equal to or greater than about 15 ng h mL$^{-1}$; greater than about 17 ng h mL$^{-1}$; greater than about 18 ng h mL$^{-1}$; greater than about 19 ng h mL$^{-1}$; greater than about 20 ng h mL$^{-1}$; greater than about 30 ng h mL$^{-1}$; greater than about 40 ng h mL$^{-1}$; greater than about 50 ng h mL$^{-1}$; greater than about 75 ng h mL$^{-1}$; greater than about 100 ng h mL$^{-1}$; greater than about 125 ng h mL$^{-1}$; greater than about 150 ng h mL$^{-1}$; greater than about 200 ng h mL$^{-1}$; greater than about 250 ng h mL$^{-1}$; greater than about 300 ng h mL$^{-1}$. Enhancement to $AUC_{0-24/dose}$ may also be realized through solid dosage compositions of this invention (e.g., 3B) for fasted and fed states over cyclodextrin compositions (e.g., PA1). For example, in the fed state, solid dosage compositions may achieve $AUC_{0-24/dose}$ values greater than about 0.48 h/L. Similarly, in the fasted state, solid dosage compositions may achieve $AUC_{0-24/dose}$ values greater than about 0.58 h/L.

Composition 3B may achieve $AUC_{0-24/dose}$ values greater than about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L.

Furthermore, consistent with the described sensitivity to food for PA1 (and lack of sensitivity for 3B), enhancement to $C_{max}$ for solid dosage compositions may be at least one of about 4.25 ng/mL, about 4.50 ng/mL, about 4.75 ng/mL, about 5.00 ng/mL, about 5.25 ng/mL, about 5.50 ng/mL, and about 6.00 ng/mL through solid dosage compositions for fed state, and $C_{max}$ may be at least one of about 9.50 ng/mL, about 14.50 ng/mL, about 20.00 ng/mL, and about 25.00 ng/mL for solid dosage composition in a fasted state. Similarly, dose normalized $C_{max/dose}$ of solid dosage compositions may be greater than 0.13 ng mL$^{-1}$ mg$^{-l}$, about 0.14 ng mL$^{-1}$ mg$^{-l}$, about 0.16 ng mL$^{-1}$ mg$^{-l}$, about 0.18 ng mL$^{-1}$ mg$^{-l}$, about 0.20 ng mL$^{-1}$ mg$^{-1}$, about 0.22 ng mL$^{-1}$ mg$^{-l}$, about 0.24 ng mL$^{-1}$ mg$^{-l}$, and about 0.26 ng mL$^{-1}$ mg$^{-1}$ through solid dosage compositions for fed state, and $C_{max/dose}$ may be less than about 0.30 ng mL$^{-1}$ mg$^{-1}$, about 0.28 ng mL$^{-1}$ mg$^{-l}$, about 0.26 ng mL$^{-1}$ mg$^{-l}$, about 0.24 ng mL$^{-1}$ mg$^{-l}$, about 0.22 ng mL$^{-1}$ mg$^{-l}$, about 0.20 ng mL$^{-1}$ mg$^{-l}$, about 0.18 ng mL$^{-1}$ mg$^{-l}$, about 0.16 ng mL$^{-1}$ mg$^{-l}$, about 0.14 ng mL$^{-1}$ mg$^{-l}$, about 0.13 ng mL$^{-1}$ mg$^{-l}$, and about 0.12 ng mL$^{-1}$ mg$^{-1}$ for fasted state.

In another aspect, the compositions comprising allopregnanolone disclosed herein may be in a form that provides a therapeutically effective amount/blood levels of allopregnanolone for treating the CNS disorder in the subject. In yet another aspect, the allopregnanolone can be combined with a plurality of additives comprising at least one lipophilic additive that is sufficient to provide a therapeutically effective amount/blood levels of allopregnanolone for treating the CNS disorder in the subject. In another aspect, the allopregnanolone can be combined with a plurality of additives comprising at least one surfactant that is sufficient to provide a therapeutically effective amount/blood levels of allopregnanolone for treating the CNS disorder in the subject. In one aspect, the composition is a solid dosage form or a non-liquid dosage form. In another aspect, the allopregnanolone form in the composition of starting form of allopregnanolone composition is a solid form or a solid crystalline form or a non-fully solubilized form.

In one aspect, the therapeutically effective amount of allopregnanolone can provide a $C_{max}$ and/or $AUC_{0-24}$ that is adequate or sufficient or required to treat the CNS disorder.

In another aspect, the therapeutically effective amount of allopregnanolone can provide a $C_{max}$ of allopregnanolone with minimum of about 9.50 ng/mL, about 9.50 ng/mL, about 14.50 ng/mL, about 20.00 ng/mL, and about 25.00 ng/mL.

Also, in yet another embodiment, the therapeutically effective amount of allopregnanolone can provide a dose normalized maximum $C_{max}$ of at least one of about 0.28 ng mL$^{-1}$ mg$^{-l}$, about 0.26 ng mL$^{-1}$ mg$^{-l}$, about 0.24 ng mL$^{-1}$ mg$^{-l}$, about 0.22 ng mL$^{-1}$ mg$^{-1}$, about 0.20 ng mL$^{-1}$ mg$^{-l}$, about 0.18 ng mL$^{-1}$ mg$^{-l}$, about 0.16 ng mL$^{-1}$ mg$^{-l}$, about 0.14 ng mL$^{-1}$ mg$^{-l}$, about 0.13 ng mL$^{-1}$ mg$^{-l}$, and about 0.12 ng mL$^{-1}$ mg$^{-1}$. In another aspect, the therapeutically effective amount of allopregnanolone can provide a minimum $C_{max}$ of allopregnanolone of at least one of about 9.5 ng/mL, and or a dose normalized maximum $C_{max}$ of at least one of about 0.28 ng mL$^{-1}$ mg'. In one aspect the minimum threshold for $C_{max}$ and/or dose normalized $C_{max}$ are achieved through composition and methods of this invention wherein the composition is a solid dosage form or a non-liquid dosage form or an encapsulated liquid dosage form or a cyclodextrin free liquid dosage form or a non-aqueous liquid dosage form or dosage form comprising less than 250 mg/ml or mg/g cyclodextrin. In another aspect the minimum threshold for $C_{max}$ and/or dose normalized $AUC_{0-24}$ are achieved through composition comprising allopregnanolone form in the composition wherein the starting form of allopregnanolone for formulation or process or post formulation/processing is substantially in a solid form or a solid crystalline form or an encapsulated fully solubilized form or substantially non aqueous solubilized form or aqueous solubilized form without a cyclodextrin or solid/solubilized form with less than 250 mg/ml or mg/g cyclodextrin. In another aspect, the minimum threshold for $C_{max}$ and/or dose normalized $C_{max}$ is achieved through orally administering composition without regard to food/meal or in fasted state.

In another embodiment, the therapeutically effective amount of allopregnanolone can provide a minimum $AUC_{0-24}$ of allopregnanolone of at least one of about 18 ng*h/mL, about 19 ng*h/mL, and about 20 ng*h/mL. Also, in yet another embodiment, the therapeutically effective amount of allopregnanolone can provide a dose normalized minimum $AUC_{0-24}$ of at least one of about 0.60 h/L, 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L. In another aspect, the therapeutically effective amount of allopregnanolone can provide a minimum $AUC_{0-24}$ of allopregnanolone of at least one of about 18 ng*h/mL, and or a dose normalized minimum $AUC_{0-24}$ of at least one of about 0.65 h/L. In one aspect the minimum threshold for $AUC_{0-24}$ and/or dose normalized $AUC_{0-24}$ are achieved through composition and methods of this invention wherein the composition is a solid dosage form or a non-liquid dosage form or an encapsulated liquid dosage form or a cyclodextrin free liquid dosage form or a non-aqueous liquid dosage form or dosage form comprising less than 250 mg/ml or mg/g cyclodextrin.

In another aspect the minimum threshold for $AUC_{0-24}$ and/or dose normalized $AUC_{0-24}$ are achieved through composition comprising allopregnanolone form in the composition wherein the starting form of allopregnanolone for formulation or process or post formulation/processing is substantially in a solid form or a solid crystalline form or an encapsulated fully solubilized form or substantially non aqueous solubilized form or aqueous solubilized form without a cyclodextrin or solid/solubilized form with less than 250 mg/ml or mg/g cyclodextrin. In another aspect, the minimum threshold for $AUC_{0-24}$ and/or dose normalized $AUC_{0-24}$ are achieved through orally administering composition without regard to food/meal.

While certain illustrative embodiments have been described in connection with the figures and examples, those of ordinary skill in the art will recognize and appreciate that embodiments encompassed by the disclosure are not limited to those embodiments explicitly shown and described herein. Rather, many additions, deletions, and modifications to the embodiments described herein may be made without departing from the scope of embodiments encompassed by the disclosure, such as those hereinafter claimed, including legal equivalents. In addition, features from one disclosed embodiment may be combined with features of another disclosed embodiment while still being encompassed within the scope of the disclosure.

What is claimed is:

1. An oral pharmaceutical composition for use in treating a CNS disorder, said composition comprising at least about 3% w/w of allopregnanolone, at least about 7% w/w of a hydrophilic additive, and at least about 0.9% w/w of a lipophilic additive,
   wherein said hydrophilic additive comprises at least one of polysorbate 80, polyoxyl 40 hydrogenated castor oil, sodium lauryl sulfate, sodium docusate, polyethylene glycol 1000 tocopherol succinate, PEG 400, and a poloxamer, and
   wherein said lipophilic additive comprises at least one of glyceryl monocaprylate, glyceryl monocaprylocaprate, α-tocopherol, sterol, a sterol derivative, stearic acid, a glyceride of coconut oil, and a sorbitan fatty acid ester, and
   wherein administration of said composition to a subject results in said subject at least one of:
   a dose normalized minimum $AUC_{0-24}$ of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L, and
   a minimum $AUC_{0-24}$ of at least one of about 18 ng*h/mL, about 19 ng*h/mL, and about 20 ng*h/mL.

2. The composition of claim 1, wherein when said subject is in a fasting state, administration of said composition to said subject results in said subject at least one of:
   a dose normalized maximum $C_{max}$ of at least one of about 0.28 ng $mL^{-1}$ $mg^{-1}$, about 0.26 ng $mL^{-1}$ $mg^{-1}$, about 0.24 ng $mL^{-1}$ $mg^{-1}$, about 0.22 ng $mL^{-1}$ $mg^{-1}$, about 0.20 ng $mL^{-1}$ $mg^{-1}$, about 0.18 ng $mL^{-1}$ $mg^{-1}$, about 0.16 ng $mL^{-1}$ $mg^{-1}$, about 0.14 ng $mL^{-1}$ $mg^{-1}$, about 0.13 ng $mL^{-1}$ $mg^{-1}$, and about 0.12 ng $mL^{-1}$ $mg^{-1}$, and
   a minimum $C_{max}$ of at least one of about 9.50 ng/mL, about 14.50 ng/mL, about 20.00 ng/mL, and about 25.00 ng/mL,
   and wherein when said subject is in a fed state, administration of said composition to said subject results in said subject at least one of:
   a dose normalized minimum $C_{max}$ in said subject of at least one of about 0.14 ng $mL^{-1}$ $mg^{-1}$, about 0.16 ng $mL^{-1}$ $mg^{-1}$, about 0.18 ng $mL^{-1}$ $mg^{-1}$, about 0.20 ng $mL^{-1}$ $mg^{-1}$, about 0.22 ng $mL^{-1}$ $mg^{-1}$, about 0.24 ng $mL^{-1}$ $mg^{-1}$, and about 0.26 ng $mL^{-1}$ $mg^{-1}$, and
   a minimum $C_{max}$ in said subject of at least one of about 4.25 ng/mL, about 4.50 ng/mL, about 4.75 ng/mL, about 5.00 ng/mL, about 5.25 ng/mL, about 5.50 ng/mL, and about 6.00 ng/mL.

3. The composition of claim 1, wherein when said subject is in a fasting state, administration of said composition to said subject results in a $T_{max}$ of allopregnanolone in said subject of at least one of less than about 1.5 hours, less than about 2 hours, less than about 3 hours, and less than about 4 hours post-administration; and
   wherein when said subject is in a fed state, administration of said composition to said subject results in a $T_{max}$ of allopregnanolone in said subject of at least one of less than about 1.5 hours, less than about 2 hours, less than about 3 hours, and less than about 4 hours post-administration.

4. The composition of claim 1, wherein said results occur regardless of a fed or fasting state of said subject.

5. The composition of claim 1, wherein said allopregnanolone comprises at least one of a solid form and a non-solid form.

6. The composition of claim 1, wherein said hydrophilic additive comprises a hydrophilic surfactant having an HLB value of at least about 10, and wherein said lipophilic additive comprises a lipophilic surfactant having an HLB value of less than about 10.

7. The composition of claim 1, wherein a dose of said administration comprises at least one of about 10 mg to about 1200 mg of allopregnanolone, about 20 mg to about 600 mg of allopregnanolone, about 30 mg to about 400 mg of allopregnanolone, about 40 mg to about 300 mg of allopregnanolone, about 50 mg to about 250 mg of allopregnanolone, and about 60 mg to about 180 mg of allopregnanolone.

8. The composition of claim 7, wherein said dose comprises at least one of a QD dose, a BID dose, a TID dose, a QID dose, and a more than QID dose.

9. The composition of claim 1, wherein when said CNS disorder comprises a major depression disorder comprising at least one of post/peri partum depression, post-menopausal depression, and essential tremor, a dose of said administration comprises at least one of about 10 mg to about 1200 mg of allopregnanolone and about 60 mg to about 400 mg of allopregnanolone, and
   wherein when said CNS disorder comprises GAD, a dose of said administration comprises at least one of about 10 mg to about 1200 mg of allopregnanolone and about 60 mg to about 180 mg of allopregnanolone, and
   wherein when said CNS disorder comprises OCD, a dose of said administration comprises at least one of about 10 mg to about 1200 mg of allopregnanolone and about 60 mg to about 180 mg of allopregnanolone.

10. The composition of claim 1, wherein said composition comprises at least one form of a solid, liquid, a semi-liquid or semi solid, gel, a granule, a pellet, a powder, a syrup, an emulsion, a dispersion, a suspension, a capsule, a sprinkle, a tablet, a chew, a cream, an ointment, a paste, and a drink.

11. The composition of claim 10, wherein said composition comprises a plurality of instances of said form.

12. The composition of claim 1, wherein said CNS disorder comprises at least one of sleep disorders, mood disorders, essential tremors, depression, dysthymic disorder, bipolar disorder, anxiety disorders, stress, posttraumatic stress disorder (PTSD), compulsive disorders, schizophrenia spectrum disorders, convulsive disorders, seizures, disorders of memory, disorders of and/or cognition, dementia, movement disorders, personality disorders, autism spectrum disorders (ASD), pain, traumatic brain injury (TBI), vascular diseases, substance abuse disorders, substance abuse, withdrawal syndromes, and tinnitus.

13. The composition of claim 1, wherein said composition comprises at least one of an SBE-β-CD-free composition, a less than 250 mg/g SBE-β-CD composition, an encapsulated cyclodextrin composition, a solid allopregnanolone comprising composition, and a non-aqueous cyclodextrin composition.

14. A method of treating a CNS disorder comprising administering an oral pharmaceutical composition to a subject, said composition comprising at least about 3% w/w of allopregnanolone, at least about 7% w/w of a hydrophilic additive, and at least about 0.9% w/w of a lipophilic additive,
   wherein said hydrophilic additive comprises at least one of polysorbate 80, polyoxyl 40 hydrogenated castor oil, sodium lauryl sulfate, sodium docusate, polyethylene glycol 1000 tocopherol succinate, PEG 400, and a poloxamer, and
   wherein said lipophilic additive comprises at least one of glyceryl monocaprylate, glyceryl monocaprylocaprate, α-tocopherol, sterol, a sterol derivative, stearic acid, a glyceride of coconut oil, and a sorbitan fatty acid ester, and wherein administration of said composition to a subject results in said subject at least one of:
- a dose normalized minimum $AUC_{0-24}$ of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L, and
- a minimum $AUC_{0-24}$ efficacy threshold of at least one of about 17 ng*h/mL, about 18 ng*h/mL, about 19 ng*h/mL, and about 20 ng*h/mL.

15. The method of claim 14, wherein when said subject is in a fasting state, administration of said composition to said subject results in said subject at least one of:
- a dose normalized maximum $C_{max}$ of at least one of about 0.28 ng mL$^{-1}$ mg$^{-1}$, about 0.26 ng mL$^{-1}$ mg$^{-1}$, about 0.24 ng mL$^{-1}$ mg$^{-1}$, about 0.22 ng mL$^{-1}$ mg$^{-1}$, about 0.20 ng mL$^{-1}$ mg$^{-1}$, about 0.18 ng mL$^{-1}$ mg$^{-1}$, about 0.16 ng mL$^{-1}$ mg$^{-1}$, about 0.14 ng mL$^{-1}$ mg$^{-1}$, about 0.13 ng mL$^{-1}$ mg$^{-1}$, and about 0.12 ng mL$^{-1}$ mg$^{-1}$, and
- a minimum $C_{max}$ of at least one of about 9.50 ng/mL, about 14.50 ng/mL, about 20.00 ng/mL, and about 25.00 ng/mL, and wherein when said subject is in a fed state, administration of said composition to said subject results in said subject at least one of:
- a dose normalized minimum $C_{max}$ in said subject of at least one of about 0.14 ng mL$^{-1}$ mg$^{-1}$, about 0.16 ng mL$^{-1}$ mg$^{-1}$, about 0.18 ng mL$^{-1}$ mg$^{-1}$, about 0.20 ng mL$^{-1}$ mg$^{-1}$, about 0.22 ng mL$^{-1}$ mg$^{-1}$, about 0.24 ng mL$^{-1}$ mg$^{-1}$, and about 0.26 ng mL$^{-1}$ mg$^{-1}$, and
- a minimum $C_{max}$ in said subject of at least one of about 4.25 ng/mL, about 4.50 ng/mL, about 4.75 ng/mL, about 5.00 ng/mL, about 5.25 ng/mL, about 5.50 ng/mL, and about 6.00 ng/mL.

16. The method of claim 14, wherein when said subject is in a fasting state, administration of said composition to said subject results in a $T_{max}$ of allopregnanolone in said subject of at least one of less than about 1.5 hours, less than about 2 hours, less than about 3 hours, and less than about 4 hours post-administration; and
wherein when said subject is in a fed state, administration of said composition to said subject results in a $T_{max}$ of allopregnanolone in said subject of at least one of less than about 1.5 hours, less than about 2 hours, less than about 3 hours, and less than about 4 hours post-administration.

17. The method of claim 14, wherein said results occur regardless of a fed or fasting state of said subject.

18. The method of claim 14, wherein said allopregnanolone comprises at least one of a solid form and a non-solid form.

19. The method of claim 14, wherein said hydrophilic additive comprises a hydrophilic surfactant having an HLB value of at least about 10, and wherein said lipophilic additive comprises a lipophilic surfactant having an HLB value of less than about 10.

20. The method of claim 14, wherein a dose of said administration comprises at least one of about 10 mg to about 1200 mg of allopregnanolone, about 20 mg to about 600 mg of allopregnanolone, about 30 mg to about 400 mg of allopregnanolone, about 40 mg to about 300 mg of allopregnanolone, about 50 mg to about 250 mg of allopregnanolone, and about 60 mg to about 180 mg of allopregnanolone.

21. The method of claim 20, wherein said dose comprises at least one of a QD dose, a BID dose, a TID dose, a QID dose, and a more than QID dose.

22. The method of claim 14, wherein when said CNS disorder comprises a major depression disorder comprising at least one of post/peri partum depression, post-menopausal depression, and essential tremor, a dose of said administration comprises at least one of about 10 mg to about 1200 mg of allopregnanolone and about 60 mg to about 180 mg of allopregnanolone, and
wherein when said CNS disorder comprises GAD, a dose of said administration comprises at least one of about 10 mg to about 1200 mg of allopregnanolone and about 60 mg to about 180 mg of allopregnanolone, and
wherein when said CNS disorder comprises OCD, a dose of said administration comprises at least one of about 10 mg to about 1200 mg of allopregnanolone and about 60 mg to about 180 mg of allopregnanolone.

23. The method of claim 14, wherein said composition comprises at least one form of a solid, liquid, a semi-liquid or semi solid, gel, a granule, a pellet, a powder, a syrup, an emulsion, a dispersion, a suspension, a capsule, a sprinkle, a tablet, a chew, a cream, an ointment, a paste, and a drink.

24. The method of claim 23, wherein said composition comprises a plurality of instances of said form.

25. The method of claim 14, wherein said CNS disorder comprises at least one of sleep disorders, mood disorders, essential tremors, depression, dysthymic disorder, bipolar disorder, anxiety disorders, stress, posttraumatic stress disorder (PTSD), compulsive disorders, schizophrenia spectrum disorders, convulsive disorders, seizures, disorders of memory, disorders of and/or cognition, dementia, movement disorders, personality disorders, autism spectrum disorders (ASD), pain, traumatic brain injury (TBI), vascular diseases, substance abuse disorders, substance abuse, withdrawal syndromes, and tinnitus.

26. The method of claim 14, wherein said composition comprises at least one of an SBE-β-CD-free composition, a less than 250 mg/g SBE-β-CD composition, an encapsulated cyclodextrin composition, a solid allopregnanolone comprising composition, and a non-aqueous cyclodextrin composition.

27. An oral pharmaceutical composition for use in treating a CNS disorder, said composition comprising about 3% to about 33% w/w of allopregnanolone, at least about 7% w/w of a hydrophilic additive, and at least about 0.9% w/w of a lipophilic additive,
wherein said hydrophilic additive has an HLB value of at least about 10, comprises about 7% to about 11% w/w of said composition, and comprises at least one of polysorbate 80, polyoxyl 40 hydrogenated castor oil, sodium lauryl sulfate, sodium docusate, polyethylene glycol 1000 tocopherol succinate, PEG 400, and a poloxamer, and
wherein said lipophilic additive has an HLB value of less than about 10, comprises about 0.9% to about 1.1% w/w of said composition, and comprises at least one of glyceryl monocaprylate, glyceryl monocaprylocaprate, α-tocopherol, sterol, a sterol derivative, stearic acid, a glyceride of coconut oil, and a sorbitan fatty acid ester, and
wherein administration of said composition to a subject results in said subject at least one of:
- a dose normalized minimum $AUC_{0-24}$ of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L, and a minimum $AUC_{0-24}$ of at least one of about 18 ng*h/mL, about 19 ng*h/mL, and about 20 ng*h/mL.

28. An oral pharmaceutical composition for use in treating a CNS disorder, said composition comprising about 3% to about 33% w/w of allopregnanolone, at least about 7% w/w of a hydrophilic additive, and at least about 0.9% w/w of a lipophilic additive, wherein said hydrophilic additive has an HLB value of at least about 10, comprises about 7% to about 11% w/w of said composition, and comprises at least one of polysorbate 80, polyoxyl 40 hydrogenated castor oil, sodium lauryl sulfate, sodium docusate, polyethylene glycol 1000 tocopherol succinate, PEG 400, and a poloxamer, and wherein said lipophilic additive has an HLB value of less than about 10, comprises about 0.9% to about 1.1% w/w of said composition, and comprises at least one of glyceryl monocaprylate, glyceryl monocaprylocaprate, α-tocopherol, sterol, a sterol derivative, stearic acid, a glyceride of coconut oil, and a sorbitan fatty acid ester, and wherein administration of said composition to a subject results in said subject:

a dose normalized minimum $AUC_{0-24}$ of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L, and a minimum $AUC_{0-24}$ efficacy threshold of at least one of about 17 ng*h/mL, about 18 ng*h/mL, about 19 ng*h/mL, and about 20 ng*h/mL.

29. The method of claim 14, wherein said allopregnanolone comprises about 3% to about 33% w/w of said composition, said hydrophilic additive has an HLB value of at least about 10, comprises about 7% to about 11% w/w of said composition, and comprises at least one of polysorbate 80, polyoxyl 40 hydrogenated castor oil, sodium lauryl sulfate, sodium docusate, polyethylene glycol 1000 tocopherol succinate, PEG 400, and a poloxamer, and said lipophilic additive has an HLB value of less than about 10, comprises about 0.9% to about 1.1% w/w of said composition, and comprises at least one of glyceryl monocaprylate, glyceryl monocaprylocaprate, α-tocopherol, sterol, a sterol derivative, stearic acid, a glyceride of coconut oil, and a sorbitan fatty acid ester.

30. An oral pharmaceutical composition for use in treating essential tremor, said composition comprising about 3% to about 33% w/w of allopregnanolone, at least about 7% w/w of a hydrophilic additive, and at least about 0.9% w/w of a lipophilic additive, wherein said hydrophilic additive has an HLB value of at least about 10, comprises about 7% to about 11% w/w of said composition, and comprises at least one of polysorbate 80, polyoxyl hydrogenated castor oil, sodium lauryl sulfate, sodium docusate, polyethylene glycol 1000 tocopherol succinate, PEG 400, and a poloxamer, and wherein said lipophilic additive has an HLB value of less than about 10, comprises about 0.9% to about 1.1% w/w of said composition, and comprises at least one of glyceryl monocaprylate, glyceryl monocaprylocaprate, α-tocopherol, sterol, a sterol derivative, stearic acid, a glyceride of coconut oil, and a sorbitan fatty acid ester, and wherein administration of at least one dose of said composition having about 10 mg to about 1200 mg of allopregnanolone to a subject having essential tremor results in said subject:

a dose normalized minimum $AUC_{0-24}$ of at least one of about 0.60 h/L, about 0.65 h/L, about 0.70 h/L, about 0.75 h/L, about 0.80 h/L, about 0.85 h/L, about 0.90 h/L, about 0.95 h/L, about 1.00 h/L, about 1.10 h/L, and about 1.20 h/L, and a minimum $AUC_{0-24}$ efficacy threshold of at least one of about 17 ng*h/mL, about 18 ng*h/mL, about 19 ng*h/mL, and about 20 ng*h/mL.

31. The composition of claim 27, wherein when said subject is in a fasting state, administration of said composition to said subject results in said subject at least one of:

a dose normalized maximum $C_{max}$ of at least one of about 0.28 ng mL$^{-1}$ mg$^{-1}$, about 0.26 ng mL$^{-1}$ mg$^{-1}$, about 0.24 ng mL$^{-1}$ mg$^{-1}$, about 0.22 ng mL$^{-1}$ mg$^{-1}$, about 0.20 ng mL$^{-1}$ mg$^{-1}$, about 0.18 ng mL$^{-1}$ mg$^{-1}$, about 0.16 ng mL$^{-1}$ mg$^{-1}$, about 0.14 ng mL$^{-1}$ mg$^{-1}$, about 0.13 ng mL$^{-1}$ mg$^{-1}$, and about 0.12 ng mL$^{-1}$ mg$^{-1}$, and a minimum $C_{max}$ of at least one of about 9.50 ng/mL, about 14.50 ng/mL, about 20.00 ng/mL, and about 25.00 ng/mL, and wherein when said subject is in a fed state, administration of said composition to said subject results in said subject at least one of:

a dose normalized minimum $C_{max}$ in said subject of at least one of about 0.14 ng mL$^{-1}$ mg$^{-1}$, about 0.16 ng mL$^{-1}$ mg$^{-1}$, about 0.18 ng mL$^{-1}$ mg$^{-1}$, about 0.20 ng mL$^{-1}$ mg$^{-1}$, about 0.22 ng mL$^{-1}$ mg$^{-1}$, about 0.24 ng mL$^{-1}$ mg$^{-1}$, and about 0.26 ng mL$^{-1}$ mg$^{-1}$, and a minimum $C_{max}$ in said subject of at least one of about 4.25 ng/mL, about 4.50 ng/mL, about 4.75 ng/mL, about 5.00 ng/mL, about 5.25 ng/mL, about 5.50 ng/mL, and about 6.00 ng/mL.

32. The composition of claim 28, wherein when said subject is in a fasting state, administration of said composition to said subject results in said subject at least one of:

a dose normalized maximum $C_{max}$ of at least one of about 0.28 ng mL$^{-1}$ mg$^{-1}$, about 0.26 ng mL$^{-1}$ mg$^{-1}$, about 0.24 ng mL$^{-1}$ mg$^{-1}$, about 0.22 ng mL$^{-1}$ mg$^{-1}$, about 0.20 ng mL$^{-1}$ mg$^{-1}$, about 0.18 ng mL$^{-1}$ mg$^{-1}$, about 0.16 ng mL$^{-1}$ mg$^{-1}$, about 0.14 ng mL$^{-1}$ mg$^{-1}$, about 0.13 ng mL$^{-1}$ mg$^{-1}$, and about 0.12 ng mL$^{-1}$ mg$^{-1}$, and a minimum $C_{max}$ of at least one of about 9.50 ng/mL, about 14.50 ng/mL, about 20.00 ng/mL, and about 25.00 ng/mL, and wherein when said subject is in a fed state, administration of said composition to said subject results in said subject at least one of:

a dose normalized minimum $C_{max}$ in said subject of at least one of about 0.14 ng mL$^{-1}$ mg$^{-1}$, about 0.16 ng mL$^{-1}$ mg$^{-1}$, about 0.18 ng mL$^{-1}$ mg$^{-1}$, about 0.20 ng mL$^{-1}$ mg$^{-1}$, about 0.22 ng mL$^{-1}$ mg$^{-1}$, about 0.24 ng mL$^{-1}$ mg$^{-1}$, and about 0.26 ng mL$^{-1}$ mg$^{-1}$, and a minimum $C_{max}$ in said subject of at least one of about 4.25 ng/mL, about 4.50 ng/mL, about 4.75 ng/mL, about 5.00 ng/mL, about 5.25 ng/mL, about 5.50 ng/mL, and about 6.00 ng/mL.

33. The composition of claim 30, wherein when said subject is in a fasting state, administration of said composition to said subject results in said subject at least one of:

a dose normalized maximum $C_{max}$ of at least one of about 0.28 ng mL$^{-1}$ mg$^{-1}$, about 0.26 ng mL$^{-1}$ mg$^{-1}$, about 0.24 ng mL$^{-1}$ mg$^{-1}$, about 0.22 ng mL$^{-1}$ mg$^{-1}$, about 0.20 ng mL$^{-1}$ mg$^{-1}$, about 0.18 ng mL$^{-1}$ mg$^{-1}$, about 0.16 ng mL$^{-1}$ mg$^{-1}$, about 0.14 ng mL$^{-1}$ mg$^{-1}$, about 0.13 ng mL$^{-1}$ mg$^{-1}$, and about 0.12 ng mL$^{-1}$ mg$^{-1}$, and a minimum $C_{max}$ of at least one of about 9.50 ng/mL, about 14.50 ng/mL, about 20.00 ng/mL, and about 25.00 ng/mL, and wherein when said subject is in a fed state, administration of said composition to said subject results in said subject at least one of:

a dose normalized minimum $C_{max}$ in said subject of at least one of about 0.14 ng mL$^{-1}$ mg$^{-1}$, about 0.16 ng mL$^{-1}$ mg$^{-1}$, about 0.18 ng mL$^{-1}$ mg$^{-1}$, about 0.20 ng mL$^{-1}$ mg$^{-1}$, about 0.22 ng mL$^{-1}$ mg$^{-1}$, about 0.24 ng mL$^{-1}$ mg$^{-1}$, and about 0.26 ng mL$^{-1}$ mg$^{-1}$, and a minimum $C_{max}$ in said subject of at least one of about 4.25 ng/mL, about 4.50 ng/mL, about 4.75 ng/mL, about 5.00 ng/mL, about 5.25 ng/mL, about 5.50 ng/mL, and about 6.00 ng/mL.

* * * * *